(12) United States Patent
Rao et al.

(10) Patent No.: US 7,893,035 B2
(45) Date of Patent: Feb. 22, 2011

(54) MULTICISTRONIC CONSTRUCTS WITH SIRNA TO INHIBIT TUMORS

(75) Inventors: Jasti S. Rao, Peoria, IL (US); Christopher S. Gondi, Peoria, IL (US); Sajani S. Lakka, Peoria, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 145 days.

(21) Appl. No.: 11/748,733

(22) Filed: May 15, 2007

(65) Prior Publication Data

US 2008/0020992 A1 Jan. 24, 2008

Related U.S. Application Data

(63) Continuation-in-part of application No. PCT/US2005/041709, filed on Nov. 17, 2005.

(60) Provisional application No. 60/629,659, filed on Nov. 18, 2004.

(51) Int. Cl.
A01N 43/04 (2006.01)
A61K 31/70 (2006.01)
C07H 21/04 (2006.01)

(52) U.S. Cl. ........................ 514/44; 536/24.5

(58) Field of Classification Search ................ 536/24.5; 514/44
See application file for complete search history.

(56) References Cited

U.S. PATENT DOCUMENTS

| | | | |
|---|---|---|---|
| 6,224,865 B1 | 5/2001 | Brunner et al. | |
| 6,316,181 B1 * | 11/2001 | Fillmore et al. | ................ 435/4 |
| 6,462,170 B1 | 10/2002 | Blasi et al. | |
| 6,573,099 B2 * | 6/2003 | Graham | ...................... 435/455 |
| 2003/0138429 A1 | 7/2003 | Pizzo et al. | |
| 2003/0148973 A1 | 8/2003 | Emtage et al. | |
| 2004/0077082 A1 * | 4/2004 | Koehn et al. | ................ 435/375 |
| 2004/0142897 A1 | 7/2004 | Waisman | |
| 2004/0229266 A1 | 11/2004 | Tuschl et al. | |
| 2005/0031620 A1 | 2/2005 | Thorpe et al. | |
| 2005/0043266 A1 * | 2/2005 | Jayasena et al. | ................ 514/44 |
| 2005/0059044 A1 * | 3/2005 | Graham et al. | ................ 435/6 |
| 2005/0130184 A1 | 6/2005 | Xu et al. | |
| 2005/0164965 A1 | 7/2005 | Reddy et al. | |
| 2005/0197313 A1 | 9/2005 | Roelvink et al. | |
| 2005/0233997 A1 | 10/2005 | Richards et al. | |
| 2005/0234007 A1 | 10/2005 | Tuschl et al. | |

FOREIGN PATENT DOCUMENTS

WO WO 2004/054517 A2 7/2004

OTHER PUBLICATIONS

Lakka et al. (Cancer Research 63: 2454-2461, 2003).*
Gondi et al. (Neuron Glia Biology, 2004, 1, 165-176).*
Gondi et al. Neuro-Oncology, 6: 309-310, 2004.*
Gondi et al., "RNAi-meidated inhibition of cathepsin B and uPAR leads to decreased cell invasion, angiogenesis and tumor growth in gliomas," Oncogene, 23(52): 8486-8496 (2004).
Search report from related application No. EP05826614 (2008).
Hannon, Gregory J., "RNA interference," Nature, 418: 244-251 (2001).
Adachi et al., "Down-regulation of Integrin $\alpha_v 62_3$ Expression and Integrin-mediated Signaling in Glioma Cells by Adenovirus-mediated Transfer of Antisense Urokinase-type Plasminogen Activator Receptor (μPAR) and Sense p16 Genes," The Jrnl. of Biol. Chem., 276 (50): 47171-47177 (2001).
Aguirre-Ghiso et al., ERK$^{MAPK}$ Activity as a Determinant of Tumor Growth and Dormancy; Regulation by p38$^{SAPK}$, Cancer Res., 63: 1684-1695 (2003).
Aguirre-Ghiso et al., "Tumor Dormancy Induced by Downregulation of Urokinase Receptor in Human Carcinoma Involves Integrin and MAPK Signaling," Jrnl. of Cell Biol., 147 (1): 89-103 (1999).
Ahmed et al., "Downregulation of urokinase plasminogen activator receptor expression inhibits Erk signalling with concomitant suppression of invasiveness due to loss of uPAR-β1 integrin complex in colon cancer cells," Brit. Jrnl. of Cancer, 89: 374-384 (2003).
Aoki et al., "Effects of various steroids on platelet-derived endothelial cell growth factor (PD-ECGF) and its mRNA expression in uterine endometrial cancer cells," Jrnl. of Steroid Biochem. & Mol. Biol., 84: 217-222 (2003).
Bergers et al., "Effects of Angiogenesis Inhibitors on Multistage Carcinogenesis in Mice," Science, 284 (5415): 808-812 (1999).
Blasi et al., "uPAR: A Versatile Signalling Orchestrator," Mol. Cell. Biol., 3: 932-943 (2002).
Boyd et al., "A Urokinase-Derived Peptide (Å6) Increases Survival of Mice Bearing Orthotopically Grown Prostate Cancer and Reduces Lymph Node Metastasis," Amer. Jrnl. of Path., 162 (2): 619-626 (2003).
Brown et al., "Association Between Expression of Activated 72-Kilodalton Gelatinase and Tumor Spread in Non-Small-Cell Lung Carcinoma," Jrnl. of the New Natl. Can. Inst., 85:7 574-578 (1993).
Caplen et al., "Specific inhibition of gene expression by small double-stranded RNAs in invertebrate and vertebrate systems," PNAS, 98 (17): 9742-9747 (2001).
Chandrasekar et al., "Downregulation of uPA inhibits migration and PI3k/Akt signaling in gliobastoma cells," Oncogene, 22: 392-400 (2003).
Choe, et al., "Active Matrix Metalloproteinase 9 Expression Is Associated with Primary Glioblastoma Subtype," Clin. Can. Res., 8: 2894-2901 (2002).

(Continued)

Primary Examiner—Brian Whiteman
(74) Attorney, Agent, or Firm—Barnes & Thornburg LLP; Alice O. Martin

(57) ABSTRACT

Multicistronic short interfering RNA constructs targeting in various combinations a human urokinase-type plasminogen activator receptor (uPAR), human urokinase-type plasminogen activator (uPA), human matrix metalloprotease 9 (MMP-9) and cathepsin B (CB) inhibit tumors.

13 Claims, 50 Drawing Sheets

OTHER PUBLICATIONS

D'Alessio et al., "Antisense Oligodeoxynucleotides for Urokinase-Plasminogen Activator Receptor have Anti-Invasive and Anti-Proliferative Effects in Vitro and Inhibit Spontaneous Metastases of Human Melanoma in Mice," *Int. J. Cancer*, 110: 125-133 (2004).

Dahiya et al., "Inhibitation of Tumorigenic Potential and Prostate-Specific Antigen Expression in LNCAP Human Prostate Cancer Cell Line by 13-*cis*-Retinoic Acid," *Int. J. Cancer*, 59: 126-132 (1994).

Degryse et al., "The High Mobility Group (HMG) Boxes of the Nuclear Protein HMG1 Induce Chemotaxis and Cytoskeleton Reorganization in Rat Smooth Muscle Cells," *The J. of Cell Biology*, 152 (6): 1197-1206 (2001).

Drummond et al., "Preclinical and Clinical Studies of MMP Inhibitors in Cancer," *Annals NY Academy of Sci*, 878: 228-235 (1999).

Dumler et al., "The Jak/Stat Pathway and Urokinase Receptor Signaling in Human Aortic Vascular Smooth Muscle Cells," *The Jrnl. of Biol. Chem.*, 273 (1): 315-321 (1998).

Elbashir et al., "Duplexes of 21-nucleotide RNAs mediate RNA interference in cultured mammalian cells," *Nature*, 411: 494-498 (2001).

Elbashir et al., "Analysis of gene function in somatic mammalian cells using small interfering RNAs," *Methods*, 26: 199-213 (2002).

Ellis et al., "Potentiation of Plasminogen Activation by an Antiurokinase Monoclonal Antibody Due to Ternary Complex Formation," *The Jrnl. Of Biol. Chem.*, 268 (7): 4806-4813 (1993).

Fabbrini et al., "The amino-terminal fragment of human urokinase directs a recombinant chimeric toxin to target cells: internalization is toxin mediated," *FASEB Jrnl.*, 11: 1169-1176 (1997).

Forsyth et al., "Gelatinase-A (MMP-2), gelatinase-B (MMP-9) and membrane type matrix metalloproteinase-1 (MT1-MMP) are involved in different aspects of the pathophysiology of malignant gliomas," *Brit. Jrnl. Of Cancer*, 79 (11/12):, 1828-1835 (1999).

Giannelli et al., "Protease Susceptibility and Toxicity of Heat-Labile Enterotoxins with a Mutation in the Active Site or in the Protease-Sensitive Loop," *Infection and Immunity*, 65 (1): 331-334 (1997).

Giese et al., "Glioma Invasion in the Central Nervous System," *Neurosurgery*, 39 (2): 235-252 (1996).

Go et al., "Inhibition of in vivo tumorigenicity and invasiveness of a human glioblastoma cell line transfected with antisense uPAR vectors," *Clin. Exp. Metastasis*, 15 (4): 440-446 (1997).

Gondi et al., "Expression of antisense uPAR and antisense uPA from a bicistronic adenoviral construct inhibits glioma cell invasion, tumor growth, and angiogenesis," *Oncogene*, 22: 5967-5975 (2003).

Guo et al., "A peptide derived from the nonreceptor binding region of urokinase plasminogen activator (uPA) inhibits tumor progression and angiogenesis and induces tumor cell death in vivo," *FASEB Jrnl.*, 14: 1400-1410 (2000).

Hood et al., "Tumor Regression by Targeted Gene Delivery to the Neovasculature," *Science*, 296: 2404-2407 (2002).

Jiang et al., Gel-Based Application of siRNA to Human Epithelial Cancer Cells Induces RNAi-Dependent Apoptosis, *Oligonucleotides*, 14: 239-248 (2004).

Jo et al., "Epidermal Growth Factor Receptor-dependent and -independent Cell-signaling Pathways Originating from the Urokinase Receptor," *The Jrnl. Of Biol. Chem.*, 278 (3): 1642-1646 (2003).

Joossens et al., "Development of Irreversible Diphenyl Phosphonate Inhibitors for Urokinase Plasminogen Activator," *J. Med. Chem.*, 47: 2411-2413 (2004).

Kajita et al., "Membrane-type 1 Matrix Metalloproteinase Cleaves CD44 and Promotes Cell Migration," *The Jrnl. Of Cell Biol.*, 153 (5): 893-904 (2001).

Keer et al., "Heterogeneity in Plasminogen Activator (PA) Levels in Human Prostate Cancer Cell Lines: Increased PA Activity Correlates With Biologically Aggressive Behavior," *The Prostate*, 18: 201-214 (1991).

Kim et al., "Reduced c-Met Expression by an Adenovirus Expressing a c-Met Ribozyme Inhibits Tumorigenic Growth and Lymph Node Metastases of PC2-LN4 Prostate Tumor Cells in an Orthotopic Nude Mouse Model," *Clinical Cancer Research*, 9: 5161-5170 (2003).

Kim et al., "Simultaneous Blockade of Platelet-Derived Growth Factor-Receptor and Epidermal Growth Factor-Receptor Signaling and Systemic Administration of Paclitaxel as Therapy for Human Prostate Cancer Metastasis in Bone of Nude Mice," *Cancer Research*, 64: 4201-4208 (2004).

Kondraganti et al., "Selective Suppression of Matrix Metalloproteinase-9 in Human Glioblastoma Cells by Antisense Gene Transfer Impairs Glioblastoma Cell Invasion," *Cancer Research*, 60: 6851-6855 (2000).

Laiho et al., "Growth Factors in the Regulation of Pericellular Proteolysis: A Review," *Cancer Research*, 49: 2533-2553 (1989).

Lakka et al. "Regulation of MMP-9 (type IV collagenase) production and invasiveness in gliomas by the extracellular signal-regulated kinase and jun amino-terminal kinase signaling cascades," *Clinical & Experimental Metastasis*, 18: 245-252 (2000).

Lakka et al., "Downregulation of MMP-i in ERK-mutated stable transfectants inhibits glioma invasion in vitro," *Onogene*, 21: 5601-5608 (2002).

Lakka et al., "Adenovirus-mediated expression of antisense MMP-9 in glioma cells inhibits tumor growth and invasion," *Oncogene*, 21: 8011-8019 (2002).

Lakka et al., "Inhibition of cathepsin B and MMP-9 gene expression in glioblastoma cell line via RNA interference reduces tumor cell invasion, tumor growth and angiogenesis," *Oncogene*, 23: 4681-4689 (2004).

Laniado et al., "Expression and Functional Analysis of Voltage-Activated $Na^+$ Channels in Human Prostate Cancer Cell Lines and their Contribution to Invasion in Vitro," *AJP*, 150 (4): 1213-1221 (1997).

Legrand et al., "uPA/Plasmin System-Mediated MMP-9 Activation Is Implicated in Bronchial Epithelial Cell Migration," *Exp. Cell Res.*, 264: 326-336 (2001).

Ma et al., "Endogenously produced urokinase-type plasminogen activator is a major determinant of the basal level of activated ERK/MAP kinase and prevents apoptosis in MDA-MB-231 breast cancer cells," *Jrnl of Cell Sci.*, 114 (18): 3387-3396 (2001).

Mamoune et al., "DU145 human prostate carcinoma invasiveness is modulated by urokinase receptor (uPAR) downstream of epidermal growth factor receptor (EGFR) signaling," *Exp. Cell Res.*, 299: 91-100 (2004).

Margheri et al., "Effects of blocking urokinase receptor signaling by antisense oligonucleotides in a mouse model of experimental prostate cancer bone metastases," *Gene Therapy*, 12: 702-714 (2005).

Mazzieri et al., "Control of type IV collagenase activity by components of the urokinase-plasmin system: a regulatory mechanism with cell-bound reactants," *The EMBO Jrnl.*, 16 (9): 2319-2332 (1997).

McManus et al., "Gene Silencing in Mammals by Small Interfering RNAs," *Nature*, 3: 737-747 (2002).

Miyagishi et al., "U6 promoter-driven siRNAs with four uridine 3' overhangs efficiently suppress targeted gene expression in mammalian cells," *Nature Biotech.*, 19: 497-500 (2002).

Miyagishi et al., "Comparison of the Suppressive Effects of Antisense Oligonucleotides and siRNAs Directed Against the Same Targets in Mammalian Cells," *Antisense and Nucleic Acid Drug Development*, 13: 1-7 (2003).

Mohan et al., "Adenovirus-mediated Delivery of Antisense Gene to Urokinase-type Plasminogen Activator Receptor Suppresses Glioma Invasion and Tumor Growth," *Cancer Res.*, 59: 3369-3373 (1999).

Mohan et al., "Modulation of TNF-α-Induced Apoptosis in Corneal Fibroblasts by Transcription Factor NF-κB," *IOVS*, 41 (6): 1327-1336 (2000).

Mohanam et al., "In vitro inhibition of human glioblastoma cell line invasiveness by antisense uPA receptor," *Oncogene*, 14: 1351-1359 (1997).

Mora et al., "Constitutive Activation of Stat3 in Human Prostate Tumors and Cell Lines: Direct Inhibition of Stat3 Signaling Induces Apoptosis of Prostate Cancer Cells," *Cancer Res.*, 62: 6659-6666 (2002).

Mori et al., "Up-regulation of urokinase-type plasminogen activator and its receptor correlates with enhances invasion activity of human glioma cells mediated by transforming growth factor-α or basic fibroblast growth factor," *Jrnl. Of Neuro-Oncology*, 46: 115-123 (2000).

Moses, "The Regulation of Neovascularization by Matrix Metalloproteinases and Their Inhibitors," *Stem Cells*, 15 (3): 180-189 (1997).

Naldini et al., "Extracellular proteolytic cleavage by urokinase is required for activation of hepatocyte growth factor/scatter factor," *The EMBO Jrnl.*, 11 (13): 4825-4833 (1992).

Nguyen et al., "Binding of Urokinase-type Plasminogen Activator to Its Receptor in MCF-7 Cells Activates Extracellular Signal-regulated Kinase 1 and 2 Which Is Required for Increased Cellular Motility," *The Jrnl. Of Biol. Chem.*, 273 (14): 8502-8507 (1998).

Nguyen et al., "Urokinase-type Plasminogen Activator Stimulates the Ras/Extracellular Signal-regulated Kinase (ERK) Signaling Pathway and MCF-7 Cell Migration by a Mechanism That Requires Focal Adhesion Kinase, Src, and Shc," *The Jrnl. Of Biol. Chem.*, 275 (25): 19382-19388 (2000).

Nishimura et al., "Effects of hepatocyte growth factor on urokinase-type plasminogen activator (uPA) and uPA receptor in DU145 prostate cancer cells," *Intl. Jrnl. Of Andrology*, 26: 175-179 (2003).

Ossowski et al., "Inhibition of Urokinase-type Plasminogen Activator by Antibodies: The Effect on Dissemination of a Human Tumor in the Nude Mouse," *Cancer Res.*, 51: 274-281 (1991).

Paddison et al., "RNA interference: the new somatic cell genetics?," *Cancer Cell*, 2: 17-23 (2002).

Pakneshan et al., "Methylation status of uPA promoter as a molecular mechanism regulating prostate cancer invasion and growth in vitro and in vivo," *The FAASEB Jrnl.*, 17: 1081-1088 (2003).

Pakneshan et al., "Reversal of the Hypomethylation Status of Urokinase (uPA) Promoter Blocks Breast Cancer Growth and Metastasis," *The Jrnl. Of Biol. Chem.*, 279 (30): 31735-31744 (2004).

Park et al., "PTEN Suppresses Hyaluronic Acid-induced Matrix Metalloproteinase-9 Expression in U87MG Glioblastoma Cells through Focal Adhesion Kinase Dephosphorylation," *Cancer Res.*, 62: 6318-6322 (2002).

Patel et al., "Is gene therapy the answer for prostate cancer?," *Prostate Cancer and Prostatic Diseases*, 7: S14-S19 (2004).

Pinthus et al., "Adoptive immunotherapy of prostate cancer bone lesions using redirected effector lymphocytes," *The Jrnl. Of Clin. Invest.*, 114 (12): 1774-1781 (2004).

Rabbani et al., "Urokinase Receptor Antibody Can Reduce Tumor Volume and Detect the Presence of Occult Tumor Metastases in Vivo," *Cancer Res.* 62: 2390-2397 (2002).

Rakic et al., "Placental Growth Factor, a Member of the VEGF Family, Contributes to the Development of Choroidal Neovascularization," *Invest. Ophthalmology & Visual Sci.*, 44 (7): 3186-3193 (2003).

Ramos-DeSimone et al., "Activation of Matrix Metalloproteinase-9 (MMP-9) via a Converging Plasmin/Stromelysin-1 Cascade Enhances Tumor Cell Invasion," *The Jrnl. Of Biol. Chem.*, 274:19 13066-13076 (1999).

Rao et al., "Elevated Levels of $M_r$ 92,000 Type IV Collagenase in Human Brain Tumors," *Cancer Res.*, 53: 2208-2211 (1993).

Rao, Jasti S., "Molecular Mechanisms of Glioma Invasiveness: The Role of Proteases," *Nature Reviews*, 3: 489-501 (2003).

Resnati et al., "The fibrinolytic receptor for urokinase activates the G protein-coupled chemotactic receptor FPRL1/LXA4R," *PNAS*, 99:3 1359-1364 (2002).

Rye et al., "Interfering with Cancer: A Brief Outline of Advances in RNA Interference in Oncology," *Tumor Biol.*, 25: 329-336 (2004).

Salvi et al., "Small interfering RNA urokinase silencing inhibits invasion and migration of human hepatocellular carcinoma cells," *Mol. Cancer Ther.*, 3 (6): 671-678 (2004).

Sato et al., "High-affinity urokinase-derived cyclic peptides inhibiting urokinase/urokinase receptor-interaction: effects on tumor growth and spread," *Science Direct—FEBS Letters*, 528: Issues 1-3, 212-216 (2002).

Sawaya et al., "Elevated Levels of $M_r$ 92,000 Type IV Collagenase during Tumor Growth in Vivo," *Biochemical and Biophysical Res. Comm.*, 251: 632-636 (1998).

Schuh et al., "Protease Inhibitors Prevent Plasminogen-Mediated, But Not Pemphigus Vulgaris-Induced, Acantholysis in Human Epidermis," *Biol. Chem.*, 384: 311-315 (2003).

Schweinitz et al., "Design of Novel and Selective Inhibitors of Urokinase-type Plasminogen Activator with Improved Pharmacokinetic Properties for Use as Antimetastatic Agents," *The Jrnl. Of Biol. Chem.*, 279 (32): 33613-33622 (2004).

Shah et al., "Androgen-Independent Prostate Cancer Is a Heterogeneous Group of Diseases: Lessons from a Rapid Autopsy Program," *Cancer Res.*, 64: 9209-9216 (2004).

Sharp, Phillip A., "RNA interference—2001," *Genes & Devel.*, 15: 485-490 (2001).

Simon et al., "Inhibition of the p38 Mitogen-activated protein Kinase by SB 203580 Blocks PMA-induced $M_r$ 92,000 Type IV collagenase Secretion and in Vitro Invasion," *Cancer Res.*, 58: 1135-1139 (1998).

Singh et al., "Expression and Functional Role of CCR9 in Prostate Cancer Cell Migration and Invasion," *Clin. Cancer Res.*, 10: 8743-8750 (2004).

Sontheimer, Erik J., "Assembly and Function of RNA Silencing Complexes," *Mol. Cell Biol.*, 6: 127-138 (2005).

Stewart et al., "Changes in Extracellular matrix (ECM) and ECM-associated proteins in the metastatic progression of prostate cancer," *Reproductive Biol. And Endo.*, 2:2 (2004).

Tang et al., "The Urokinase-type Plasminogen Activator Receptor Mediates Tyrosine Phosphorylation of Focal Adhesion Proteins and Activation of Mitogen-activated Protein Kinase in Cultured Endothelial Cells," 273 (29): 18268-18272 (1998).

Tarui et al., "Critical Role of Integrin $\alpha_5\beta_1$ in Urokinase (uPA)/Urokinase Receptor (uPAR, CD87) Signaling," *The Jrnl. Of Biol. Chem.*, 278 (32): 29863-29872 (2003).

Trisciuoglio et al. "*bcl-2* Induction of Urokinase Plasminogen Activator Receptor Expression in Human Cancer Cells through Sp1 Activation," *The Jrnl. Of Biol. Chem.*, 279 (8): 6737-6745 (2004).

Usher et al., "Expression of urokinase plasminogen activator, its receptor and type-1 inhibitor in malignant and benign prostate tissue," *Int. J. Cancer*, 113: 870-880 (2005).

Woessmann et al., "RNA Interference: New Mechanisms for Targeted Treatment?," *Rev. Clin. Exp. Hematol.*7 (3): 270-291(2003).

Yamamoto et al., "Expression and Localization of Urokinase-type Plasminogen Activator Receptor in Human Gliomas," *Cancer Res.*, 54: 5016-5020 (1994).

Yao et al., "Multiple signaling pathways involved in activation of matrix metalloproteinase-9 (MMP-9) by heregulin-$\beta1$ in human breast cancer cells," *Oncogene*, 20: 8066-8074 (2001).

Yu et al., "Expression of Multiple CD44 Isoforms in the Apical Ectodermal Ridge of the Embryonic Mouse Limb," *Devel. Dynamics*, 207: 204-214 (1996).

Yu et al., "Cell surface-localized matrix metalloproteinase-9 proteolytically activates TGF-$\beta$ and promotes tumor invasion and angiogenesis," *Genes & Devel.*, 14: 163-176 (2000).

Zhang et al., "Antisense therapy targeting MDM2 oncogene in prostate cancer: Effects on proliferation, apoptosis, multiple gene expression, and chemotherapy," *PNAS*, 100 (20): 11636-11641 (2003).

Zhang et al., "Intravenous RNA Interference Gene Therapy Targeting the Human Epidermal Growth Factor Receptor Prolongs Survival in Intracranial Brain Cancer," *Clin. Can. Res.*, 10: 3667-3677 (2004).

Zhang et al., "Persistent c-FLIP(L) Expression Is Necessary and Sufficient to Maintain Resistance to Tumor Necrosis Factor-Related Apoptosis-Inducing Ligand-Mediated Apoptosis in Prostate Cancer," *Cancer Res.*, 64: 7086-7091 (2004).

International Search Report issued in PCT/US2005/41709 (2007).

Gondi et al., "Downregulation of uPAR, uPA, MMP-9 and cathepsin B gene expression in a glioblastoma cell line via RNA interference inhibits tumor cell invasion, angiogenesis and tumor regression," *Proceedings Of The Annual Meeting Of The American Association For Cancer Research, American Association For Cancer Research*, 45: 835 (2004). Abstract.

Lakka et al., "Specific interference of urokinase-type plasminogen activator receptor and matrix metalloproteinase-9 gene expression induced by double-stranded RNA results in decreased invasion, tumor growth, and angiogenesis in gliomas," *Journal Of Biological Chemistry*, 280(23): 21882-21892 (2005).

Search Report issued in European application No. EP10002432 (2010).

* cited by examiner

Schematic representation of recombinant adenovirus production

SNB19 GFP cells | SNB19 GFP cells (GFP RNAi)

pU2 partial RNA structure

SEQUENCE LISTING

```
<160> NUMBER OF SEQ ID NOS: 39

<210> SEQ ID NO 1
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 1
tgagagccct gctggcgcgc cnnnnnnnnn ggcgcgccag cagggctctc a         51

<210> SEQ ID NO 2
<211> LENGTH: 51
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 2
ctacagcagt ggagagcgat tnnnnnnnnn aatcgctctc cactgctgta g         51

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 3
agcttggtac cgagctcgga tc                                          22

<210> SEQ ID NO 4
<211> LENGTH: 51
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 4
caagtggcac caccacaaca annnnnnnnn ttgttgtggt ggtgccactt g           51

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
gatccactag taacggccgc cagtgtgctg gaatt                            35

<210> SEQ ID NO 6
<211> LENGTH: 49
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(29)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 6
caagtggcac caccacaaca nnnnnnnnnt gttgtggtgg tgccacttg             49
```

<210> SEQ ID NO 7
<211> LENGTH: 68
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
gatccactag taacggccgc cagtgtgctg gaattctgca gatatccatc acactggcgg      60
ccgctcga                                                              68

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
aattctgcag atatccatca cactggcggc cgctcga                              37

<210> SEQ ID NO 9
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 9
cuacagcagu ggagagcgau unnnnnnnnn aaucgcucuc cacugcugua g              51

<210> SEQ ID NO 10
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 10
caaguggcac caccacaaca annnnnnnnn uuguuguggu ggugccacuu g              51

<210> SEQ ID NO 11
<211> LENGTH: 51
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (22)..(30)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 11
ugagagcccu gcuggcgcgc cnnnnnnnnn ggcgcgccag cagggcucuc a           51

<210> SEQ ID NO 12
<211> LENGTH: 49
<212> TYPE: RNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (21)..(29)
<223> OTHER INFORMATION: variable 9 nucleotide loop
<220> FEATURE:
<223> OTHER INFORMATION: see specification as filed for detailed
      description of substitutions and preferred embodiments

<400> SEQUENCE: 12
caaguggcac caccacaaca nnnnnnnnnu guuguggugg ugccacuug              49

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
aggtggtaaa gggtggctcc                                              20

<210> SEQ ID NO 14
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
acaaccaggt cagcgtcaga t                                            21

<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctggtgtcga cctgcttccg cgatgtacgg gc                                32

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16

-continued

```
ctggtgtcga catccccagc atgcctgcta t                              31
```

<210> SEQ ID NO 17
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17

```
agcttgagag ccctgctggc gcgccatata taatggcgcg ccagcagggc tctca        55
```

<210> SEQ ID NO 18
<211> LENGTH: 55
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 18

```
gatcctacag cagtggagag cgattatata taataatcgc tctccactgc tgtag        55
```

<210> SEQ ID NO 19
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 19

```
aattcaagtg gcaccaccac aacaatatat aattgttgtg gtggtgccac ttg          53
```

<210> SEQ ID NO 20
<211> LENGTH: 53
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 20

```
tcgaggtggc ctctatgaat cccaatatat aattgggatt catagaggcc acc          53
```

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21

```
tgcgtcctgg tcgtgagcga                                              20
```

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

-continued ctacagcgct gacacgcttg                                               20

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catgcagtgt aagacccaac gggga                                         25

<210> SEQ ID NO 24
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
aataggtgac agcccggcca gagt                                          24

<210> SEQ ID NO 25
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cggagtcaac ggatttggtc gtat                                          24

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
agccttctcc atggtggtga agac                                          24

<210> SEQ ID NO 27
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gttcgaaatt agtttggtta ac                                            22

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
ccgaataact aatattataa acg                                           23

<210> SEQ ID NO 29
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 29
gagctgttca ccgggtggt g                                              21

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 30
ctacagcagt ggagagcgat t                                             21

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 31
caagtggcac caccacaaca a                                             21

<210> SEQ ID NO 32
<211> LENGTH: 444
<212> TYPE: DNA
<213> ORGANISM: Artificial Sequence
<220> FEATURE:
<223> OTHER INFORMATION: Description of Artificial Sequence: Synthetic
      siRNA construct

<400> SEQUENCE: 32
gctaactaga gaacccactg cttactggct tatcgaaatt aatacgactc actataggga    60
gacccaagct tgagagccct gctggcgcgc catatataat ggcgcgccag cagggctctc   120
aagcttggta ccgagctcgg atcctacagc agtggagagc gattatatat aataatcgct   180
ctccactgct gtaggatcca ctagtaacgg ccgccagtgt gctggaattc tgcagatatc   240
catcacactg gcggccgctc gagcatgcat ctagagggcc ctattctata gtgtcaccta   300
aatgctagag ctcgctgatc agcctcgact gtgccttcta gttgccagcc atctgttgtt   360
tgcccctccc ccgtgccttc cttgaccctg gaaggtgcca ctcccactgt cctttcctaa   420 taaaaaaaa aaaaaaaaa aaaa                                           444

<210> SEQ ID NO 33
<211> LENGTH: 442
<212> TYPE: DNA
<213> ORGANISM: Artificial Sequence
<220> FEATURE:
<223> OTHER INFORMATION: Description of Artificial Sequence: Synthetic
      siRNA construct

<400> SEQUENCE: 33
gctaactaga gaacccactg cttactggct tatcgaaatt aatacgactc actataggga    60

```
gacccaagct tggtaccgag ctcggatcct acagcagtgg agagcgatta tatataataa    120
tcgctctcca ctgctgtagg atccactagt aacggccgcc agtgtgctgg aattcaagtg    180
gcaccaccac aacaatatat aattgttgtg gtggtgccac ttgaattctg cagatatcca    240
tcacactggc ggccgctcga gcatgcatct agagggccct attctatagt gtcacctaaa    300
tgctagagct cgctgatcag cctcgactgt gccttctagt tgccagccat ctgttgtttg    360
cccctccccc gtgccttcct tgaccctgga aggtgccact cccactgtcc tttcctaata    420
aaaaaaaaaa aaaaaaaaaa aa                                             442

<210> SEQ ID NO 34
<211> LENGTH: 442
<212> TYPE: DNA
<213> ORGANISM: Artificial Sequence
<220> FEATURE:
<223> OTHER INFORMATION: Description of Artificial Sequence: Synthetic
      siRNA construct

<400> SEQUENCE: 34
gctaactaga gaacccactg cttactggct tatcgaaatt aatacgactc actataggga     60
gacccaagct tggtaccgag ctcggatcct acagcagtgg agagcgatta tatataataa    120
tcgctctcca ctgctgtagg atccactagt aacggccgcc agtgtgctgg aattctgcag    180
atatccatca cactggcggc cgctcgaggt ggcctctatg aatcccaata tataattggg    240
attcatagag gccacctcga gcatgcatct agagggccct attctatagt gtcacctaaa    300
tgctagagct cgctgatcag cctcgactgt gccttctagt tgccagccat ctgttgtttg    360
cccctccccc gtgccttcct tgaccctgga aggtgccact cccactgtcc tttcctaata    420
aaaaaaaaaa aaaaaaaaaa aa                                             442

<210> SEQ ID NO 35
<211> LENGTH: 440
<212> TYPE: DNA
<213> ORGANISM: Artificial Sequence
<220> FEATURE:
<223> OTHER INFORMATION: Description of Artificial Sequence: Synthetic
      siRNA construct

<400> SEQUENCE: 35
gctaactaga gaacccactg cttactggct tatcgaaatt aatacgactc actataggga     60
gacccaagct tggtaccgag ctcggatcca ctagtaacgg ccgccagtgt gctggaattc    120
aagtggcacc accacaacaa tatataattg ttgtggtggt gccacttgaa ttctgcagat    180
atccatcaca ctggcggccg ctcgaggtgg cctctatgaa tcccaatata taattgggat    240
tcatagaggc cacctcgagc atgcatctag agggccctat tctatagtgt cacctaaatg    300
ctagagctcg ctgatcagcc tcgactgtgc cttctagttg ccagccatct gttgtttgcc    360 cctccccgt gccttccttg accctggaag gtgccactcc cactgtcctt tcctaataaa    420
aaaaaaaaaa aaaaaaaaaa                                                440

<210> SEQ ID NO 36
<211> LENGTH: 493
<212> TYPE: DNA
<213> ORGANISM: Artificial Sequence
<220> FEATURE:
<223> OTHER INFORMATION: Description of Artificial Sequence: Synthetic
      siRNA construct

<400> SEQUENCE: 36
```

-continued

```
gctaactaga gaacccactg cttactggct tatcgaaatt aatacgactc actatagggga      60 gacccaagct tggtaccgag ctcggatcct acagcagtgg agagcgatta tatataataa     120
tcgctctcca ctgctgtagg atccactagt aacggccgcc actacagcag tggagagcga     180
ttatatataa taatcgctct ccactgctgt aggtgtgctg gaattctgca gatatccatc     240
acactggcgg ccgctcgagg tggcctctat gaatcccaat atataattgg gattcataga     300
ggccacctcg agcatgcatc tagagggccc tattctatag tgtcacctaa atgctagagc     360
tcgctgatca gcctcgactg tgccttctag ttgccagcca tctgttgttt gcccctcccc     420
cgtgccttcc ttgaccctgg aaggtgccac tcccactgtc ctttcctaat aaaaaaaaaa     480
aaaaaaaaaa aaa                                                        493
```

<210> SEQ ID NO 37
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37

```
aaaaaaaaaa                                                             10
```

<210> SEQ ID NO 38
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38

```
aaaaaaaaaa aaaaaaaaaa aaaaaaaaaa aaaaaaaa                              39
```

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
caagcgtgtc agcgctgtag                                                  20
```

MULTICISTRONIC CONSTRUCTS WITH SIRNA TO INHIBIT TUMORS

This application is a continuation-in-part of International Application No. PCT/US2005/41709, filed Nov. 17, 2005, which claims priority to U.S. Ser. No. 60/629,659, filed Nov. 18, 2004.

STATEMENT OF GOVERNMENT SUPPORT

The government has rights in the disclosed invention due to partial support of NIH/NCI Grants: CA 85216, CA 75557, CA 76350, CA 92393, CA 95058, CA 116708 and NIH/NINDS Grant: NS 47699 and NS 57529.

BACKGROUND

Tumor progression involves modulation of tumor-cell adhesion during cell migration and degradation of the extracellular matrix (ECM) during tissue invasion. An intricate balance of proteases, their activators and their inhibitors, regulates both these processes during tumor invasion. Three classes of ECM-degrading proteinases are the serine proteinases, metalloproteases and cysteine proteinases. Urokinase plasminogen activator (uPA) initiates a cascade of proteases that can degrade most matrix and basement membrane components and interfere with cell-cell and cell-matrix interactions. uPA, bound to its cell surface receptor, urokinase plasminogen activator receptor (uPAR), is a participant of ECM degradation, as demonstrated by a several-fold increase in plasminogen activation. uPA also activates several growth factors after degradation of ECM components. Binding of uPA with its receptor uPAR activates downstream signaling molecules through a number of pathways, including the mitogen-activated protein kinases (MAPK) and signal transducer and activator of transcription (Stat) pathways.

Recent discovery of RNA interference (RNAi) has opened new avenues in cancer therapy. RNAi is a sequence-specific, post-transcriptional gene-silencing mechanism that is affected through double-stranded RNA molecules homologous to the sequence of the target gene.

RNA interference (RNAi) is a sequence-specific, post-transcriptional gene silencing mechanism, which is triggered by double-stranded RNA (dsRNA) and causes the degradation of mRNA with a sequence homologous to the dsRNA. RNAi depends upon the formation of double-strand RNA (dsRNA) whose antisense strand is complementary to the transcript of a targeted gene. Sequence-specific inhibition RNAi can also be induced in mammalian cells. In one implementation of RNAi, selective degradation of target mRNAs in mammalian cells was achieved by transfection with double-stranded, short interfering RNAs (siRNAs), leading to rapid and efficient degradation of the target. These siRNA were shown to avoid the well-documented, nonspecific effects triggered by longer double-stranded RNAs in mammalian cells.

Prostate cancer is the second most common malignancy in American men, with estimates of 230,110 new cases and approximately 30,000 deaths in 2004. As such, prostate cancer poses a major public health problem in the United States and worldwide. Currently, metastatic prostate cancer is incurable and ultimately claims the life of patients. A factor in the relative seriousness of prostate cancer is the invasiveness of the constituent tumor cells causing metastasis. The invasive nature of tumor cells is a characteristic for cancer metastasis. Tumor cell invasion and metastasis are complex processes with three prominent stages: adhesion of malignant (neoplastic) cells to the extracellular matrix, digestion of the matrix to release cells from the primary tumor mass, and migration of the tumor cells to secondary targets.

Glioblastoma multiforme (GBM) is a highly malignant primary central nervous system neoplasm, which is highly refractory to therapy. One property that makes glioblastoma resistant to treatment is the tendency of the tumor cells to invade normal brain tissue. Therapy which affects normal brain tissue, is not acceptable. Invasiveness is thus considered to be a major determinant of the malignant behavior of human gliomas. Diffuse single-cell invasion, which occurs in all glial tumors regardless of histological grade, is defined as a translocation of neoplastic cells through host cellular and ECM barriers. Malignant gliomas express higher levels of uPA, uPAR and MMP-9 compared with normal brain tissue.

MMPs enhance tumor cell invasion by degrading extracellular matrix proteins, activating signal transduction cascades that promote motility and activating growth factors, such as transforming growth factor $\beta$, that are implicated in GBM motility. Expression of the gelatinases MMP-2 and MMP-9 correlates with the invasive and metastatic potentials of various cancers, including gliomas. MMP-9 levels were highly correlated with the histological grade of glioma malignancy. MMP-9 is relevant in endothelial cell morphogenesis and capillary formation in glial/endothelial co-cultures in vitro. MMPs also regulate tumor angiogenesis and might be required for the 'angiogenic switch' that occurs during tumor neovascularization.

The proteolytic activity of cathepsin B, a cysteine protease, involves the direct degradation of ECM proteins, including fibronectin, types I and IV collagen and laminin. Cathepsin B also indirectly activates other enzymes involved in the proteolytic cascade that mediates ECM degradation, including metalloproteinases and both soluble and receptor-bound urokinase plasminogen activator (uPA). In addition, cathepsin B has been suggested to increase MMP activity by inactivating tissue inhibitors of matrix metalloproteinases (TIMPs). Cathepsin B, therefore, could be an important upstream regulator in the activation of pro-uPA/plasminogen and pro-MMPs. Cathepsin B has also been shown to contribute to apoptosis by causing cytochrome c release and caspase 9 and 3 activation (key events in the mitochondrial pathway of apoptosis). Increase in cathepsin B expression and reductions in its inhibitor levels were associated with tumor growth, vascularization, invasion and metastasis in various cancers.

siRNA molecules that target a plurality of genes implicated in tumors are desired to develop therapeutic compositions.

SUMMARY

Multicistronic short interfering RNA constructs include two or more self-complementary sequences targeting a plurality of genes encoding for example, a sequence encoding human urokinase-type plasminogen activator receptor (uPAR), a human urokinase-type plasminogen activator (uPA), a human matrix metalloprotease 9 (MMP-9) and cathepsin B (CB). The constructs are used to inhibit tumor progression.

A multicistronic short interfering RNA construct includes at least a first and a second self-complementary sequence used to inhibit tumors. In an embodiment the first self-complementary includes a nucleotide sequence of human urokinase-type plasminogen activator receptor (uPAR) and the second self-complementary sequence includes a nucleotide sequence of human urokinase-type plasminogen activator (uPA).

A self complementary sequence of uPA is TGAGAGC-CCTGCTGGCGCGCC-loop-GGCGCGCCAG-

CAGGGCTCTCA (SEQ ID NO: 1) and the self complementary sequence of uPAR is CTACAGCAGTGGAGAGCGATT-loop-AATCGCTCTC-CACTGCTGTAG (SEQ ID NO: 2). The loop comprises about 9 nucleotides that are GC deficient. A suitable loop sequence a nucleotide sequence ATATATAAT, wherein "suitable" means operative. The self complementary sequences of uPAR and uPA are generally separated by an intervening sequence of length of about 22-35 base pairs. For example, an intervening sequence is AGCT TGGTACCGAG CTCG GATC (SEQ ID NO: 3). The self complementary sequences of uPAR and uPA in the multicistronic construct are operably linked to a promoter, usually a single one. The multicistronic construct of uPA and uPAR is a circular nucleic acid or a linear nucleic acid.

A multicistronic short interfering RNA construct includes at least a first and a second self-complementary sequence to inhibit tumors. In an embodiment, the first self-complementary includes a nucleotide sequence of urokinase-type plasminogen activator receptor (uPAR) and the second self-complementary sequence comprises a nucleotide sequence of matrix metalloprotease 9 (MMP-9). A self complementary sequence of uPAR is CTACAGCAGTGGAGAGCGATT-loop-AATCGCTCTCCACTGCTGTAG (SEQ ID NO: 2) and a self complementary sequence of MMP-9 is CAAGTG-GCACCACCACAACAA-loop-TTGTTGTGGTGGTGC-CACTTG (SEQ ID NO: 4) and the loop includes about 9 nucleotides that are GC deficient. A suitable loop sequence includes a nucleotide sequence ATATATAAT. The self complementary sequences of uPAR and MMP-9 are generally separated by an intervening sequence of length of about 22-35 base pairs. An intervening sequence is GATCCA CTAGTAACGG CCGCCAGTGT GCTGG AATT (SEQ ID NO: 5). The uPAR-MMP-9 construct is a circular or a linear nucleic acid.

A multicistronic short interfering RNA construct includes at least a first and a second self-complementary sequence used to inhibit tumors. In an embodiment, the first self-complementary includes a nucleotide sequence of urokinase-type plasminogen activator receptor (uPAR) and the second self-complementary sequence comprises a nucleotide sequence of cathepsin B (CB). A self complementary sequence of uPAR is CTACAGCAGTGGAGAGCGATT-loop-AATCGCTCTCCACTGCTGTAG (SEQ ID NO: 2) and a self complementary sequence of CB is CAAGTGGCAC-CACCACAACA-loop-TGTTGTGGTGGTGCCACTTG (SEQ ID NO: 6) and the loop includes about 9 nucleotides that are GC deficient. A suitable loop sequence includes a nucleotide sequence ATATATAAT. The self complementary sequences of uPAR and CB are generally separated by an intervening sequence of length of about 22-68 base pairs. An intervening sequence is GATCCA CTAGTAACGG CCGCCAGTGT GCTGG AATTC TGCAGATATC CATCA-CACTG GCGGCCGC TCGA (SEQ ID NO: 7). The uPAR-CB construct is a circular or a linear nucleic acid.

A multicistronic short interfering RNA construct includes at least a first, a second and a third self-complementary sequence to inhibit tumors. The first self-complementary includes a nucleotide sequence of urokinase-type plasminogen activator receptor (uPAR), the second self-complementary includes a nucleotide sequence of urokinase-type plasminogen activator (uPA), and the third self-complementary includes a nucleotide sequence of matrix metalloprotease 9 (MMP-9). A self complementary sequence of uPAR is CTA-CAGCAGTGGAGAGCGATT-loop-AATCGCTCTC-CACTGCTGTAG (SEQ ID NO: 2); a self complementary sequence of uPA is TGAGAGCCCTGCTGGCGCGCC-loop-GGCGCGCCAGCAGGGCTCTCA (SEQ ID NO: 1) and a self-complementary sequence of MMP-9 is CAAGTG-GCACCACCACAACAA-loop-TTGTTGTGGTGGTGC-CACTTG (SEQ ID NO: 4). The loop includes about 9 nucleotides that are GC deficient. The loop sequence includes a nucleotide sequence ATATATAAT. The self complementary sequences of uPAR and MMP-9 are generally separated by an intervening sequence of length of about 22-68 base pairs. An intervening sequence is GATCCA CTAGTAACGG CCGCCAGTGT GCTGG AATTC TGCAGATATC CATCA-CACTG GCGGCCGC TCGA (SEQ ID NO: 7). The uPA-uPAR region is separated by about 22-35 bases that includes a nucleotide sequence of AGCT TGGTACCGAG CTCG GATC (SEQ ID NO: 3). The uPA-uPAR-MMP-9 construct is a linear or a circular nucleic acid.

A multicistronic short interfering RNA construct includes at least a first and a second self-complementary sequence to inhibit tumors. The first self-complementary includes a nucleotide sequence of matrix metalloprotease 9 (MMP-9) and the second self-complementary sequence comprises a nucleotide sequence of cathepsin B (CB). A self-complementary sequence of MMP-9 is CAAGTGGCACCACCACAA-CAA-loop-TTGTTGTGGTGGTGCCACTTG (SEQ ID NO: 4) and a self complementary sequence of CB is CAAGTG-GCACCACCACAACA-loop-TGTTGTGGTGGTGC-CACTTG (SEQ ID NO: 6) and the loop includes about 9 nucleotides that are GC deficient. The loop sequence includes a nucleotide sequence ATATATAAT. The self complementary sequences of MMP-9 and CB are generally separated by an intervening sequence of length of about 22-37 base pairs. An intervening sequence is AATTCTGCAGATATCCATCA-CACTGGCGGCCGCTCGA (SEQ ID NO: 8). The MMP-9-CB construct is a circular or a linear nucleic acid.

A method of inhibiting tumors, the method includes the steps of:
(a) administering a short interfering RNA multicistronic construct; and
(b) reducing expression of a plurality of genes expressed in tumors, thereby inhibiting tumors from forming or growing, and regressing tumors that already exist A method of using a short forming or interfering RNA multicistronic construct that targets, for example, urokinase-type plasminogen activator receptor (uPAR) and urokinase-type plasminogen activator (uPA), thereby reducing the expression of uPAR and uPA and inhibiting tumors. The short interfering RNA multicistronic construct includes a nucleotide sequence tGagagccctgctggcgcgcc-loop-ggcgcgccag-cagggctctca-intervening sequence-cTacagcagtggagagcgatt-loop-aatcgctctccactgctgtag (SEQ ID NOS 1 and 2, respectively). Another term for "intervening sequence" is a "spacer". A tumor is inhibited by reducing at least one of tumor cell proliferation, tumor cell invasion, tumor cell migration and angiogenesis. Tumors include prostate cancer, glioma, breast cancer, and melanoma. The construct is delivered through a viral vector or administered through direct delivery or by any suitable method known to those of skill in the art.

A method of using a short interfering RNA multicistronic construct may also target urokinase-type plasminogen activator receptor (uPAR) and matrix metalloprotease 9 (MMP-9), thereby reducing the expression of uPAR and MMP-9 and inhibiting tumors. The short interfering RNA multicistronic construct includes a nucleotide sequence cTacagcagtg-gagagcgatt-loop-aatcgctctccactgctgtag-spacer-Caagtggcac-caccacaacaa-loop-ttgttgtggtggtgccacttg (SEQ ID NOS 2 and 4, respectively). The tumor is inhibited by reducing at least one of tumor cell proliferation, tumor cell invasion, tumor cell migration and angiogenesis. Tumors include prostate cancer, glioma, breast cancer, and melanoma. The construct is delivered through a viral vector or administered through direct delivery or by any suitable method known to those of skill in the art.

A method of inhibiting tumors, includes the steps of:
(a) administering a multicistronic construct targeted to at least one of uPA, uPAR, MMP-9 and CB; and
(b) reducing the expression of at least one of uPA, uPAR, MMP-9 and CB, thereby inhibiting tumors.

A short interfering RNA molecule includes RNA molecules targeted to:

1. urokinase-type plasminogen activator receptor (uPAR) and matrix metalloprotease 9 (MMP-9), that includes a nucleic acid sequence CUACAGCAGUGGAGAGCGAUU-loop-AAUCGCUCUCCACUGCUGUAG-spacer-CAAGUG-GCACCACCACAACAA-loop-UUGUUGUGGUG-GUGCCACUUG (SEQ ID NOS 9 and 10, respectively);
2. urokinase-type plasminogen activator receptor (uPAR) and urokinase-type plasminogen activator (uPA), that includes a nucleic acid sequence UGAGAGCCCUGCUG-GCGCGCC-loop-GGCGCGCCAGCAGGGCUCUCA-spacer-CUACAGCAGUGGAGAGCGAUU-loop-AAUCGCUCUCCACUGCUGUAG (SEQ ID NOS 11 and 9, respectively);
3. urokinase-type plasminogen activator receptor (uPAR) and cathepsin B (CB), that includes a nucleic acid sequence of CUACAGCAGUGGAGAGCGAUU-loop-AAUCGCU-CUCCACUGCUGUAG-spacer-CAAGUGGCACCAC-CACAACA-loop-UGUUGUGGUGGUGCCACUUG (SEQ ID NOS 9 and 12, respectively);
4. urokinase-type plasminogen activator receptor (uPAR), urokinase-type plasminogen activator (uPA), and matrix metalloprotease 9 (MMP-9), that includes nucleic acid sequence of CUACAGCAGUGGAGAGCGAUU-loop-AAUCGCUCUCCACUGCUGUAG-spacer-UGAGAGCCCUGCUGGCGCGCC-loop-GGCGCGC-CAGCAGGGCUCUCA-spacer-CAAGUGGCACCACCACAACAA-loop-UUGUUGUGGUGGUGCCACUUG (SEQ ID NOS 9, 11 and 10, respectively); and
5. matrix metalloprotease 9 (MMP-9) and cathepsin B (CB) that includes a nucleic acid sequence of CAAGUGGCAC-CACCACAACAA-loop-UUGUUGUGGUGGUGC-CACUUG-spacer-CAAGUGGCACCACCACAACA-loop-UGUUGUGGUGGUGCCACUUG (SEQ ID NOS 10 and 12, respectively).

A recombinant cell transformed with a multicistronic construct of uPA-uPAR or uPAR-MMP-9 or uPAR-CB, or uPA-uPAR-MMP-9 or MMP-9-CB is disclosed herein.

A recombinant virus transformed with a multicistronic construct of uPA-uPAR or uPAR-MMP-9 or uPAR-CB, or uPA-uPAR-MMP-9 or MMP-9-CB is disclosed herein.

ABBREVIATIONS uPA means urokinase-type plasminogen activator; uPAR means urokinase-type plasminogen activator receptor; MMP-9 means matrix metalloprotease 9; CB means cathepsin B; CMV means cytomegalovirus; SV40 means simian virus type 40; GFP means green fluorescent protein; ECM means extracellular matrix; siRNA means short interfering RNA; shRNA means short hairpin RNA; RNAi means RNA interference.

Comparison of the in vitro invasive potentials of prostate cancer cell lines (C). Invasion assays were performed in 12-well transwell chambers containing polycarbonate filters with 12 μm pores coated with matrigel. Cells that had passed to the undersurface of the filters were stained and photographs were taken under microscope at a 200× magnification (C). Cells invading through the matrigel were counted under a microscope in three random fields at a 200× magnification. Each bar represents the mean±SD of three fields where significant differences from low or non-metastatic LNCaP cells, which exhibited undetectable uPA and uPAR protein expression, are represented by asterisks * (P<0.05) (D).

FIG. 2 shows RNAi knockdown of uPA and uPAR expression in the prostate cancer cell line PC3. Schematic representation of the sh-uPAuPAR plasmid construct (A (poly A tail as shown in FIG. 2A is SEQ ID NO: 37)). The construct consists of a human CMV promoter and homologous sequences targeted against uPA and uPAR. Following expression, the strong CMV promoter drives the formation of short hairpin molecules specific for uPA and uPAR. The bovine growth hormone (BGH) poly adenylation sequence serves as a RNA pol II-based CMV promoter termination signal. Dicer/Drosha processes the shRNA-specific for uPA and uPAR and the resulting siRNA molecules interact with the target genes uPA and uPAR. This interaction results in the simultaneous knockdown of uPA and uPAR gene expression. Semi-quantitative reverse transcription-PCR of RNA extracted from shRNA-transfected PC3 cells (B). The glyceraldehyde-3-phosphate dehydrogenase (GAPDH) mRNA was co-amplified as a control. Immunoblotting of total protein lysates extracted from shRNA-transfected PC3 cells (C). Both uPA and uPAR bands are present in mock, EV and SV-transfected cells. Accordingly, each gene-specific shRNA lane shows a significant decrease of the appropriate band. GAPDH was included as a loading control. uPA and uPAR protein expression levels were also detected using indirect immunofluorescence in PC3 cells. PC3 cells transfected with the EV, SV and mock cells stained positive for immunofluorescent detection of uPA (FITC) and uPAR (Texas Red) (D). Gene-specific shRNA-transfected cells substantially changed the cell staining profiles of uPA and uPAR as compared to EV/SV-transfected and mock cells. Nuclear counterstaining was obtained with DAPI. (Results are representative of at least three separate experiments.)

Figure 3:
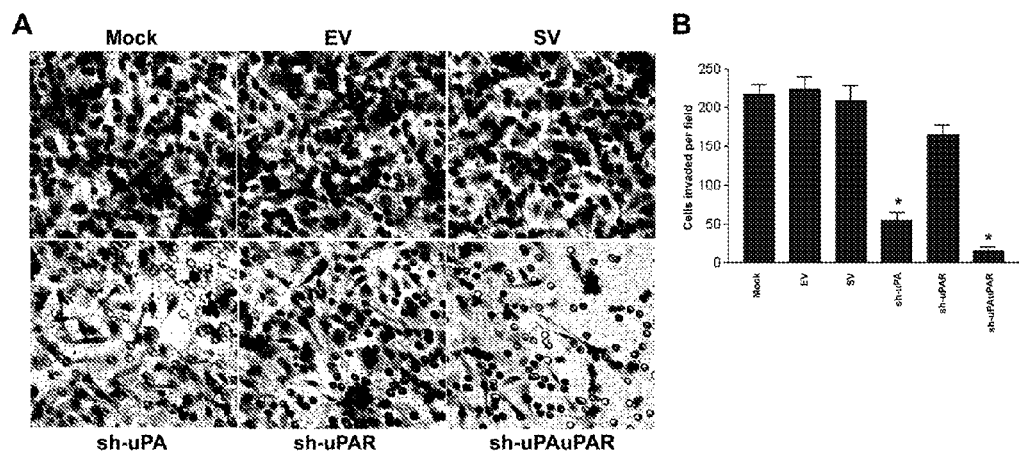

FIG. 3 shows that RNAi knockdown of uPA and uPAR expression inhibits the invasive potential of PC3 cells. The invasive potential of mock cells and cells transfected with the indicated shRNA plasmids were examined by Matrigel invasion assay (visual field representative of one experiment) (A). Invasion assays performed as described herein (see FIG. 1C). Representative number of invading cells through the matrigel was counted under microscope in three random fields at 200× (B). Each bar represents the mean SD of three fields counted. Significant difference from controls (i.e., mock or scrambled vector-transfected cells) is indicated by asterisks * ($P<0.05$).

FIG. 4 illustrates that RNAi knockdown of uPA and uPAR expression inhibits cell proliferation and induces apoptosis in PC3 cells. Viability of PC3 cells transfected with either gene-specific shRNA plasmids or controls (mock or EV/SV-transfected cells) was revealed by 3-(4,5-dimethylthiazol-2-yl)-2, 5-diphenyltetrazolium bromide (MTT) assay (A). Each bar represents triplicate analyses of mean SD where significant difference from controls is represented by an asterisk * ($P<0.05$). Representative immunoblots show changes in pro-apoptotic gene expression in uPA-uPAR knockdown PC3 cells (B). GAPDH was used as a loading control. Caspase activation was detected in situ with fluorescence labeling (lower panel) using FAM-VAD-FAK, a cell permeable caspase inhibitor that binds to activated caspases (C). Nuclear staining was performed with DAPI (upper panel). A significant number of cells transfected with sh-uPAuPAR displayed green fluorescence. Bar diagram showing quantitative data of DAPI/FMK-VAD-FAK labeled cells ratio from three random fields under a confocal microscope (D). The ratio of DAPI to FMK-VAD-FAK was significantly increased in cells transfected with sh-uPAuPAR. Significant differences from mock or EV/SV-transfected cells are indicated by asterisks * ($P<0.05$). DNA laddering was observed in cells transfected with uPA-uPAR shRNA and cells treated with actinomycin D (ActD, 0.2 g/ml) (E). An agarose gel was stained with ethidium bromide and photographed under UV light. DNA markers were electrophoresed as a kilobase pair reference with standard bands of 2.0, 1.5, 1.0, 0.75 and 0.5 kb (lane M).

Figure 5:
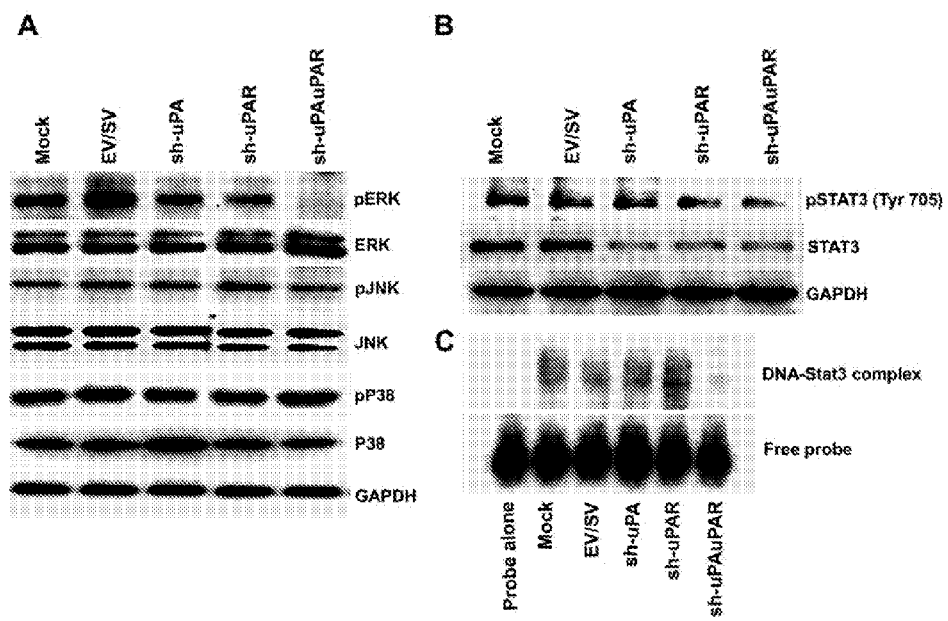

FIG. 5 demonstrates that RNAi knockdown of uPA and uPAR expression inhibits downstream signaling in PC3 cells. Immunoblot analysis of total and phosphorylated forms of extracellular signal-regulated kinase (ERK), p38 and JNK in mock and shRNA-transfected cells (A). PC3 cells transfected with mock, EV, SV, sh-uPA, sh-uPAR and sh-uPAuPAR were lysed 72 h later and subjected to SDS-PAGE followed by immunoblotting with total and phosphorylated forms of ERK, p38 and JNK antibodies. GAPDH antibodies were used to verify that similar amounts of protein were loaded in each lane. Immunoblot analysis of Stat 3 protein in mock and shRNA-transfected cells (B). Equal amounts of protein were loaded and immunoblotting was carried out using phospho-specific Stat 3 antibodies against tyrosine 705 and antibodies against a non-phosphorylated form of Stat 3. GAPDH was included as a loading control. The electrophoretic mobility shift assay of mock and shRNA-transfected cells (C). Protein-DNA complexes were separated on a 6% polyacrylamide gel, dried and autoradiographed. Shown above is specific DNA binding activity of nuclear extracts prepared from the indicated shRNA-transfected cells. Position of free probe is shown.

Figure 6:
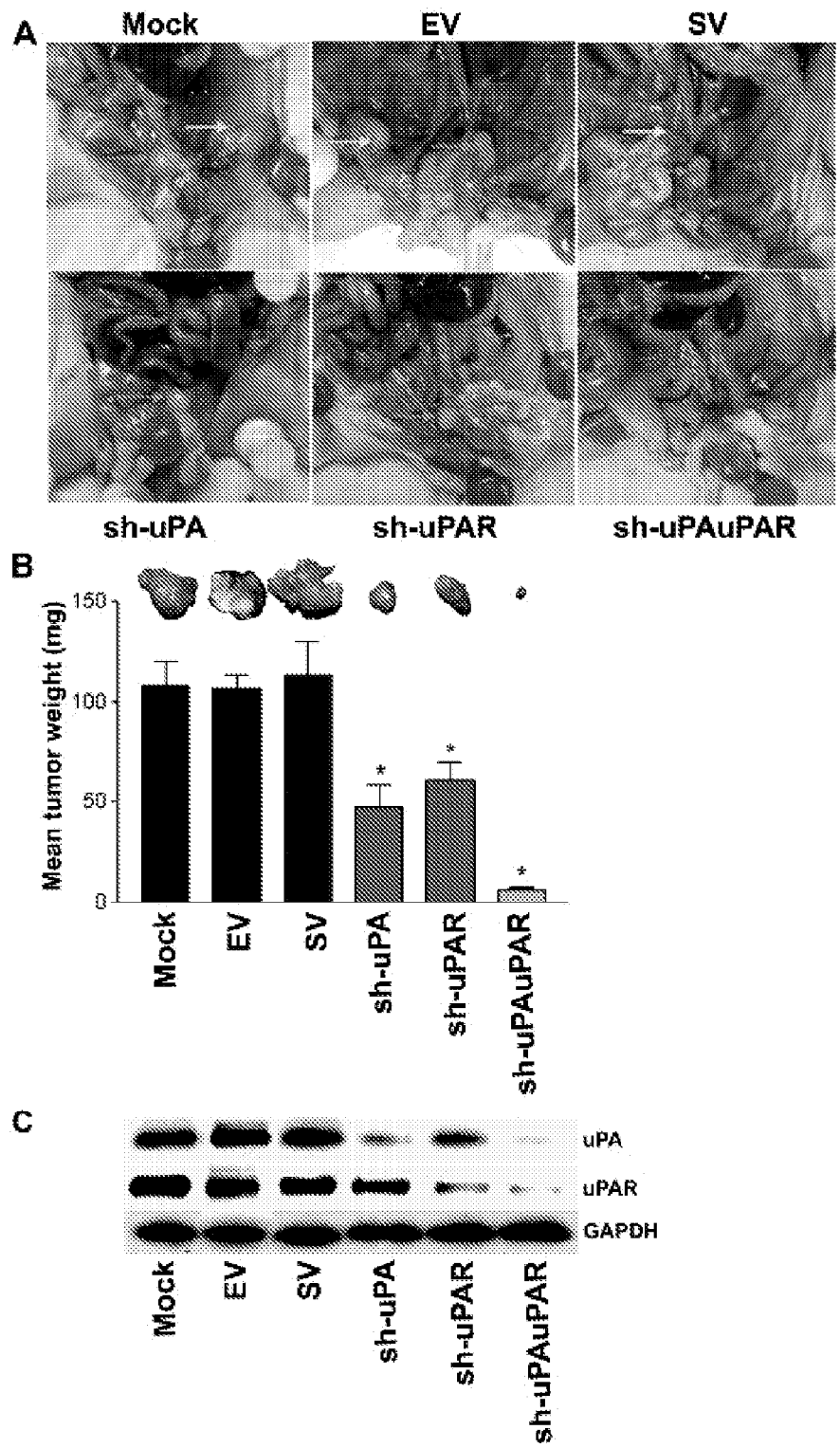

FIG. 6 shows that RNAi knockdown of uPA-uPAR expression abrogates tumor growth in an orthotopic mouse prostate tumor model. Representative in situ pictures from each treatment group of mice bearing orthotopic PC3 tumors (A). The primary prostate tumor is labeled with dashed arrows and solid arrows indicate the position of metastases. PC3 cells were transplanted intraprostatically into nude mice and established PC3 prostate tumors were treated with shRNA-specific for uPA, uPAR and uPAuPAR. After 4 weeks of the treatment of these constructs, the mice were sacrificed and evaluated for primary prostate tumor growth and metastases visually. A comparison of dissected prostate tumors from each shRNA treatment group (B). Each bar represents the mean tumor weight SD of six animals per group. Significant differences from control groups (i.e., mock or EV/SV-treated) are represented by asterisks * ($P<0.05$). Protein samples extracted from PC3 prostate tumors of six animals per group were analyzed using immunoblotting for uPA and uPAR expression levels (C). GAPDH was included as a loading control.

Figure 7:
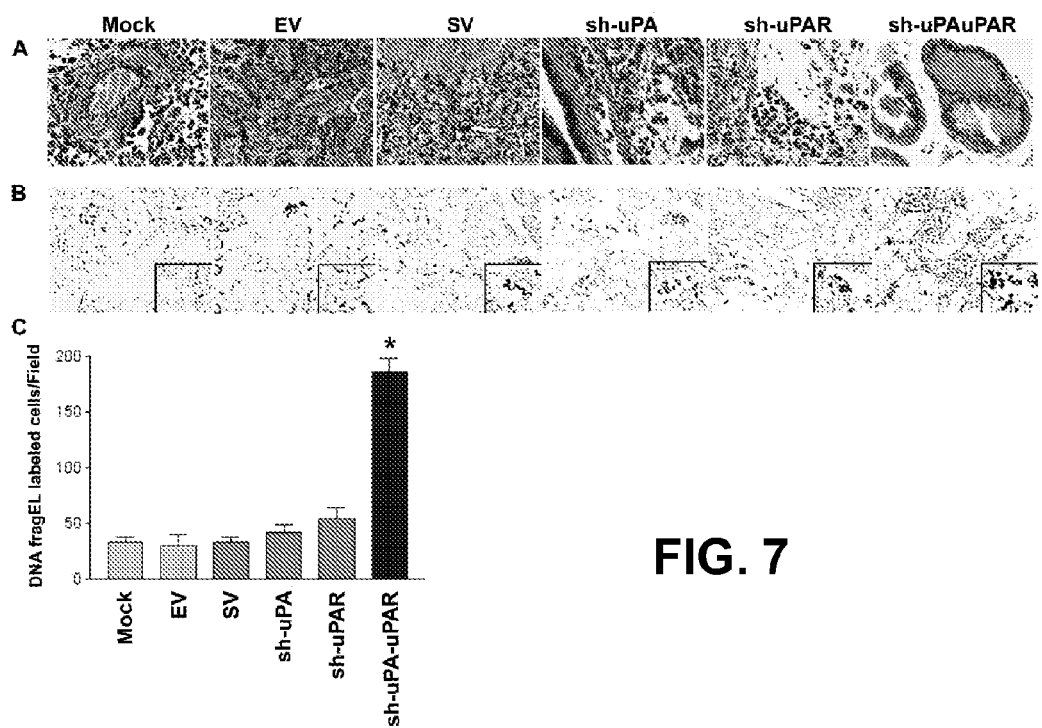

FIG. 7 demonstrates that RNAi knockdown of uPA and uPAR expression simultaneously abrogates tumor growth in an orthotopic mouse prostate tumor model. Representative in situ pictures from each treatment group of mice bearing orthotopic PC3 tumors (A). The primary prostate tumor is labeled with dashed arrows and solid arrows indicate the position of metastases. PC3 cells were transplanted intraprostatically into nude mice and established PC3 prostate tumors were coinjected with both the sh-uPA and sh-uPAR vectors. After 4 weeks of the treatment of these constructs, the mice were sacrificed and evaluated for primary prostate tumor growth and metastases visually. A comparison of dissected prostate tumors from each shRNA treatment group (B). Each bar represents the mean tumor weight SD of six animals per group. Significant differences from control groups (i.e., mock or EV/SV-treated) are represented by asterisks * ($P<0.05$). Protein samples extracted from PC3 prostate tumors of six animals per group were analyzed using immunoblotting for uPA and uPAR expression levels (C). GAPDH was included as a loading control. Representative hematoxylin and eosin sections of the orthotopic PC3 prostate mouse tumors (D). Primary prostate tumors were harvested from each treatment group at the conclusion of the experiment. Tumors were fixed in formalin and embedded in paraffin. Tissue sections (5 m) were prepared and stained with H&E for histopathological analysis. DNA fragEL staining of microdissected paraffin sections from established prostate tumors from the indicated treatment groups (E). DNA fragment end labeling assays were performed. Results are shown at a 40× magnification except for the box, which is at a 200× magnification. Bar diagram showing quantitative data of DNA fragEL-labeled cells from six random fields per treatment group (F). Significant differences from control groups are indicated by asterisks * ($P<0.05$).

Figure 8:
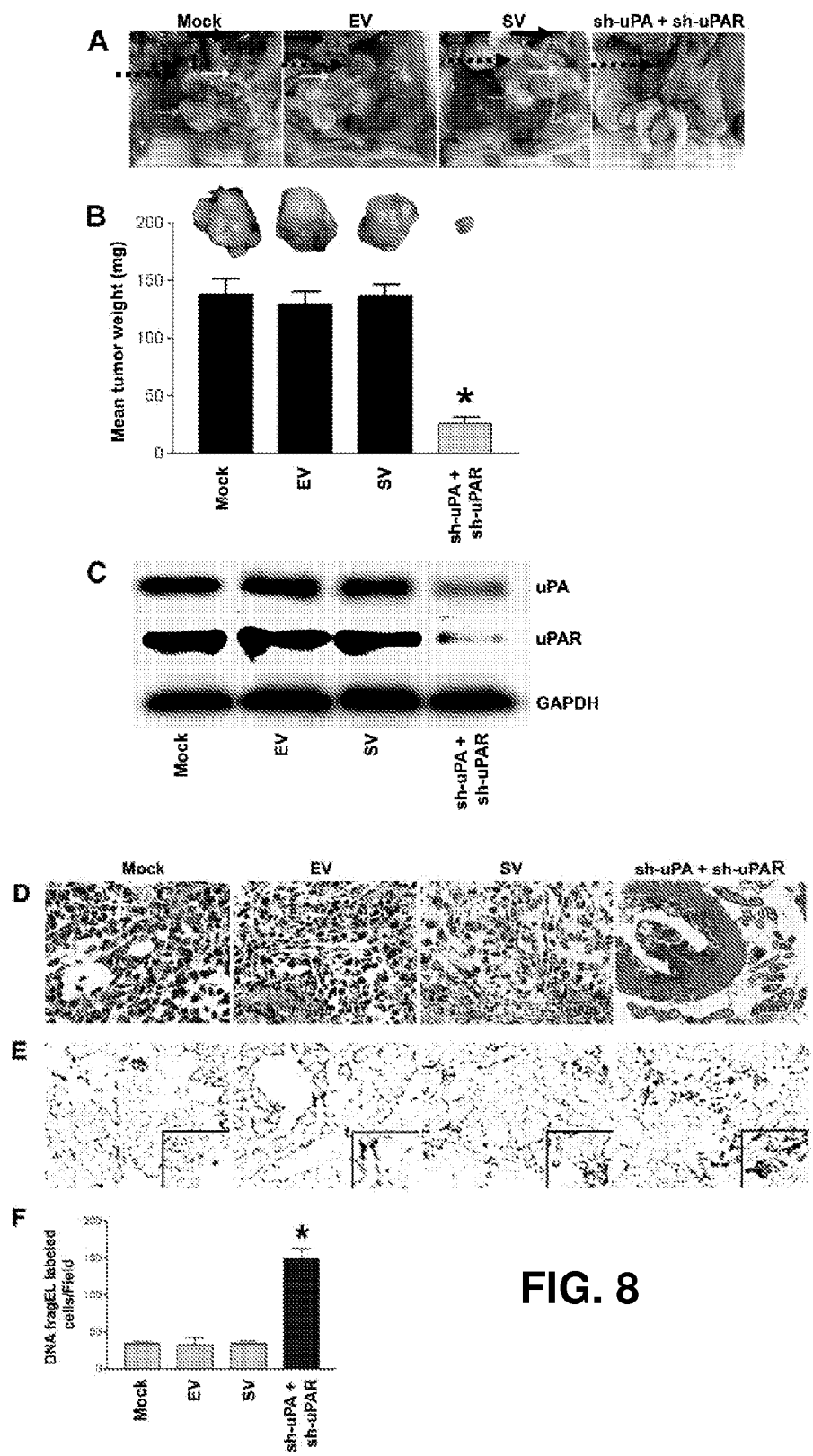

FIG. 8 shows a schematic representation of siRNA expression for uPAR and MMP-9 from pUM vector. pcDNA 3 plasmid constructs were developed having two complementary inverted repeats driven by a CMV promoter directed against uPAR and MMP-9. The CMV promoter drives the formation of a dual hairpin structure which, in turn, is processed by the double strand RNA recognizing enzyme DICER to form viable siRNA molecules. Stability of the dual hairpin molecule is ensured because of the secondary structure of the molecule which is reminiscent of an mRNA molecule having a poly A tail driven by a bovine growth hormone (BGH) poly-a signal sequence (poly A tail as shown in FIG. 8 is SEQ ID NO: 37).

Figure 9:
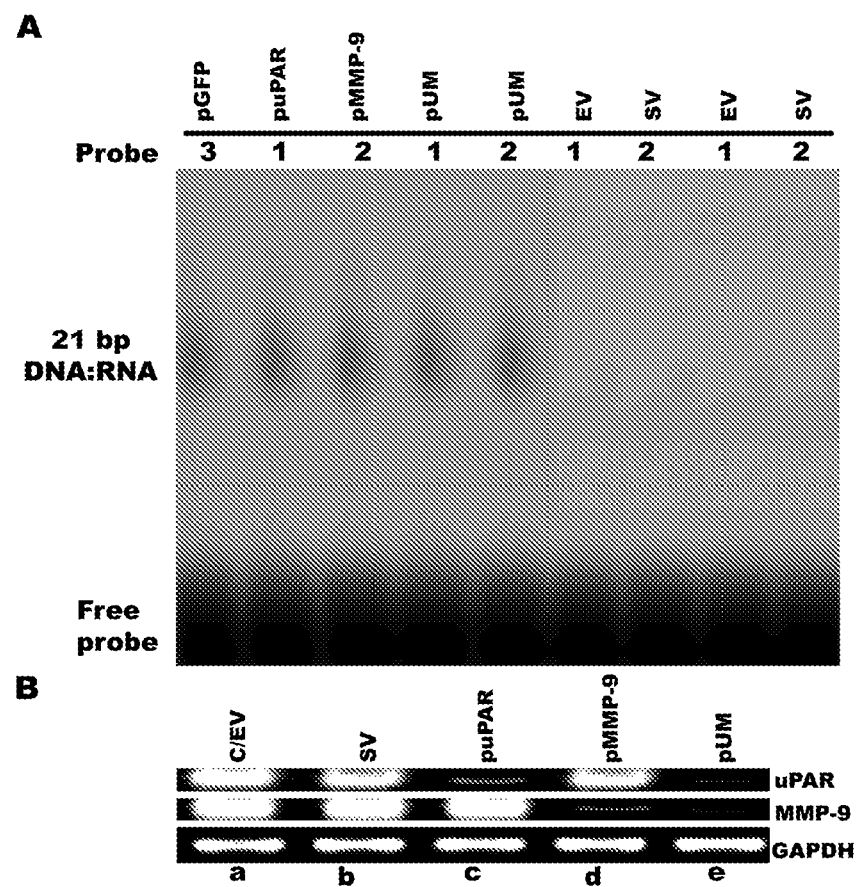

FIG. 9 illustrates whether long hairpin (hp) RNA are processed to siRNA, molecules were transfected in SNB19 cells with control/EV, SV, puPAR, pMMP-9 and pUM; cells were also transfected with an unrelated construct targeting GFP in non-GFP cells to determine the processing of appropriate siRNA molecules. Small RNA molecules fractionated on a 2% agarose gel were allowed to hybridize with appropriate DIG labeled sense oligo in the presence of 6×SSC. The resulting hybrid solution was run on a 15% polyacrylamide gel and electroblotted onto a nylon membrane. The membrane was processed to visualize the 21 bp DNA:RNA hybrid as per manufacturers' instructions. The probes used are respresented as numbers (see Table 1), 1-suPAR, 2-sMMP-9 and 3-sGFP (FIG. 9A). SNB19 cells were transfected with control/EV (lane a), SV (lane b), puPAR (lane c), pMMP-9 (lane d) and pUM (lane e) as per standard protocols known to those with skill in the art. 72 h later, total RNA was isolated and first strand cDNA was synthesized using a cDNA synthesis kit (Invitrogen) (FIG. 9B). PCR reaction was set up using the first strand cDNA as the template for uPAR and MMP-9; PCR for GAPDH was also set up to serve as loading control (see Table 1).

FIG. 10 characterizes Western blot analysis for uPAR and gelatin zymography for MMP-9. SNB19 cells were transfected with mock, an empty/scrambled vector and a vector encoding single or bicistronic siRNA for uPAR and MMP-9 (puPAR, pMMP-9, pUM). (A) Western blot analysis of uPAR protein expression in cell lysates from SNB19 cells transfected with EV/SV, puPAR, pMMP-9 and pUM. Western blot analysis was performed using an antibody specific for uPAR. GAPDH was simultaneously immuno-detected to verify the loading of similar amounts of cell lysates. (B) Conditioned media containing equal amounts of protein (20 μg) from transfected cells from EV/SV, puPAR, pMMP-9 and pUM was mixed with Laemmli sample buffer and run on 10% SDS-PAGE gels containing 0.1% gelatin to determine MMP-9 activity by gelatin zymography.

Figure 11:
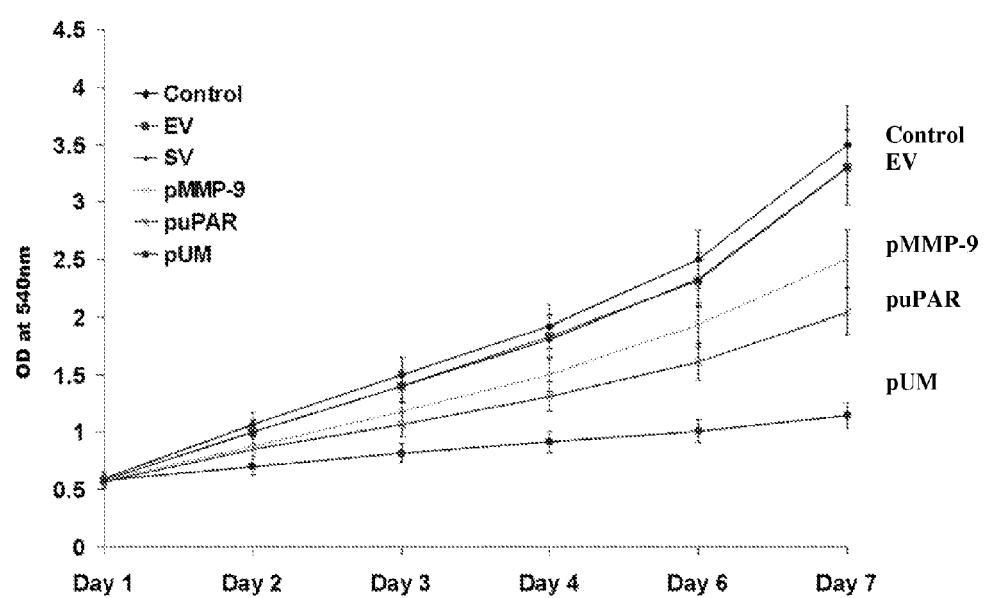

FIG. 11 demonstrates that RNAi-mediated downregulation of uPAR and MMP-9 reduces SNB19 glioma cell proliferation. Briefly $5 \times 10^4$ SNB19 cells transfected with EV/SV, puPAR, pMMP-9 and pCM were seeded in VN-coated 96-well microplates under serum-free conditions. The number of viable cells was assessed by MTT assay.

Figure 12:
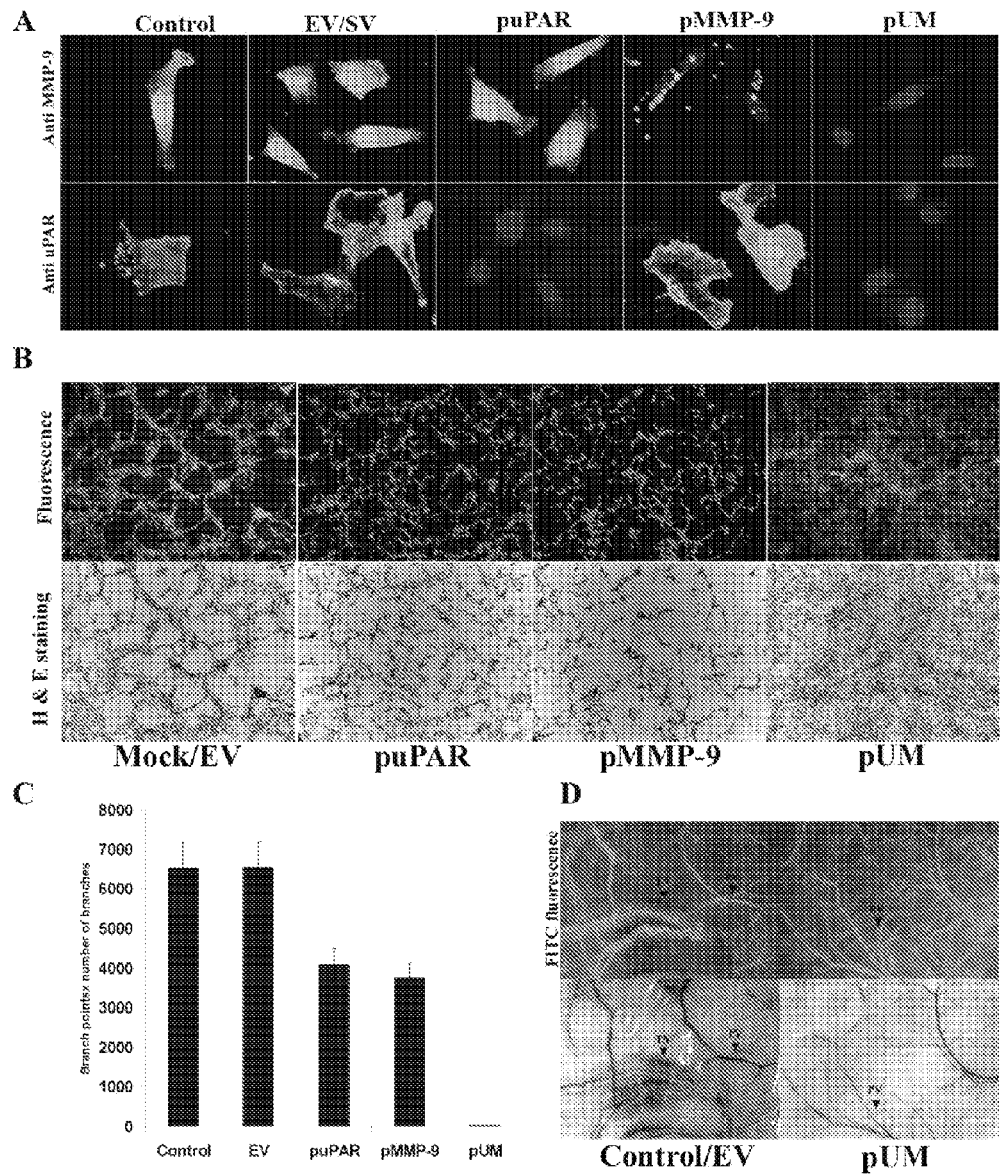

FIG. 12 illustrates that RNAi decreased uPAR and MMP-9 levels as shown by immunohistochemical analysis and tumor-induced angiogenesis. (A) SNB19 cells were transfected with EV, SV, puPAR, pMMP-9 and pUM. Control or un-transfected cells were also used. 72 h after transfection, the cells were fixed and processed to visualize uPAR and MMP-9 expression in vivo. The cells were mounted using mounting media with DAPI to visualize the nucleus. (B) SNB19 cells ($2 \times 10^4$) were seeded in 8-well chamber slides and transfected with mock EV, puPAR, pMMP-9 and pUM. After 24 h incubation, the medium was removed and the cells were co-cultured with $4 \times 10^4$ human microvascular dermal endothelial cells. After 72 h, endothelial cells were probed with antibody for factor VIII antigen or H&E staining and examined under a confocal scanning laser microscope. (C) Quantification of angiogenesis in co-cultures transfected with mock EV, puPAR, pMMP-9 and pUM vector or pUM vector. Values are mean±S.D. from three different experiments. Inhibition of tumor angiogenesis in pUM vector by mouse dorsal window assay (D). PV, pre-existing vasculature, TN, tumor induces vasculature.

Figure 13:
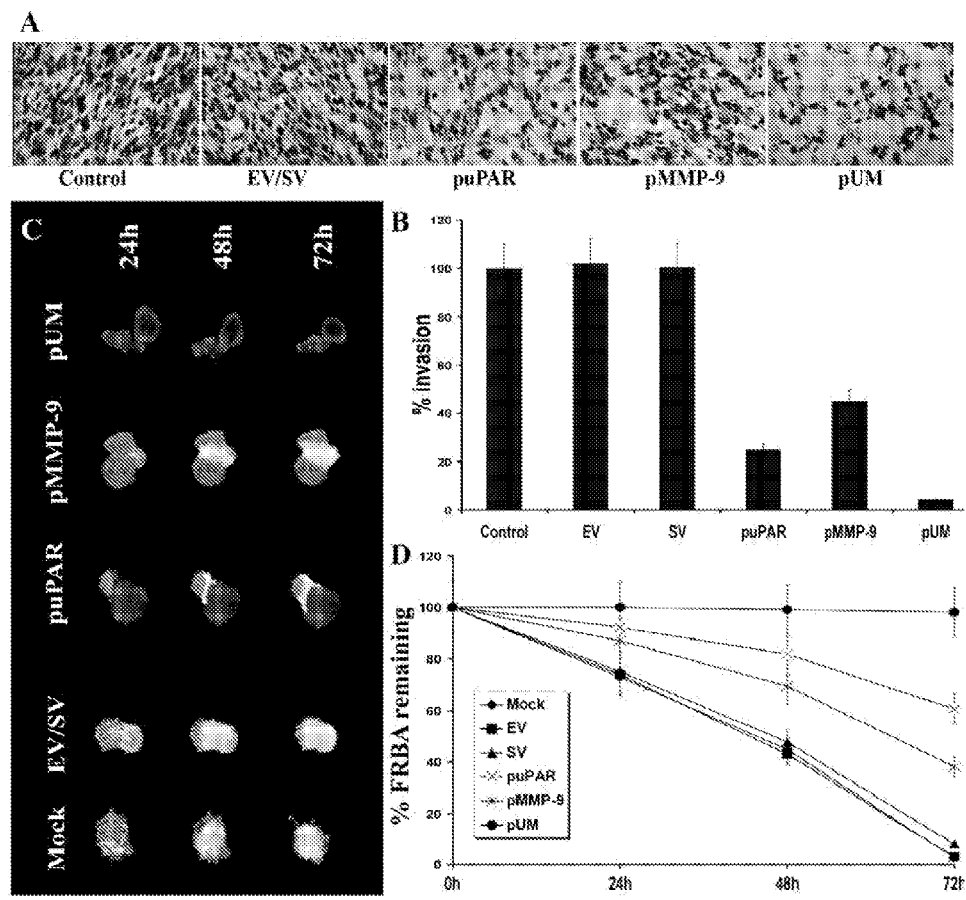

FIG. 13 demonstrates that siRNA for uPAR and MMP-9 inhibits invasion of SNB19 cells. SNB19 cells ($1 \times 10^6$) transfected with EV/SV, puPAR, pMMP-9 and pUM were allowed to migrate through Matrigel-coated transwell inserts (8-μm pores) for 24 h. The cells that invaded through the Matrigel-coated inserts were stained, counted and photographed under a light microscope at 20× magnification. (A) The percentage of invasion was quantified. Values are mean±S.D. from five different experiments (P<0.001). SNB19 cells spheroids (fluorescence) of 100-200 μm in diameter were selected, transfected with EV/SV, puPAR, puMMP-9 and pUM and co-cultured with fetal rat brain aggregates (green fluorescence). Progressive destruction of fetal rat brain aggregates and invasion of SNB19 cells was observed for 72 h using confocal laser scanning microscopy. (C). The remaining volumes of the brain aggregates or tumor spheroids at 24, 48 and 72 h were quantitated using image analysis software (D).

FIG. 14 analyzes RNAi-mediated regression of pre-established intracerebral at tumor growth. SNB19-GFP glioblastoma cells were injected intracerebrally ($2 \times 10^6$ cells in 10 μl phosphate buffer saline) into nude mice. After 10 days, mock EV, puPAR, pMMP-9 and pUM (150 μg of each vector were injected into the brain using Alzet mini pumps at the rate of 0.25 μl/h (eight mice in each group). Photomicrographed tumor sections were examined for GFP fluorescence (A) and subsequently stained with hematoxylin and eosin (B). Semiquantitation of tumor volume in mock EV, puPAR, pMMP-9 and pUM vector treated groups after 4-6 weeks after intracranial injection of these cells (C). Data shown are ±S.D. values from eight animals from each group. In other set of experiments, 10 days after intracerebral injection of SNB 19 GFP cells, pUM vector was injected intraperitoneally twice at an interval of 3 days and the animals were sacrificed after 4 months.

Figure 15:
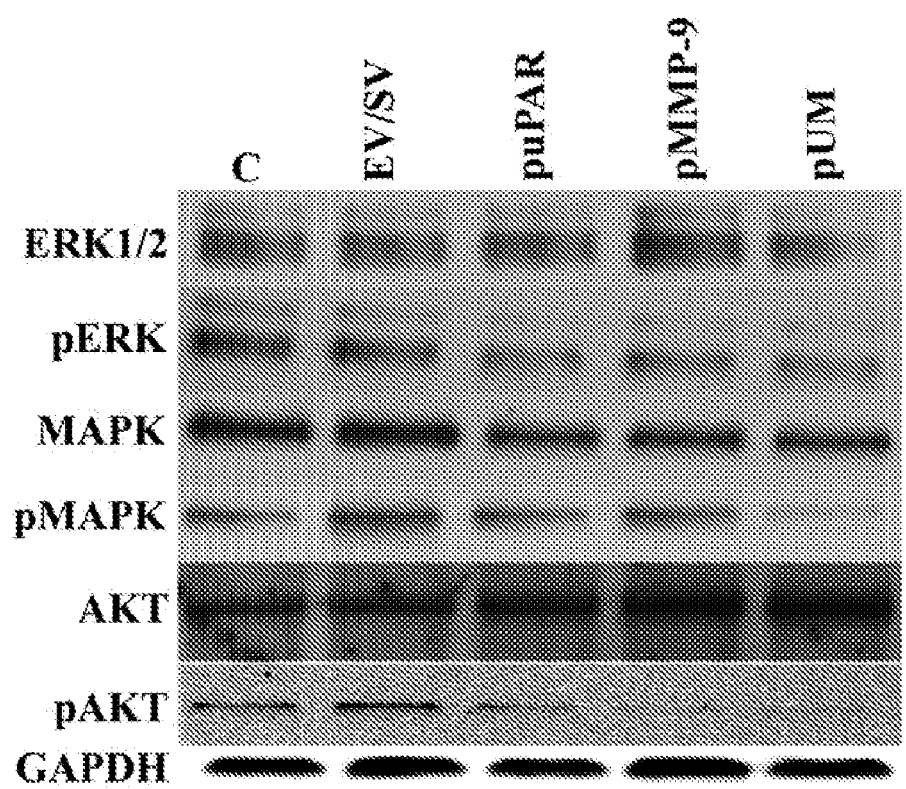

FIG. 15 shows that RNAi-mediated downregulation of uPAR and MMP-9 reduces the phosphorylatin of ERK, MAPK and AKT. Western blot analysis of total and phosphorylated forms of MAPK, ERK and AKT. SNB 19 cells were transfected with EV/SV, puPAR, MMP-9 and pUM on VN-coated plates under serum-free conditioned cells were lysed 72 h later and subjected to SDS-PAGE and immunoblotting with total and phosphorylated forms of MAPK, ERK and AKT antibodies. GADPH antibodies were used to verify that similar amounts of protein were loaded in each lane.

Figure 16A:
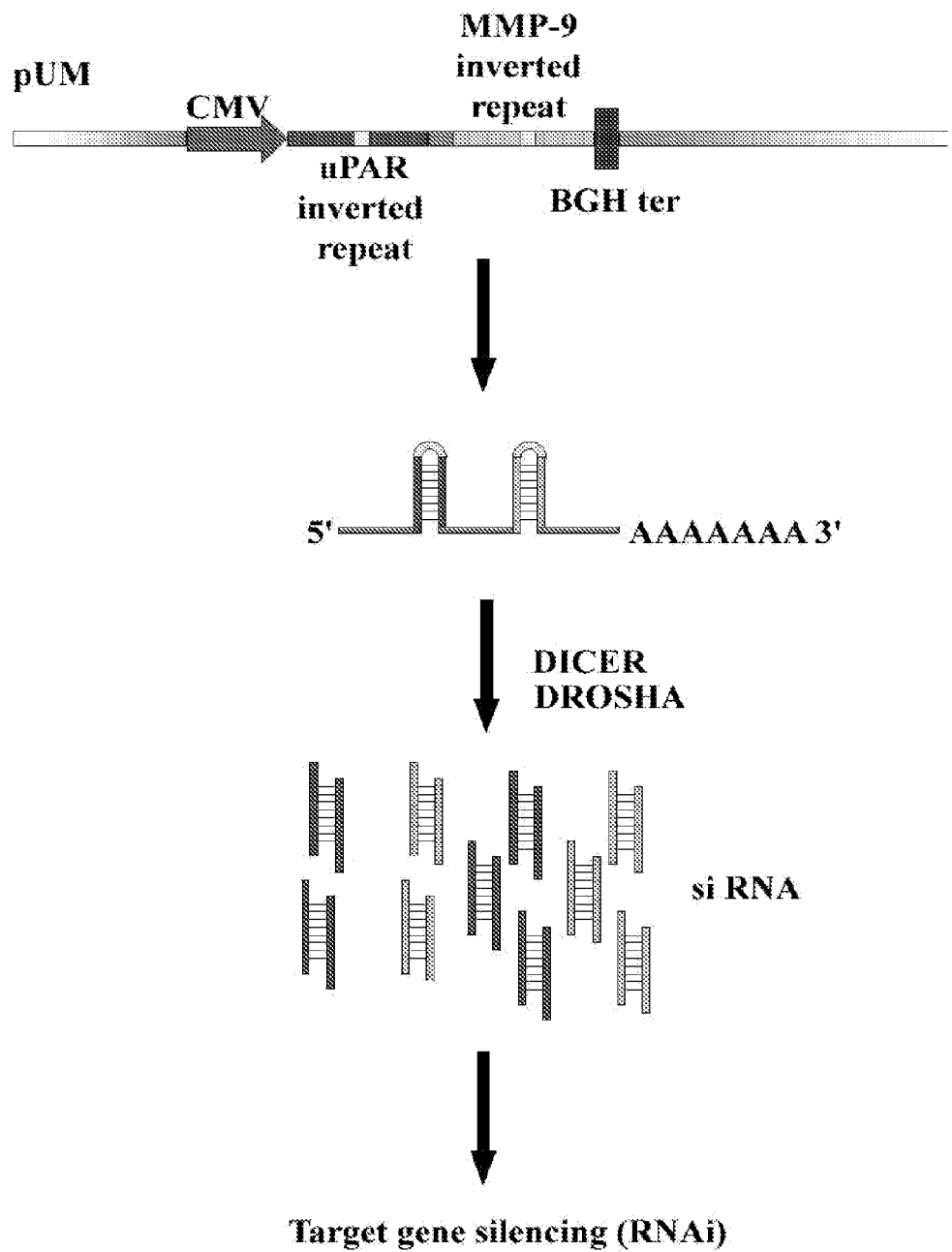
Figure 16B:
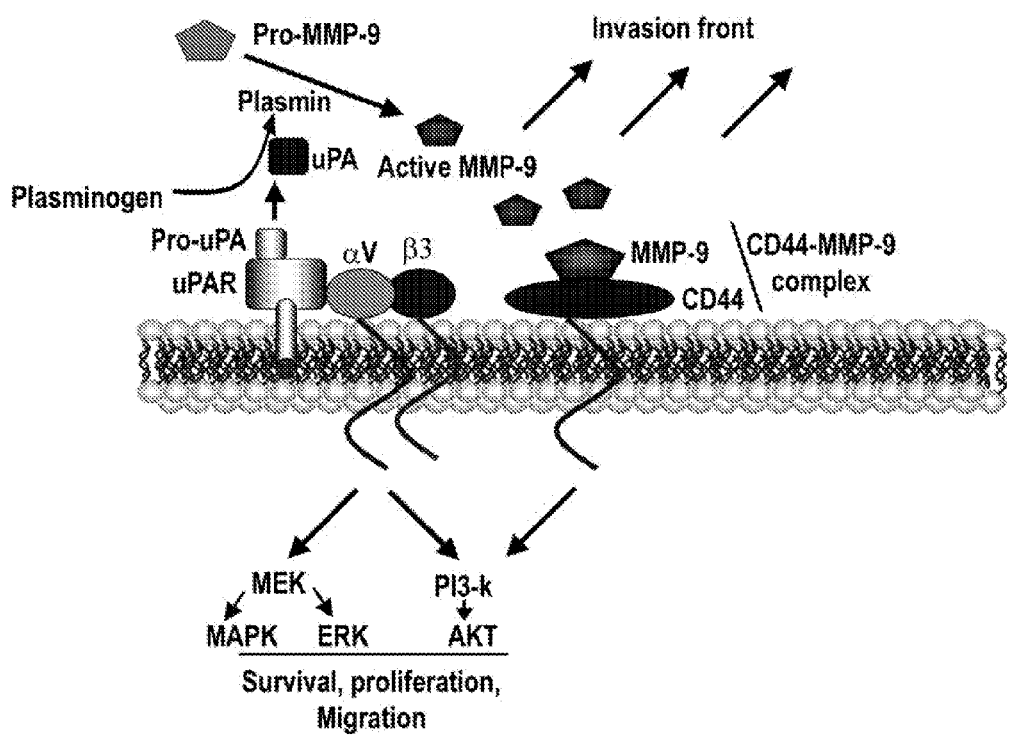

FIG. 16 is a schematic presentation of uPAR and MMP-9 vector (A) and cellular events on the cell surface (B). After activation of plasminogen into plasmin, which in turn activates MMPs, uPA release of several growth factors after degradation of ECM. Schematic presentation demonstrated the involvement of integrins in several signaling pathway molecules.

Figure 17:
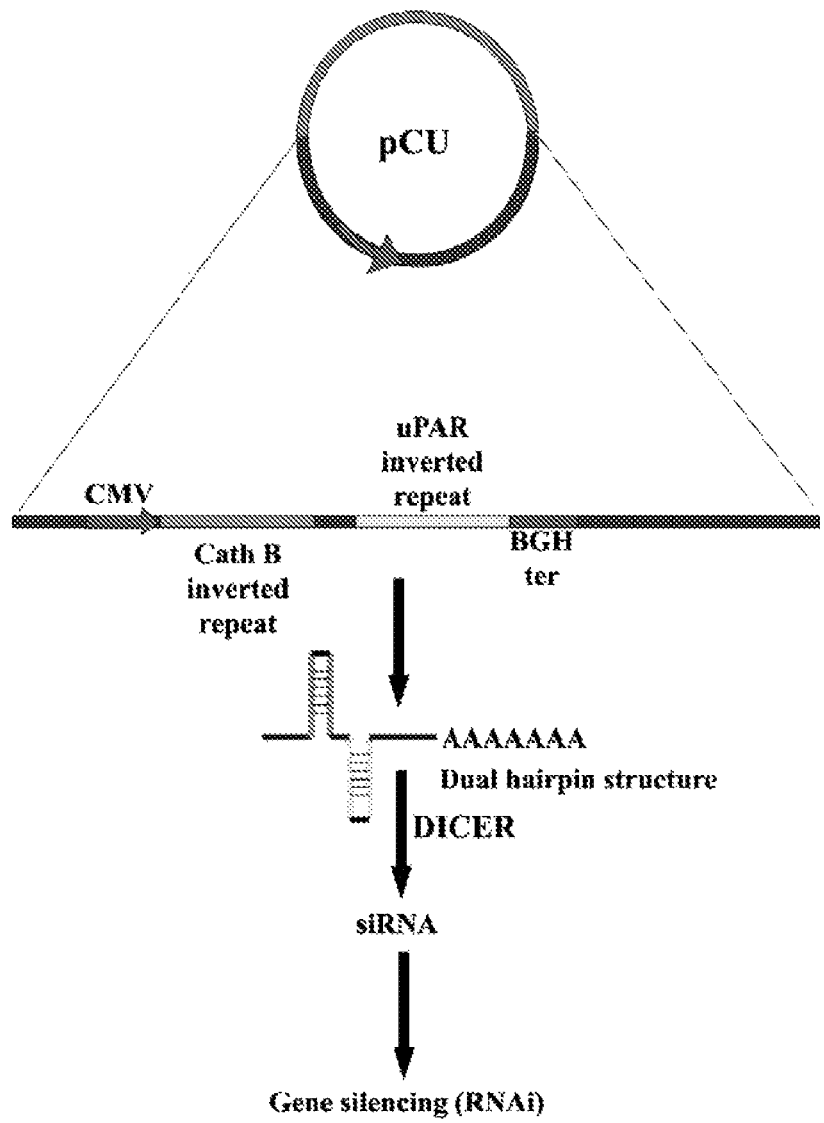

FIG. 17 is a schematic representation showing formation of hpRNA molecules from a single CMV driven dual inverted repeat construct for cathepsin B and uPAR. The CMV viral promoter drives the formation of an RNA molecule that possesses self-complementary inverted repeats for cathepsin B and uPAR.

FIG. 18 shows western blot analysis for uPAR and cathepsin B. SNB19 cells were transfected with mock, an empty vector and a vector encoding siRNA for cathepsin B and uPAR (pCU). Western blot analysis of cathepsin B (A) uPAR (C) protein levels in cell lysates from SNB 19 cells transfected with mock, empty vector and pCU was performed using an antibody specific for cathepsin B and uPAR. β-actin was simultaneously immuno-probed for loading control. Quantitation of cathepsin B (B) and uPAR protein (D) was obtained by scanning the autoradiograms with densitometry.

FIG. 19 shows that RNAi inhibits tumor cell-induced capillary network formation. SNB 19 cells were transfected with mock, empty vector, pC, pU and pCU for 24 h. Then, cells were co-cultured with human dermal endothelial cells for 48 h. After incubation, cells were fixed and blocked with 2% bovine serum albumin for 1 hr and endothelial cells were probed with antibody for factor VIII antigen. (Factor VIII antibody, DAKO Corporation, Carpinteria, Calif.) or H & E staining and examined under a laser scanning confocal microscope (A). Quantification of angiogenesis in co-cultures infected with mock, empty vector or pCU vector (B). Inhibition of tumor angiogenesis in SNB19 cells infected with pCU vector by mouse dorsal window assay (C). PV-pre-existing vasculature, TN-tumor-induced vasculature.

FIG. 20 demonstrates that RNAi inhibits glioma cell migration and invasion. SNB19 GFP spheroids were infected with mock, empty vector, pC, pU and pCU. After 72 h, single glioma spheroids were placed in the center of a vitronectin-coated well in a 96-well plate and cultured for 48 hrs. At the end of the migration assay, spheroids were fixed and photographed (A). The migration of cells from the spheroids was measured using a microscope calibrated with a stage and ocular micrometer (B). The data shown were the mean value±S.D. of the results from four independent experiments from each group. SNB19 cells were trypsinized 72 h after transfection with mock, empty vector, pC, pU and pcU, washed with PBS and resuspended in serum-free medium. Invasion assays were carried out in a 12-well transwell unit (Costar, Cambridge, Mass.) on polycarbonate filters with 8-µm pores coated with Matrigel. After a 24 h incubation period, the cells that had passed through the filter into the lower wells were stained, counted and photographed under a light microscope (C). The percentage of invasion was quantitated (D). Values are mean±S.D. from 5 different experiments ($P<0.001$). Spheroids of SNB19 cells were transfected with mock, empty vector, pC, pU and pcU and stained with DiI and co-cultured with DiO-stained fetal rat brain aggregates. Progressive destruction of fetal brain aggregates by tumor spheroids was observed (E). Quantification of remaining fetal brain aggregates by SNB19 spheroids infected with empty vector, pC, pU or pCU vector (F).

Figure 21:
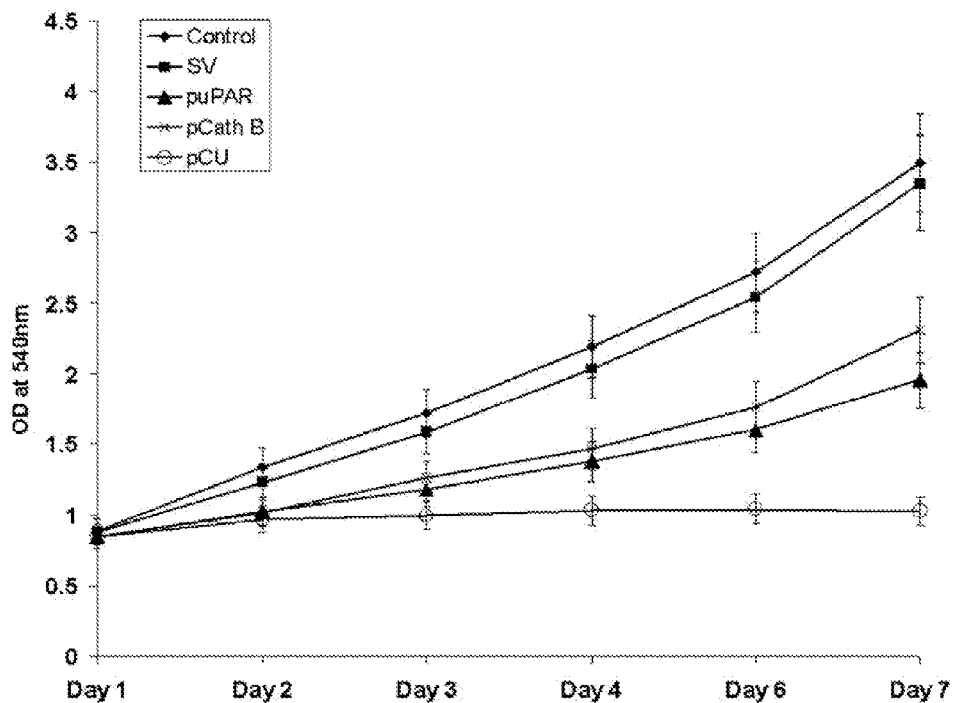

FIG. 21 shows that RNAi mediated downregulation of uPAR and Cathepsin B reduces SNB 19 glioma cell proliferation. Proliferation assay. Briefly, $5\times10^4$ SNB19 cells transfected with PBS, EV, SV, pU, pC and pCU were seeded in VN-coated 96-well microplates under serum-free conditions. The number of viable cells was assessed by the MTT assay. Shown are the mean (±S.D.) values from three separate experiments.

Figure 22:
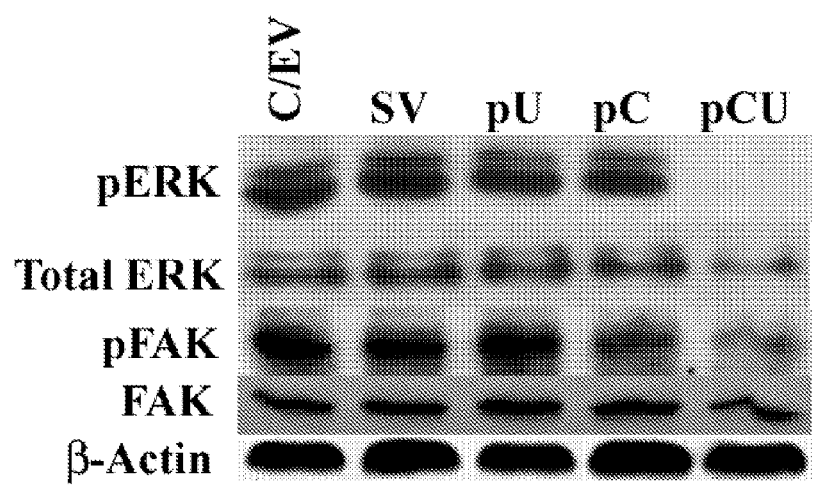

FIG. 22 illustrates that RNAi mediated downregulation of uPAR and Cathepsin B reduces the phosphorylation of ERK and FAK. Western blot analysis of total and phospho ERK, FAK, proteins using their specific antibodies after transfection of SNB19 cells with mock, EV, SV, pU, pC and pCU constructs. β-actin levels served as loading control.

Figure 23:
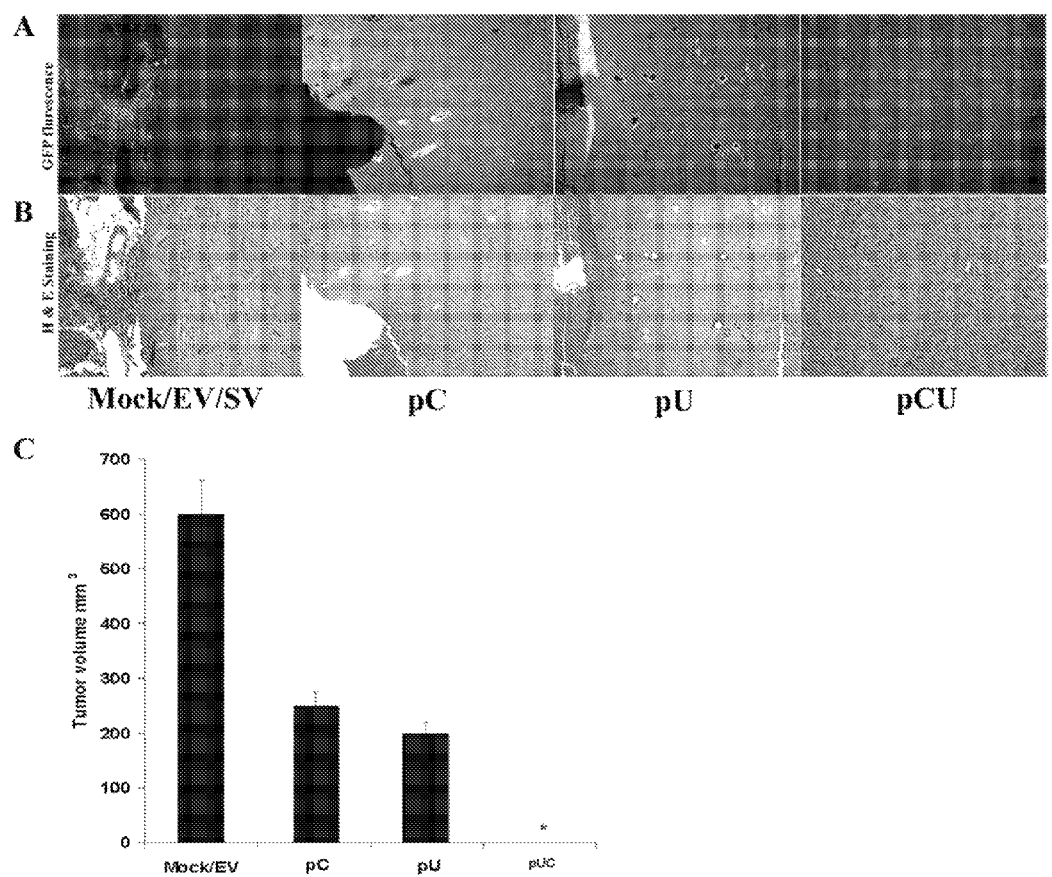

FIG. 23 shows RNAi-mediated regression of pre-established tumor growth. SNB19 GFP tumor cells were injected intracerebrally with the help of a stereotactic frame into nude mice. After 1 week, either an empty vector or a vector expressing siRNA for cathepsin B and uPAR (pCU) or separately by pC or pU was injected into the brain using an Alzet mini osmotic pump. Photomicrographed tumor sections were observed for GFP fluorescence (A) and subsequently stained with hematoxylin and eosin (B). Semiquantification of tumor volume in mock/empty vector, pU, pC and pCU vector treated groups after 5 weeks. Data shown are the ±S.D. values from 6 animals from each group (*$P<0.001$) (C).

Figure 24:
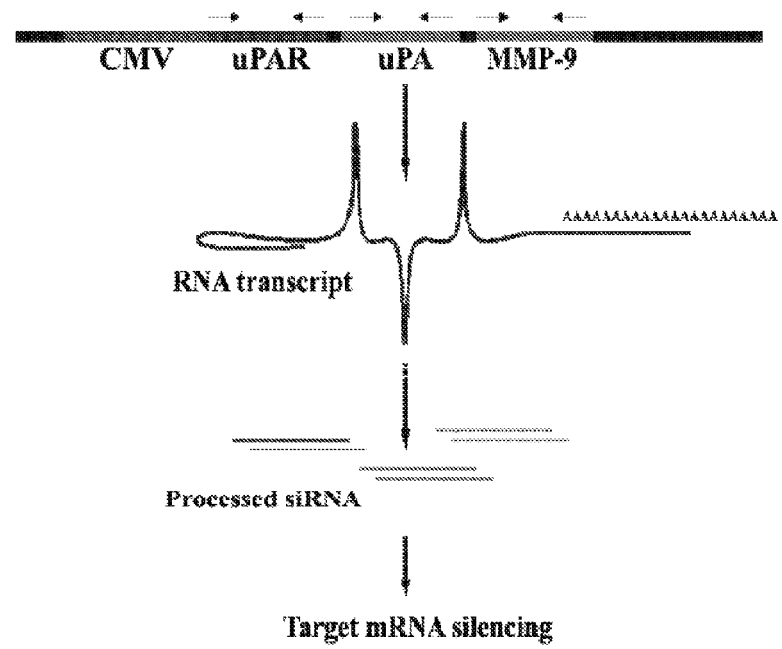

FIG. 24 is a schematic of the formation of hpRNA molecules from a single, CMV-driven, tri-inverted repeat construct for uPAR, uPA and MMP-9 (poly A tail as shown in FIG. 24 is SEQ ID NO: 37). The powerful CMV viral promoter drives the formation of an RNA molecule that possesses self-complementary inverted repeats for uPA, uPAR and MMP-9.

Figure 25:
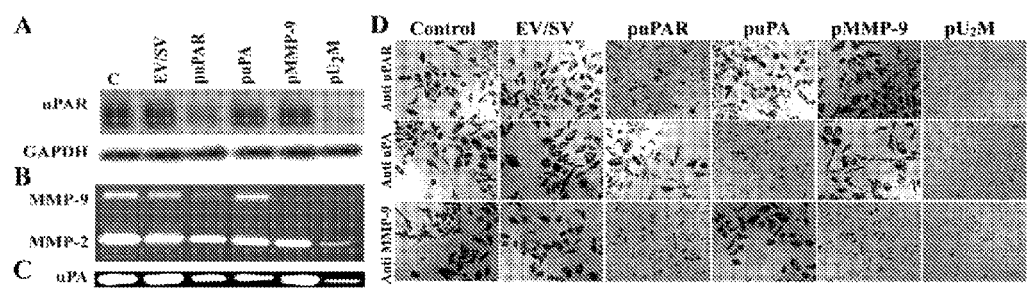

FIG. 25 is a Western blotting, fibrin/gelatin zymography and immunohistochemical analysis of uPA and MMP-9. SNB19 cells were either mock transfected or transfected with an empty vector/scrambled vector (EV/SV) and vectors encoding siRNA uPAR (puPAR), uPA (puPA), MMP-9 (pMMP-9) and a combination of the three together (pU$_2$M). After a 3-day-incubation period, total cell lysates were prepared in extraction buffer and 50 µg of protein from these samples were separated by 12% non-reducing SDS-PAGE and immunoblotted with anti-uPAR antibody (A). GAPDH was immunoprobed simultaneously as a loading control. Conditioned medium was collected from these samples (20 µg) and gelatin and fibrin zymography performed to detect MMP-9 (B) and uPA activity (C). (D) SNB19 cells ($1\times10^4$) were seeded onto Lab-Tek II chamber slides and either mock transfected or transfected with EV/SV and vectors encoding siRNA puPA, puPAR and pMMP-9 either singly or together (pU$_2$M). After 72 hours, cells were fixed, washed for 1 hour with blocking buffer and stained for uPAR, uPA and MMP-9 expression using specific antibodies for uPA, uPAR and MMP-9.

FIG. 26 illustrates the inhibition of glioma angiogenesis and invasion by siRNA constructs. SNB19 cells ($2\times10^4$) were seeded onto 8-well-chamber slides and transfected with EV/SV and vectors encoding siRNA uPAR (puPAR), uPA (puPA), MMP-9 (pMMP-9) and a combination of three together (pU$_2$M). After a 24-hour-incubation period, the medium was removed, cells were co-cultured with either $4\times10^4$ human endothelial cells or $4\times10^4$ endothelial cells alone and were grown in the presence of conditioned media. After 72 hours endothelial cells were stained for factor VIII antigen in the co-cultures (green florescence). Cells grown in the preserved conditioned media were H&E stained and examined under either a florescent microscope or a bright field microscope (A). (B) Quantification of angiogenesis in co-cultures infected with EV/SV, puPAR, puPA, pMMP-9 and pU$_2$M vectors. Values are mean±SD of four experiments. SNB19 cells were trypsinized 72 hours after transfection with EV/SV, puPAR, puPA, pMMP-9 and pU$_2$M, washed with PBS and resuspended in serum-free medium. (C) Invasion assays were carried out in a 12-well transwell unit on polycarbonate filters with 8-µm pores coated with matrigel (0.7 mg ml$^{-1}$). After a 24-hour-incubation period, the cells that had passed through the filter into the lower wells were stained, counted and photographed under a bright-field microscope. (D) The percentage of invasion was quantified.

FIG. 27 shown the inhibition and regression of invasiveness and tumor growth by siRNA by spheroid and intracranial assays. (A) Invasiveness of glioma spheroids was measured by co-culturing glioma spheroids with fetal rat brain aggregates. Spheroids of SNB19 cells were transfected with EV/SV, puPA, puPAR, pMMP-9 and pU$_2$M and stained with DiI and co-cultured with DiO-stained fetal rat brain aggregates. Serial, 1-µm-thick sections were obtained from the surface through the center of the co-cultures with a confocal laser scanning microscope at the indicated time points. (B) The remaining volume of the rat brain aggregate transfected with EV/SV, puPA, puPAR, pMMP-9 and pU$_2$M was measured. The values are mean±SD of three experiments. (C,D) RNA-mediated regression of pre-established tumor growth. SNB19 GFP cells in suspension ($2\times10^6$ in 10 µl serum-free medium) were injected intracranially. One week later, the mice were injected with either EV/SV or siRNA-expressing vectors (puPAR, puPA, pMMP-9 and pU$_2$M) using an Alzet mini osmotic pump (constructs diluted to 1.5 µg ml$^{-1}$ in PBS and injected at 0.25 µg hour$^{-1}$, with six mice in each group). After a 5-week follow-up period, mice were sacrificed, their brains removed, paraffin embedded and sectioned. Sections were observed under fluorescence microscopy for GFP-expressing cells. (D) Semi-quantification of tumor volume in control, EV/SV, puPAR, puPA, pMMP-9 and pU$_2$M-treated groups was assessed after 5 weeks. Data are shown mean±SD of six animals from each group.

Figure 28:
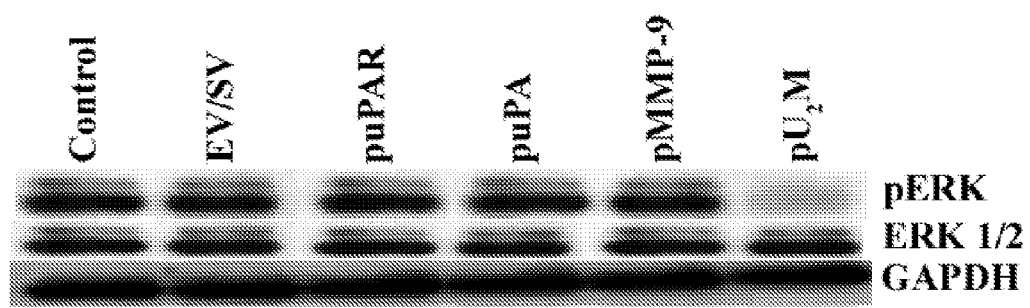

FIG. 28 demonstrates that RNAi-mediated downregulation of uPAR, uPA and MMP-9 reduces phosphorylation of ERK. Western blot analysis of total and phosphorylated ERK (pERK) protein after transfection of glioblastoma cells with EV/SV, puPAR, puPA, pMMP-9 and pU$_2$M constructs. GAPDH levels served as loading control.

Figure 29:
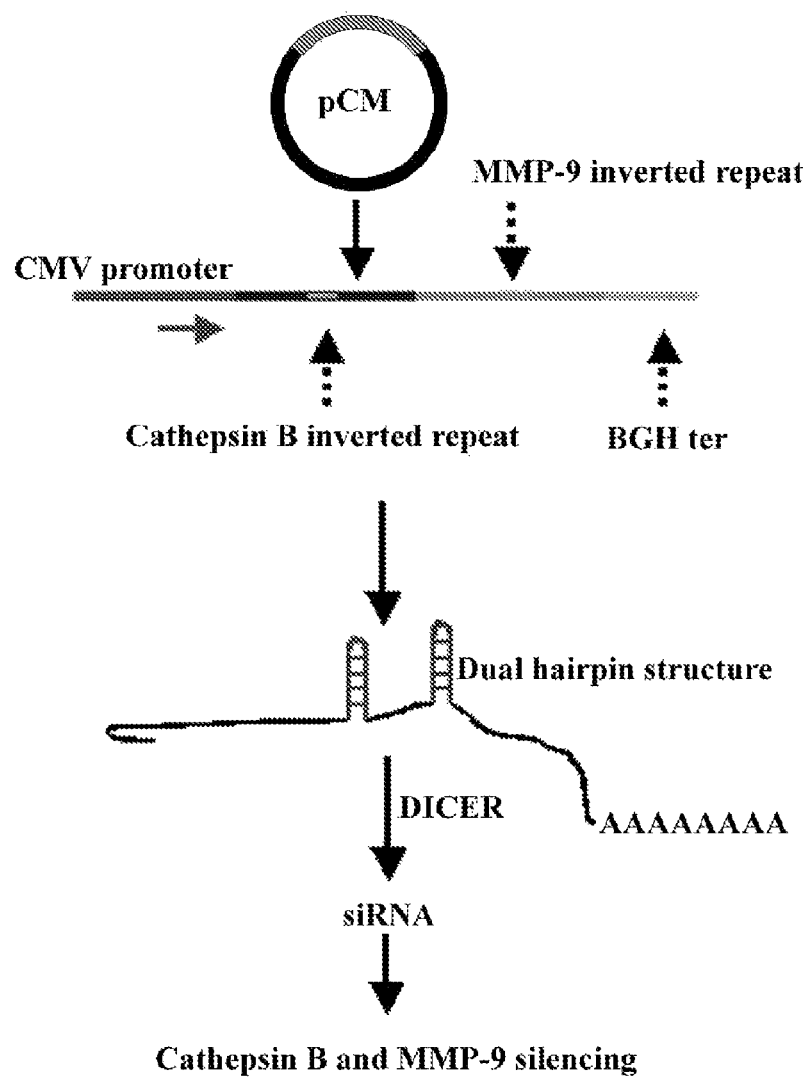

FIG. 29 is a schematic representation of siRNA expression for cathepsin B and MMP-9 from pCM vector. pCDNA 3 plasmid constructs were developed having two complementary inverted repeats driven by a CMV promoter directed against cathepsin B and MMP-9. The CMV promoter drives the formation of a dual hairpin structure which, in turn, was processed by the double strand RNA recognizing enzyme DICER to form viable SiRNA-molecules. Stability of the dual hairpin molecule was ensured because of the secondary structure of the molecule which is reminiscent of an mRNA molecule having a poly A tail driven by a bovine growth hormone (BGH) poly-a-signal sequence.

Figure 30:
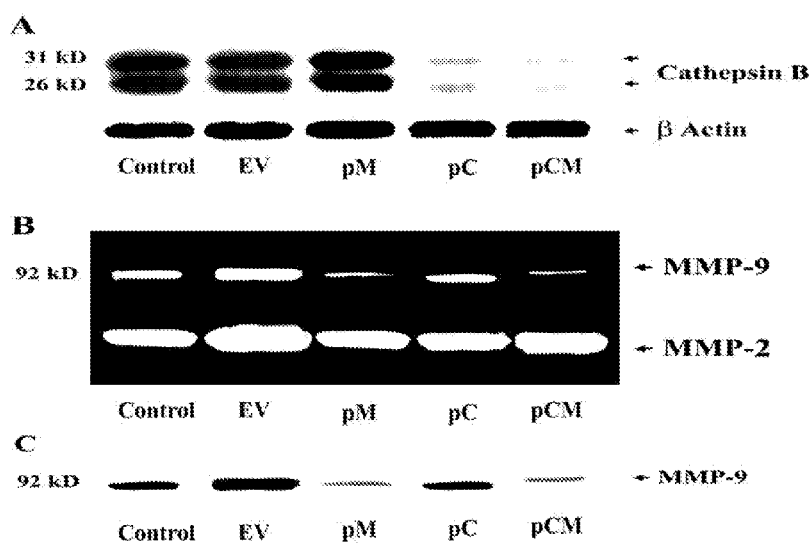

FIG. 30 confirms that RNA interference decreased cathepsin B and MMP-9 levels in SNB19 cells. Total cell lysates and serum free medium were collected from SNB19 cells transfected with mock, empty vector or a vector encoding siRNA for MMP-9 (pM) and cathepsin B (pC) and together (pCM). Subsequently, 30 µg of protein from these samples were separated under nonreducing conditions on 8% to 12% SDS-PAGE and transferred to nitrocellulose membranes. The membranes were probed with antibodies for Cathepsin B (A) and MMP-9 (C) and with appropriate secondary antibody (horseradish peroxidase conjugate) and developed according to the manufacture's protocol (Amersham, Arlington Heights, Ill.). β-actin was simultaneously immunodetected to verify the loading of similar amounts of cell lysates. MMP-9 activity of SNB19 cells infected with empty vector, pC, pM or pCM vector for 3 days in serum-free medium and were determined by gelatin zymography (B).

FIG. 31 shows that RNAi inhibits tumor cell-induced capillary network formation. SNB19 cells were transfected with mock, empty vector, pM, pC and pCM for 24 h. Then, cells were co-cultured with human dermal endothelial cells for 48 h. After incubation, cells were fixed and blocked with 2% bovine serum albumin for 1 hr and endothelial cells were probed with antibody for factor VIII antigen. (Factor VIII antibody, DAKO Corporation, Carpinteria, Calif.) and examined under a fluorescent microscope after probing with an appropriate FITC conjugated secondary antibody. Endothelial cells grown in the presence of SNB19 (control, empty vector, PM, pC, or pCM transfected) conditioned media were H and E stained and photographed (A). Quantification of angiogenesis in co-cultures infected with mock, empty vector or pCM vector (B). Inhibition of tumor angiogenesis in SNB19 cells infected with pCM vector by mouse dorsal skinfold assay (C). PV-pre-existing vasculature, TN-tumor-induced vasculature. Photographs were taken using light microscopy (upper panel) and for FITC fluorescence (lower panel) to determine the presence of newly developed vasculature.

FIG. 32 demonstrates that RNAi inhibits glioma cell migration and invasion. SNB19 GFP spheroids were infected with mock, empty vector and a vector encoding siRNA for cathepsin B and MMP-9 (pCM). After 3 days, single glioma spheroids were placed in the center of a vitronectin-coated well in a 96-well plate and cultured for 48 hrs. At the end of the migration assay, spheroids were fixed and photographed (A). SNB19 cells were trypsinized 3 days after transfection with mock, empty vector and a vector encoding siRNA for cathepsin B and MMP-9 (pCM), washed with PBS and resuspended in serum-free medium. Invasion assays were carried out in a 12-well transwell unit (Costar, Cambridge, Mass.) on polycarbonate filters with 8-µm pores coated with Matrigel. After a 24 h incubation period, the cells that had passed through the filter into the lower wells were stained, counted and photographed under a light microscope (B). Spheroids of SNB19 cells were transfected with mock, empty vector and a vector encoding siRNA for cathepsin B and MMP-9 (pCM) and stained with DiI and co-cultured with DiO-stained fetal rat brain aggregates. Progressive destruction of fetal brain aggregates by tumor spheroids was observed (C).

Figure 33:
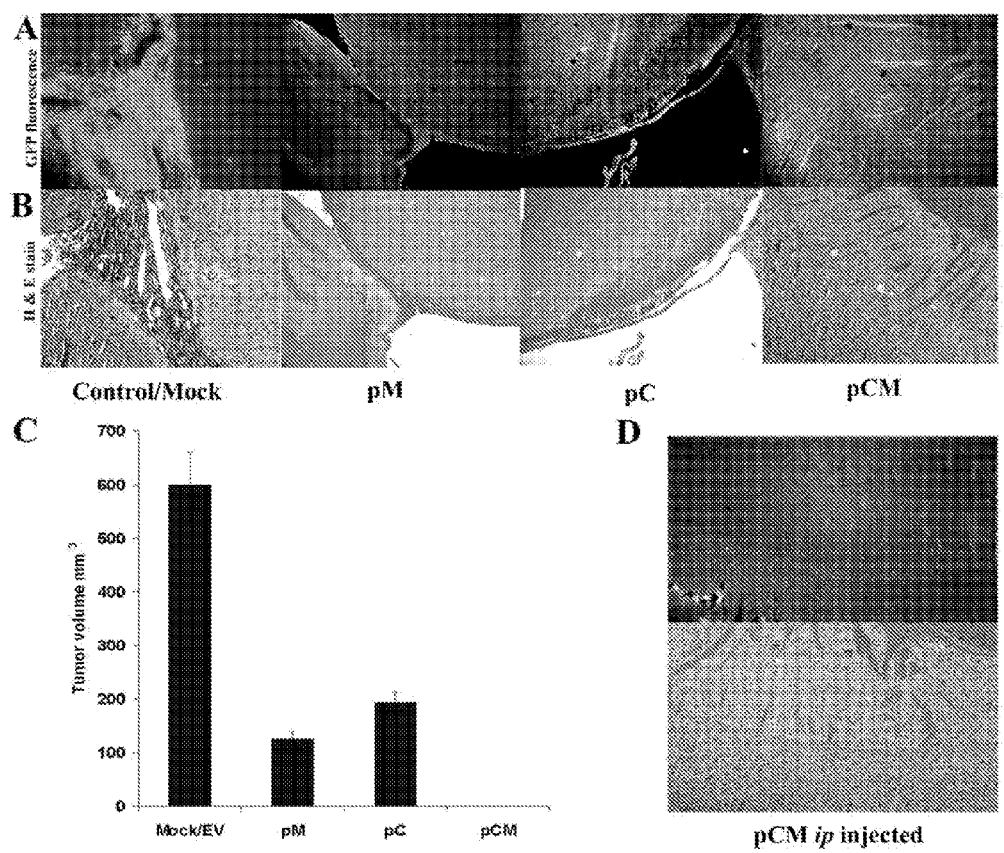

FIG. 33 shows RNAi-mediated regression of pre-established tumor growth. SNB19 GFP tumor cells were injected intracerebrally with the help of a stereotactic frame into nude mice. After 1 week, either an empty vector or a vector expressing siRNA for cathepsin B and MMP-9 (pCM), cathepsin B (pC) or MMP-9 (pM) was injected into the brain using an Alzet mini osmotic pump. Photographs of tumor sections were observed for GFP fluorescence (A) and subsequently stained with hematoxylin and eosin (B). Semiquantification of tumor volume in mock/empty vector, pM, pC and pCM vector treated groups after 5 weeks was done. Data shown are the ±S.D. values from 6 animals from each group (*P<0.001) (C). In another experiment, 10 days after intracerebral injection, pCM vector was injected intraperitoneally twice and the animals sacrificed after 4 months (D).

Figure 34:
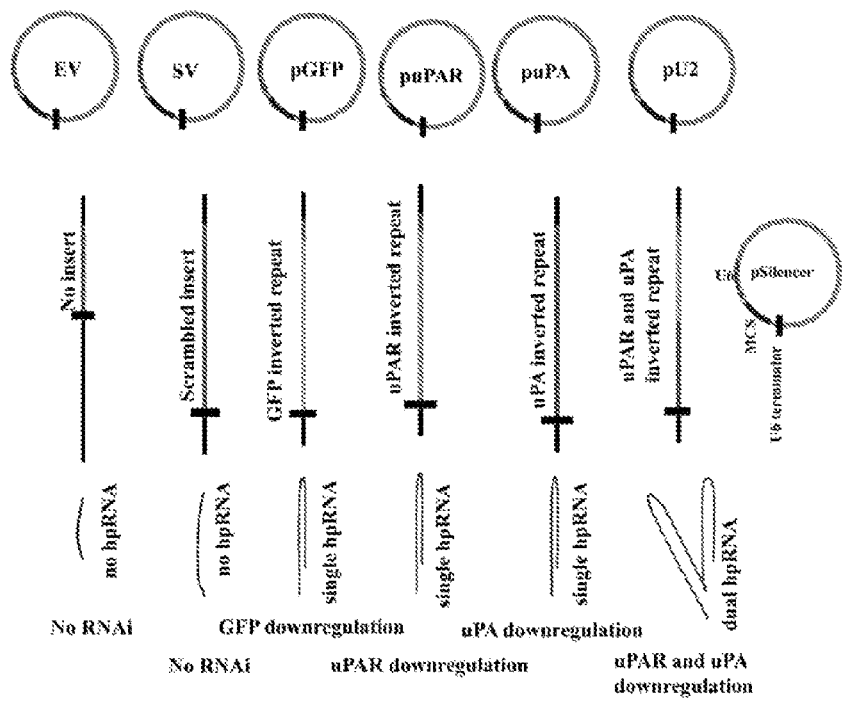

FIG. 34 is a schematic representation of RNA pol II promoter (CMV) for the induction of RNAi.

Figure 35:
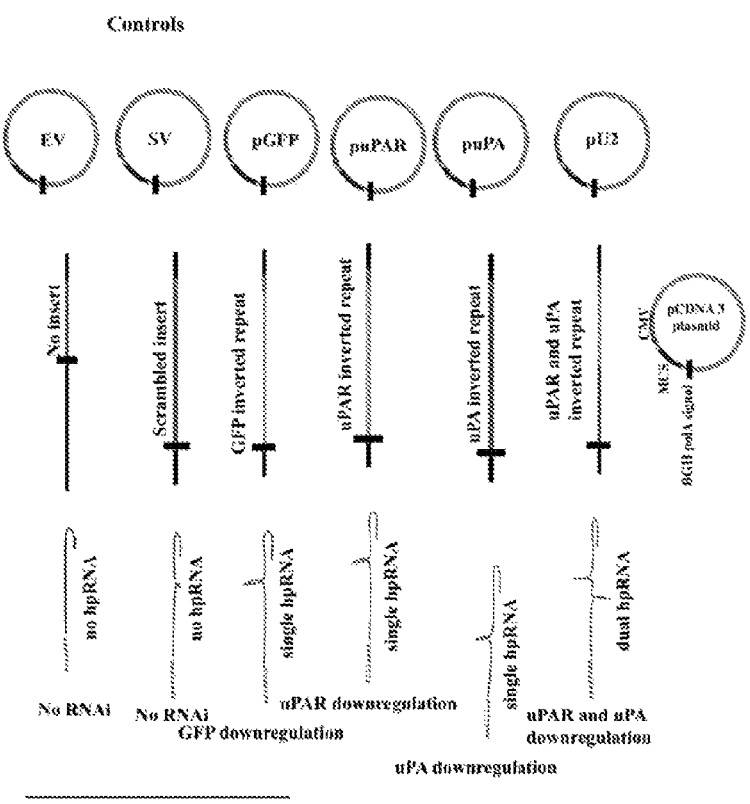

FIG. 35 is a schematic representation of RNA pol III based promoter (U6) for the induction of RNAi.

Figure 36:
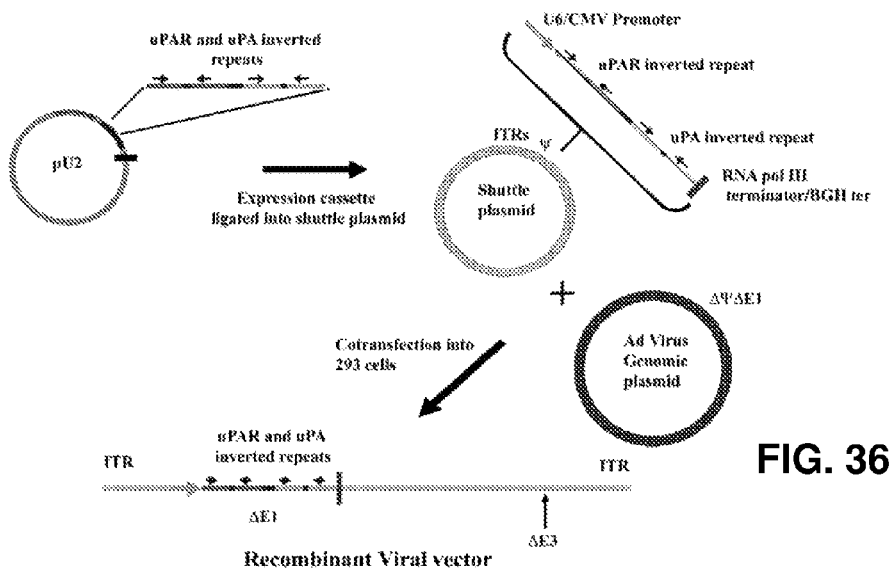

FIG. 36 is a schematic representation of recombinant adeno virus production.

Figure 37:
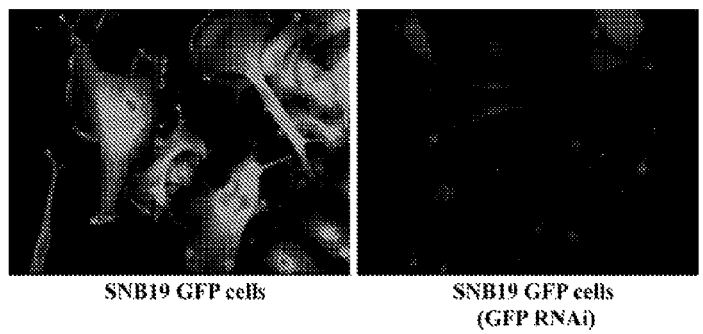

FIG. 37 indicates SNB19 GFP cells transfected with RNAi for GRP or mock showing GRP expression.

Figure 38:
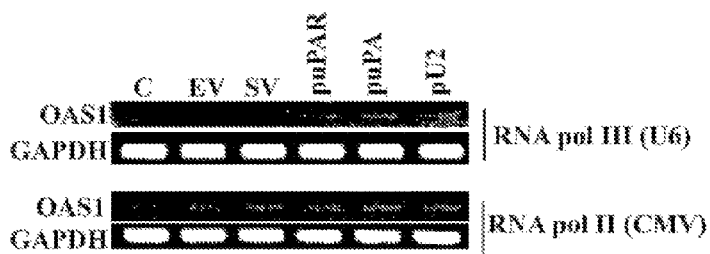

FIG. 38 shows OAS1 expression in SNB 19 cells transfected with RNAi vectors driven by RNA pol II (CMV) or RNA pol III (U6) was determined by RT-PCR. RT-PCRT for GAPDH served as control.

Figure 39:
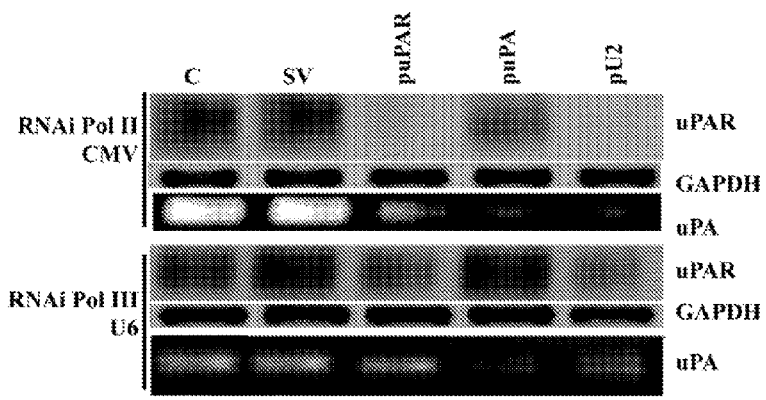

FIG. 39 demonstrates dowregulation of uPAR and uPA as determined by Western blot analysis and fibrin zymography of SNB19 cell lysates from cells transected with either U6- or CMV-driven promoters. RNAi plasmids for scrambled vector (SV), RNAi expressing plasmid for uPAR (puPAR), uPA (puPA) and uPAR-uPA bicistronic construct (pU2). GAPDH was probed for loading control.

Figure 40:
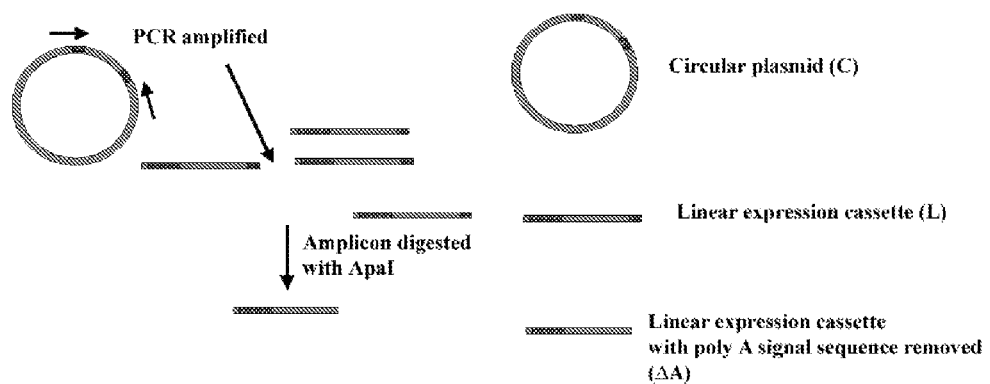

FIG. 40 is a schematic representation of siRNA expression constructs used to determine the induction of cellular immune response.

Figure 41:
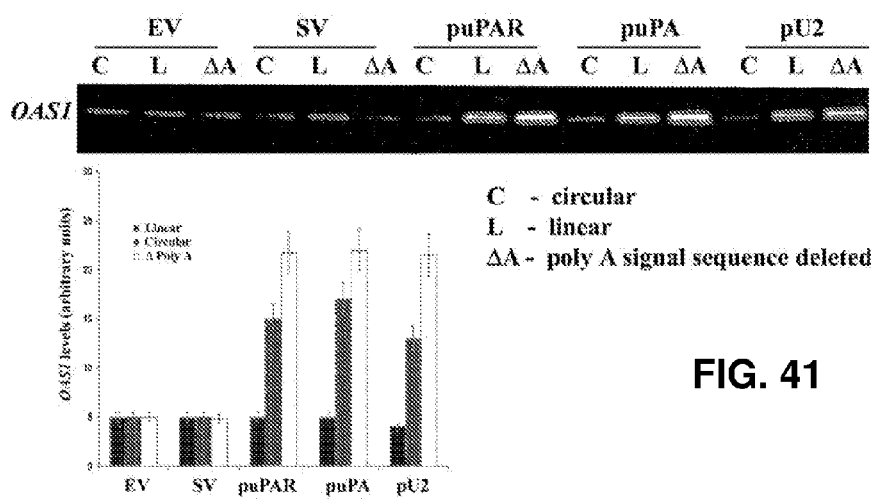

FIG. 41 shows determination of 2'5'-oligoadenylate synthetase (OAS1) expression in SNB19 cell transfected with circular (C), linear (L) or poly A signal deleted (ΔA) expression cassette for empty vector (EV), scrambled vector (SV), siRNA expression constructs for uPAR (puPAR), uPA (puPA) and bicistronic construct for uPAR and uPA (pU2) by RT-PCR. RT-PCR was normalized with GAPDH. OAS1 expression was quantified as shown.

Figure 42:
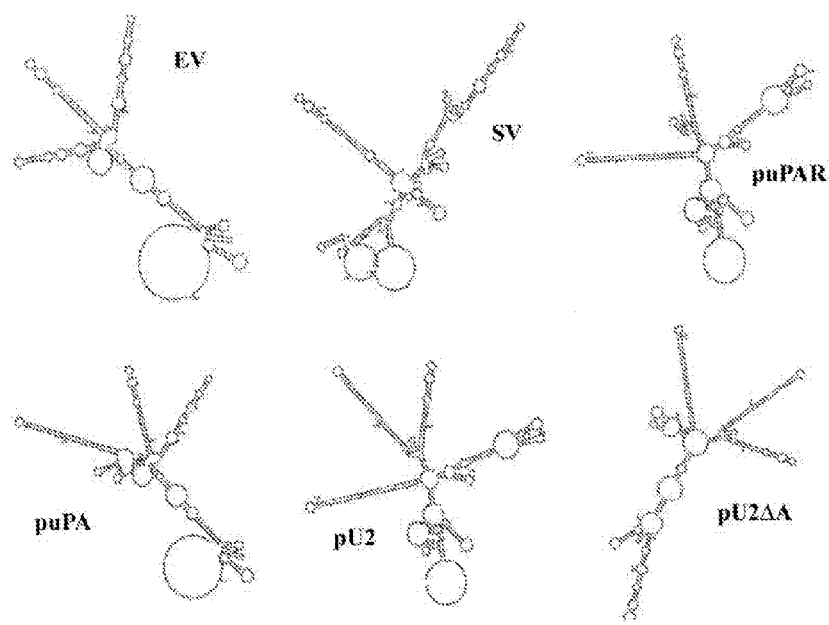

FIG. 42 is a schematic representation of predicted secondary structure of EV and SV transcripts showing no viable RNAi inducer-like structure and predicted puPAR, puPA and pU2 transcript with poly A and without poly A (pU2ΔA).

Figure 43:
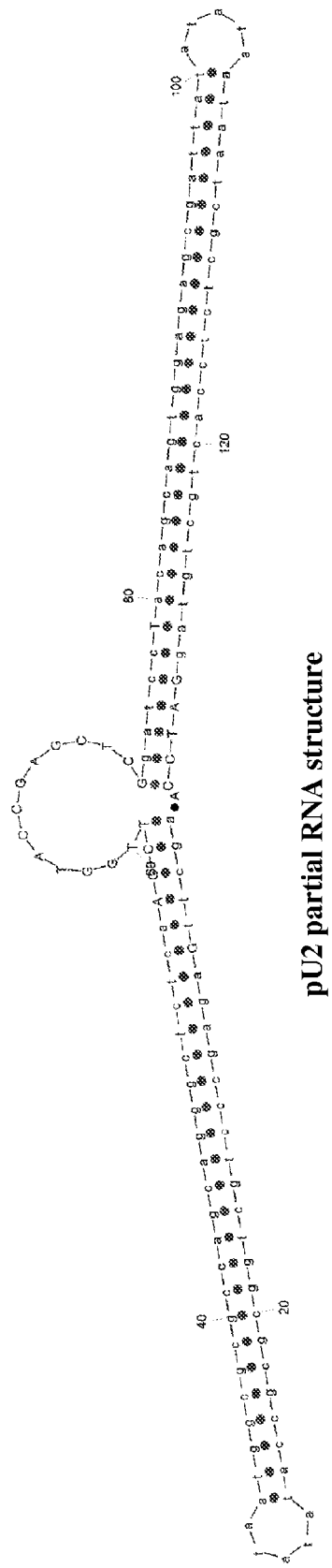

FIG. 43 is a schematic representation of partial secondary structure of pU2 transcript showing space secondary structure. Space secondary structure has no resemblance to mRNA.

Figure 44:
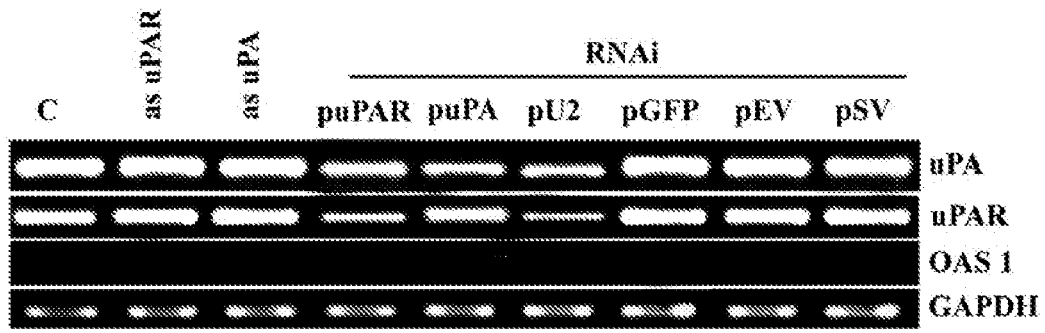

FIG. 44 shows RT-PCR on total RNA isolated from control (C), antisense uPAR (as uPAR), antisense uPA (as uPA) and RNAi constructs for uPAR (puPAR), uPA (puPA), uPAR-uPA (pU2), GFP (pGFP), empty vector (pEV), and scrambled vector (pSV) for uPA, uPAR and OAS 1 mRNA levels. GAPDH served as control.

Figure 45:
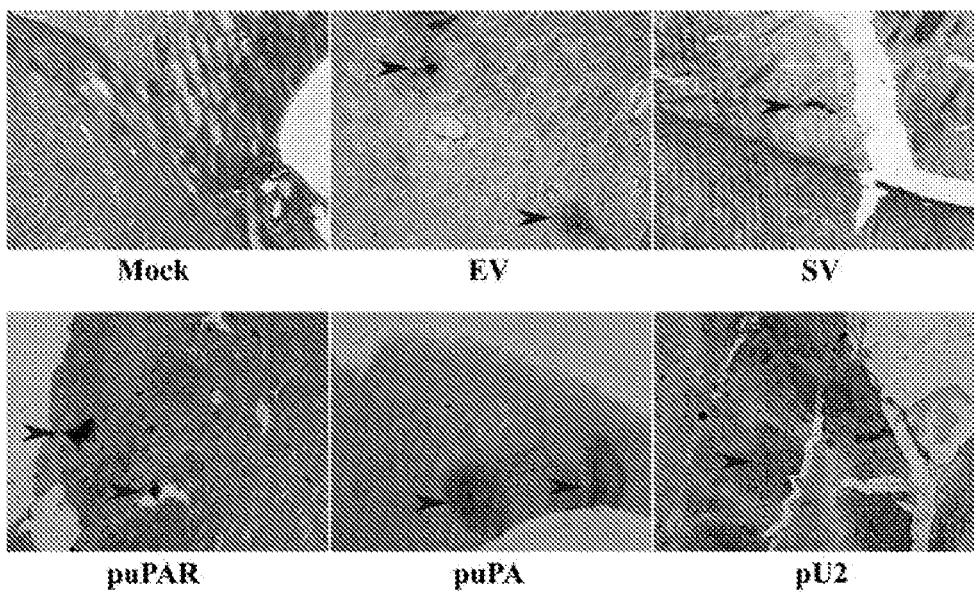

FIG. 45 shows in situ hybridization of CMV promoter in IP-injected mice. Cranial sections of mice injected intra peritoneally with saline (Mock), empty vector (EV), scrambled vector (SV), RNAi expression vectors for uPAR (puPAR), uPA (puPA), and uPAR-uPA bicistronic construct (pU2), were probed for the presence of DNA containing CMV promoter by labeling probe DNA with alkaline phosphatase (AP). AP activity was detected by Western Blue AP substrate (Promega, Madison, Wis.).

Figure 46:
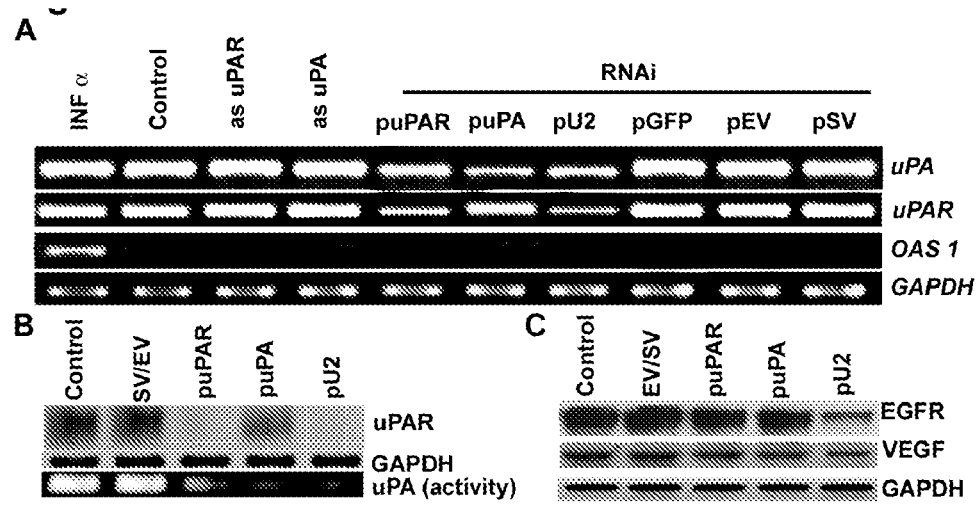

FIG. 46 shows determination of uPAR and uPA mRNA levels using semi-quantitative RT-PCR.

Figure 47:
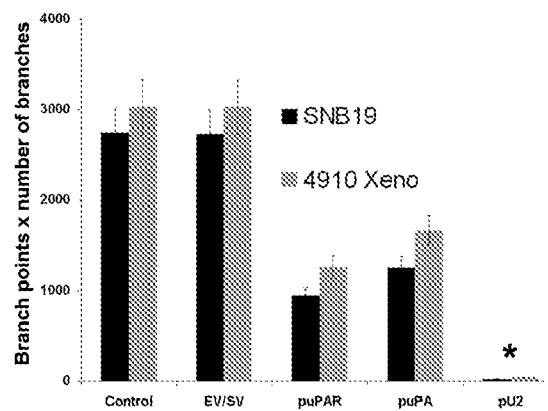

FIG. 47 shows in vitro angiogenesis quantification. The degree of angiogenic induction was quantified for both SNB19 and 4910 cells based on the numerical value for the product of the number of branches and number of branch points (*p value=0.005).

Figure 48:
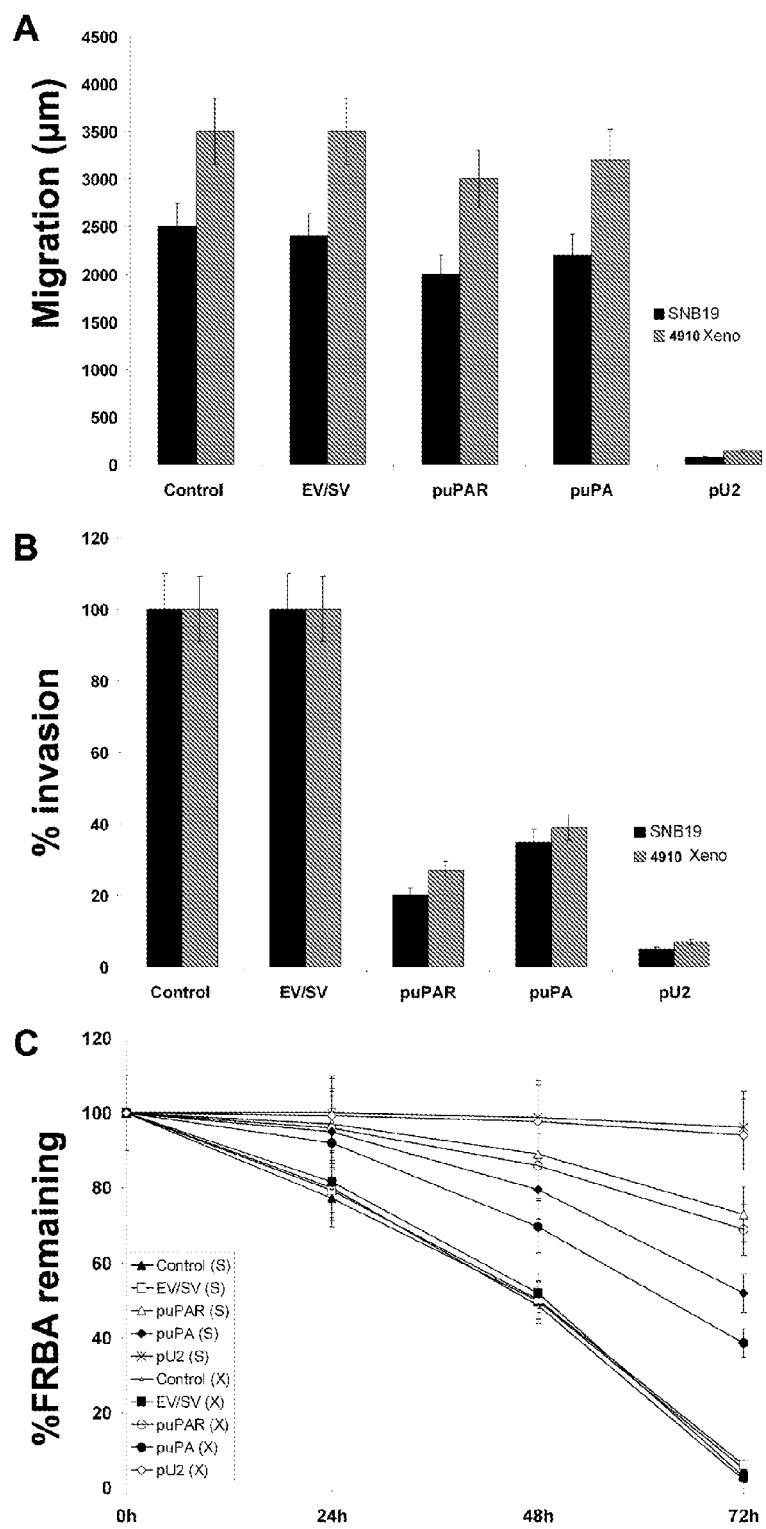

FIG. 48 shows results of migration assay for spheroids. Cell migration from spheroids to monolayers was quantified using a microscope calibrated with a stage and ocular micrometer and represented graphically (A). Cells on the lower side of the membrane were fixed, stained with Hema-3 and quantified as percent invasion (B). The remaining volume of the rat brain aggregates at 24, 48 and 72 h were quantified using image analysis software as described previously and graphically represented (C). X=4910 xeno.

Figure 49:
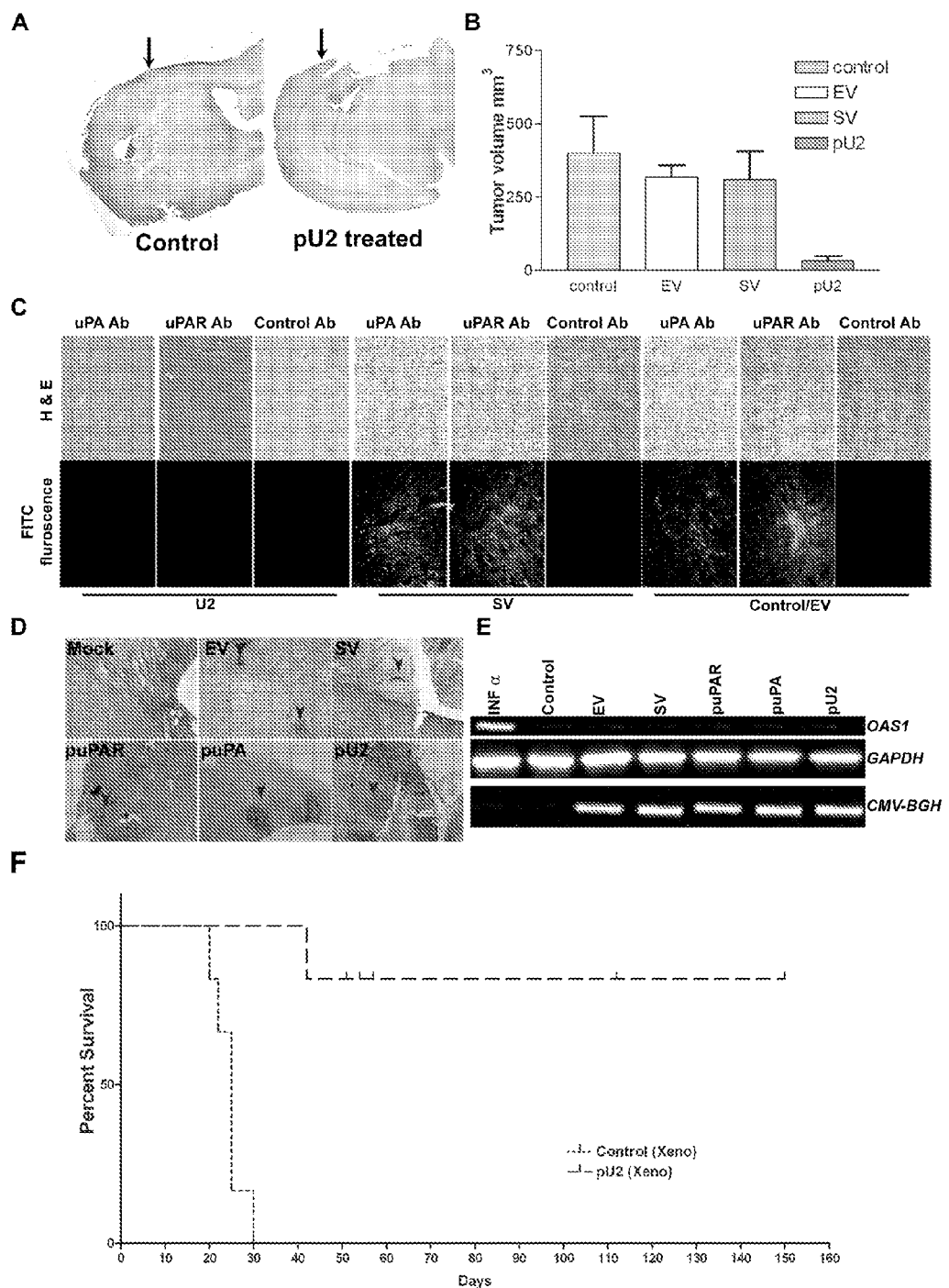

FIG. 49 shows results from an intracerebral tumor model after treatment with intraperitoneal injections of pU2. Sections were stained with hematoxylin and eosin to visualize tumor cells and to examine tumor volume (arrows point to approximate site of intracranial implantation site) (FIGS. 5A & 5B). A control study was performed using a normal rabbit immunoglobulin fraction as the primary antibody (control Ab) instead of uPAR or uPA (FIG. 5C). The presence of CMV promoter was determined by the development of a blue precipitate of NBT alkaline phosphatase substrate. Arrows point to region of localization (FIG. 5D). RT-PCR was performed using primers specific for OAS1 (FIG. 5E). Survival curve was plotted per standard methods and graphically represented (FIG. 5F).

DETAILED DESCRIPTION

Small hairpin RNAs (shRNAs), also referred to as small interfering RNAs (siRNAs), target human genes such as uPA and uPAR to inhibit tumor growth, tumor invasion, and tumor proliferation. siRNA constructs significantly inhibited uPA and uPAR expression at both the mRNA and protein levels in a highly metastatic prostate cancer cell line PC3. uPA-uPAR knockdown in PC3 cells resulted in a significant reduction of tumor cell invasion as indicated, for example, by a Matrigel invasion assay. Simultaneous silencing of the genes for uPA and uPAR using a single plasmid construct expressing shRNAs for both uPA and uPAR significantly reduced cell viability and also resulted in the induction of apoptotic cell death. RNAi for uPA and uPAR also abrogated uPA-uPAR signaling to downstream target molecules such as extracellular-signal regulated kinases 1/2 (ERK1/2) and the signal transducer and activator of transcription 3 (Stat 3). Intratumoral injection with a plasmid construct expressing shRNAs for uPA and uPAR significantly inhibited established tumor growth and survival in an orthotopic mouse prostate cancer model. Evidence of a signaling network operating downstream of uPA-uPAR that actively advances tumor cell invasion, proliferation and survival of prostate cancer cells is uncovered. RNAi-directed targeting of uPA and uPAR and the corresponding siRNAs are novel therapeutic agents for cancer therapy, including prostate cancers.

siRNA-mediated target RNA degradation of uPAR and MMP-9 in human glioma cell lines resulted in tumor inhibition. RNAi directed towards uPAR and MMP-9 achieved a specific inhibition of uPAR and MMP-9. A bicistronic construct (pUM) inhibited the formation of capillary-like structures in both in vitro and in vivo models of angiogenesis. Blocking the expression of uPAR and MMP-9 resulted in significant inhibition of glioma tumor invasion in Matrigel and spheroid invasion assay models. RNAi for uPAR and MMP-9 inhibited cell proliferation and reduced the levels of phosphorylated forms of MAPK, ERK and AKT signaling pathway molecules when compared to parental and empty vector/scrambled vector (EV/SV) transfected SNB 19 cells. Further, using RNAi to simultaneously target two protease molecules and injecting these constructs intracerebrally in vivo using Alzet mini pumps or intraperitoneal injections resulted in significant regression of pre-established intracerebral tumor growth. Use of hairpin siRNA expression vectors for uPAR and MMP-9 provides an effective therapeutic tool for cancer therapy, including glioblastoma.

In another embodiment, the RNAi approach silenced uPAR and cathepsin B expression. RNAi was used to inhibit the expression of proteases implicated in the extracellular matrix degradation, a characteristic feature of tumor progression. RNAi of uPAR and cathepsin B reduced glioma cell invasion and angiogenesis in in vitro and in vivo models. Intratumoral injections of plasmid vectors expressing hpRNA (siRNA) for uPAR and cathepsin B resulted in the regression of pre-established intracranial tumors. RNAi for uPAR and cathepsin B inhibited cell proliferation and reduced the levels of pERK and pFAK as compared to controls. RNAi operates in human glioma cells and provides a basis for cancer gene therapy, including glioblastoma.

The RNAi approach silenced uPA, uPAR and MMP-9 expression in tumor cells. A cytomegalovirus (CMV) promoter-driven DNA-template in a single tricistronic construct induced hairpin RNA (hpRNA)-triggered RNAi to inhibit uPA, uPAR and MMP-9 gene expression with a single construct. uPAR protein levels and enzymatic activity of uPA and MMP-9 were found to significantly decrease in cells transfected with a plasmid expressing hairpin siRNA for uPAR, uPA and MMP-9. pU2M-transfected SNB19 cells significantly decreased uPA, uPAR and MMP-9 expression compared to mock and EV/SV-transfected cells, determined by immunohistochemical analysis. The single constructs for these molecules resulted in a specific inhibition of their respective protein levels, as demonstrated by immunohistochemical analysis. After transfection with a plasmid vector expressing dsRNA for uPA, uPAR and MMP-9, glioma-cell invasion was retarded compared with mock and EV/SV-treated groups, demonstrated by Matrigel-invasion assay and spheroid-invasion assay. Downregulation of uPA, uPAR and MMP-9 using RNAi inhibited angiogenesis in an in vitro (co-culture) model. Direct intratumoral injections of plasmid DNA expressing hpRNA for uPA, uPAR and MMP-9 also significantly regressed pre-established intracranial tumors in nude mice. Cells treated with RNAi for uPAR, uPA and MMP-9 showed reduced pERK levels compared with parental and EV/SV-treated SNB19 cells. Simultaneous repression of uPAR, uPA and MMP-9 is a therapeutic tool to treat cancers.

A cytomegalovirus (CMV) promoter-driven DNA hairpin RNA (hpRNA, siRNA) from a single construct, blocked MMP-9 and cathepsin B gene expression. Transfection of a plasmid vector expressing dsRNA for MMP-9 and cathepsin B significantly inhibited MMP-9 and cathepsin B expression and reduced the invasive behavior of SNB19, glioblastoma cell line in Matrigel and spheroid invasion models. Down-regulation of MMP-9 and cathepsin B using RNAi in SNB19 cells also reduced cell-cell interaction of human microvascular endothelial cells, resulting in the disruption of capillary network formation in both in vitro and in vivo models. Direct intratumoral injections of plasmid DNA expressing hpRNA for MMP-9 and cathepsin B significantly inhibited established glioma tumor growth and invasion in intracranial tumors in vivo. Intraperitoneal (ip) injections of plasmid DNA expressing hpRNA for MMP-9 and cathepsin B completely regressed pre-established tumors for a significant period. Simultaneous RNAi-mediated targeting of MMP-9 and cathepsin B is a suitable treatment methodology for human gliomas.

Plasmid-based, CMV promoter-driven hpRNA targeting uPAR, uPA and MMP-9, either singly or simultaneously, induces RNAi in the SNB19 human glioma cell line. The simultaneous, RNAi-mediated downregulation of uPAR, uPA and MMP-9 in SNB19 human glioma cells caused:

(1) Inhibition of invasion and angiogenesis in vitro.
(2) Regression of pre-established intracranial tumors in nude mice in vivo.
(3) Reduction in the phosphorylation of ERK 1 and 2 signaling molecules.

siRNAs or shRNAs or hpRNAs driven from a circular plasmid (e.g., uPA, uPAR, MMP-9, and cathepsin B or any combination thereof) is suitable to induce RNA interference in vitro. siRNAs from circular plasmids are stable and do not induce undesirable immune response, as demonstrated by OAS1 induction. Linear constructs of uPA, uPAR, MMP-9, and cathepsin B or any combination thereof are also suitable for inducing RNAi.

siRNAs or shRNAs or hpRNAs disclose herein include nucleic acids that consist essentially of self-complementary sequences of uPA, uPAR, MMP-9, cathepsin B or a combination thereof. The loop region and the spacer (intervening regions) may vary both in the length and the sequence depending upon the target sequence, the construct, and the therapeutic use. The nucleic acid molecules disclosed herein can be appropriately modified with nucleic acid analogs, derivatives, or any suitable modification to improve stability or effectiveness of RNAi induction. The nucleic acid molecules disclosed herein can also be administered in combination with other tumor-specific immune activating agents, tumor targeting agents, and any suitable pharmaceutically acceptable carriers or adjuvants. The nucleic acid molecules disclosed herein can also be administered in conjunction with other cancer therapies such as radiation therapy, chemotherapy, and antibody therapy.

Types of brain tumors suitable for treatment include for example, acoustic neuroma, astrocytic tumours, CNS lymphoma, ependymoma, hemangioblastoma, medulloblastoma, meningioma, mixed gliomas, oligodendroglioma, pineal region tumours, and pituitary tumours.

Suitable cancers that are amenable to treatment described herein include lung cancer, bladder cancer, melanoma, breast cancer, non-hodgkin's lymphoma, colon and rectal cancer, pancreatic cancer, endometrial cancer, prostate cancer, kidney (renal cell) cancer, skin cancer (non-melanoma), leukemia, and thyroid cancer.

Pharmaceutical either comprising the nucleic acids described herein or consisting essentially of the nucleic acids described herein can be directly administered as nucleic acids or administered as part of a viral delivery vehicle or any other suitable carrier. Suitable dosages include for example 0.1-1.0 μg/kg body weight, 1-10 μg/kg of body weight, 10-100 μg/kg of body weight. Other suitable doses include for example 1-10 mg/ml or 10-100 mg/ml. A suitable dose is a therapeutically effective amount of the nucleic acids disclosed herein that reduce tumor growth or shrink preexisting tumors. The compositions can be administered by any conventional means available for use in conjunction with pharmaceuticals, either as individual therapeutic active ingredients or in a combination of therapeutic active ingredients. They can be administered alone, but are generally administered with a pharmaceutical carrier selected on the basis of the chosen route of administration and standard pharmaceutical practice. Suitable routes include oral, intraperitoneal, muscular, intramuscular, intravenous, buccal, subcutaneous, sublingual, and topical routes. For injection, the therapeutic compositions can be formulated in liquid solutions, preferably in physiologically compatible buffers such as Hank's solution or Ringer's solution. In addition, the therapeutic compositions may be formulated in solid form and redissolved or suspended immediately prior to use. Lyophilized forms are also included.

The therapeutic compositions may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The intervening sequences that separate a plurality of target sequences as part of the RNAi construct may range from about 22-35 base pairs, about 25 base pairs, about 30 base pairs, about 50-60 base pairs, about 65 base pairs, about 67 base pairs, about 21-70 base pairs, and about 20-100 base pairs.

EXAMPLES

The following examples are for illustrative purposes only and are not intended to be construed to limit the scope of the disclosure.

Example 1

Endogenous uPA and uPAR Protein Expression is Associated with In Vitro Invasiveness of Human Prostate Cancer Cells PC3 cells are highly metastatic, whereas DU145 and LNCaP cells are moderately and poorly metastatic, respectively. uPA and its receptor uPAR are involved in tumor invasion and metastasis. The levels of these proteins in the three human prostate cancer cell lines with different metastatic potentials were compared As shown in FIG. 1A, uPA and uPAR protein levels were significantly higher in PC3 and DU145 cells as compared with the poorly metastatic LNCaP cells, which expressed undetectable levels of these proteins.

Figure 1:
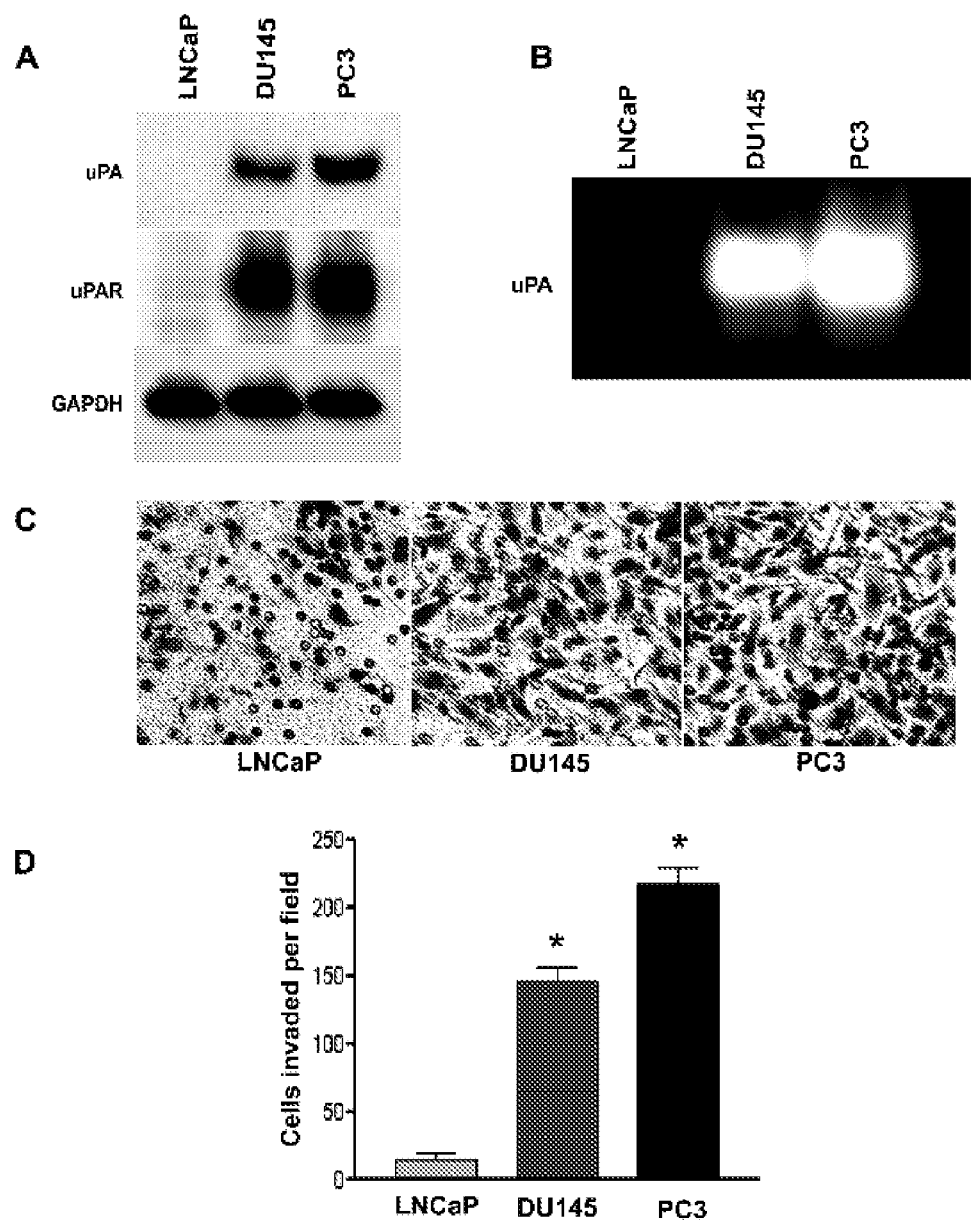
FIG. 1 shows that uPA and uPAR protein expression levels and uPA activity correlate with invasive potential of human prostate cancer cell lines. Endogenous uPA and uPAR protein expression was examined by immunoblot analysis of total cellular protein isolated from the following prostate cancer cell lines: LNCaP, DU145 and PC3. Equal amounts of isolated protein from cell extracts of all three cell lines were subjected to immunoblot with anti-uPA, anti-uPAR and anti-GAPDH antibodies. GAPDH was utilized as a loading control (A). uPA activity in prostate cancer cell lines was assessed by fibrin zymography. Equal amounts of protein from prostate cancer cells in serum-free media were separated by SDS-PAGE on 10% gels containing fibrinogen and plasminogen under non-reducing conditions. After exchange of SDS with Triton X-100 washing, the gel was incubated in glycine buffer (0.1 M, pH 8.0). Fibrinolytic activity was detected as clear lysis bands after amido black staining and subsequent destaining with methanol-acetic acid (B).

A similar trend was seen in uPA activity as assessed by fibrin zymography (FIG. 1B). Thus, uPA and uPAR protein levels as well as uPA activity were positively correlated with their known metastatic potential. The ability of the prostate cancer cells to invade Matrigel, a gel layer composed of basement membrane proteins, was examined. This assay is a well-established in vitro model for assessing tumor invasiveness. The highly metastatic prostate cancer cell line PC3 showed the greatest levels of invasiveness followed by the DU145 and LNCaP cell lines, an order consistent with their known metastatic potentials (FIGS. 1C and 1D). PC3 cells were 14-fold more invasive and DU145 were 9-fold more invasive than LNCaP cells. A strong correlation between uPA and uPAR protein levels and the invasive ability of human prostate cancer cells with differing metastatic potentials was demonstrated. PC3 and DU145 cell lines were more invasive than LNCaP cells, consistent with their known metastatic potentials. A strong correlation exists between the expression patterns of uPA and uPAR and the invasive potential of prostate cancer cell lines used (FIG. 1). Enhanced uPA and uPAR expression in prostate cancer cell lines is associated with increased invasiveness and metastatic potential.

Example 2

Figure 2A:
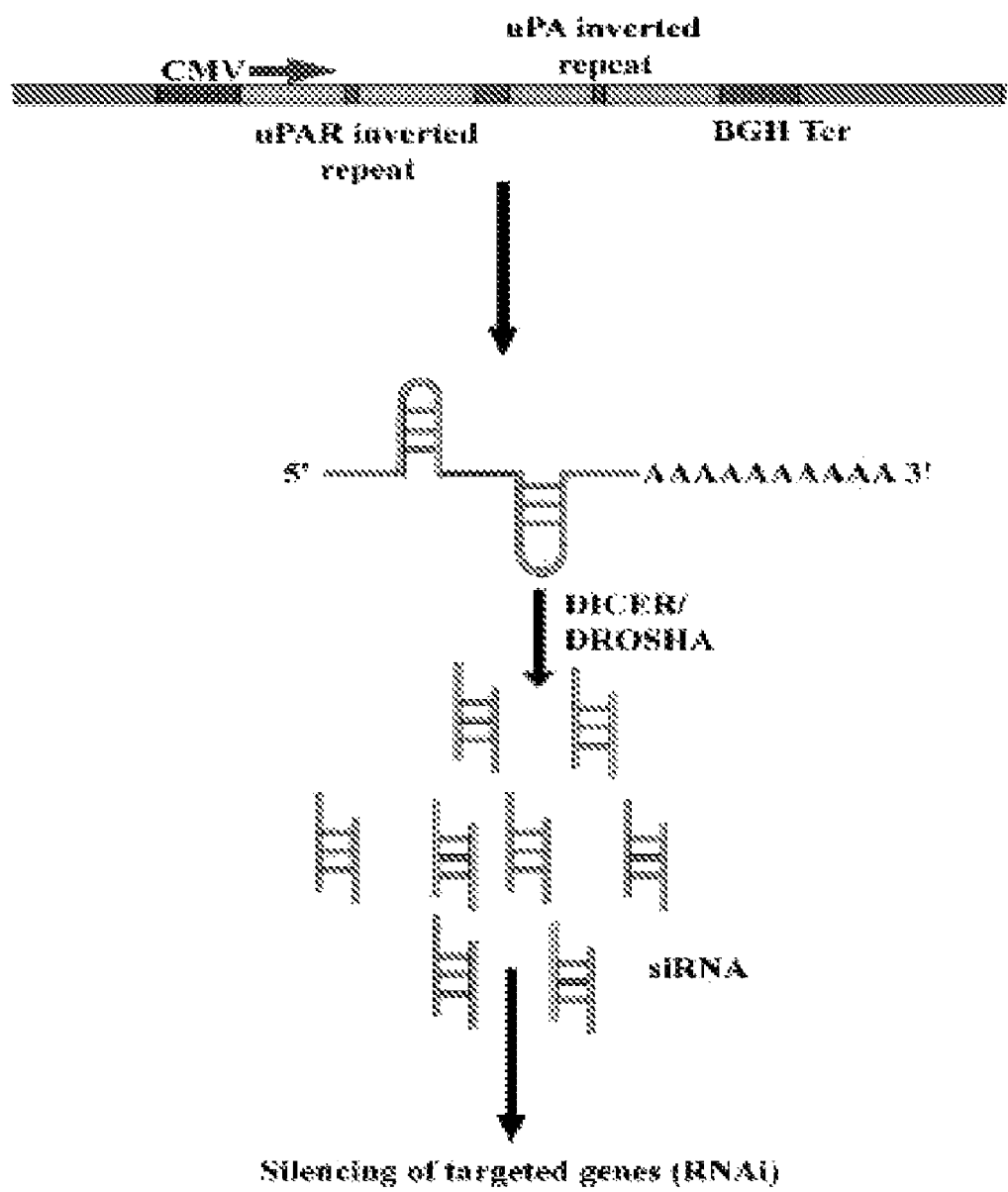

Efficient Knockdown of uPA and uPAR Gene Expression in Human PC3 Prostate Cancer Cells Using RNAi Biological role of uPA and uPAR in prostate tumor progression was investigated using small hairpin RNAs to knockdown endogenous uPA and uPAR gene expression in the human prostate cancer cell line PC3, which expresses uPA and uPAR as well as a high metastatic potential. pcDNA3-CMV vectors were developed containing small hairpin constructs capable of generating 19 or 21-nt duplex RNAi oligonucleotides corresponding to either uPA or uPAR. Also, a single bicistronic construct driven by cytomegalovirus (CMV) promoter to deliver dual small hairpins targeted against both uPA and uPAR was constructed to test the effectiveness of simultaneously inhibiting expression of two endogenous genes (FIG. 2A). The vectors expressing shRNAs for uPA, uPAR and the uPA-uPAR combination were transfected into PC3 cells.

Figure 2B:
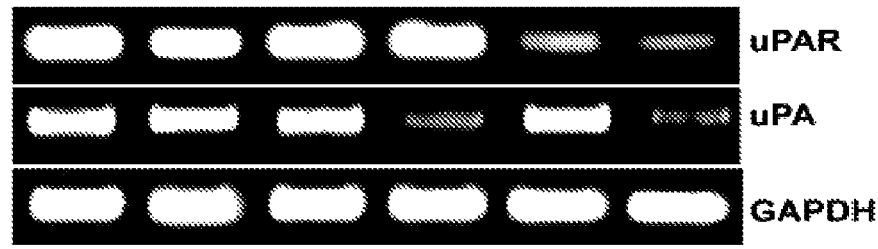
Figure 2C:
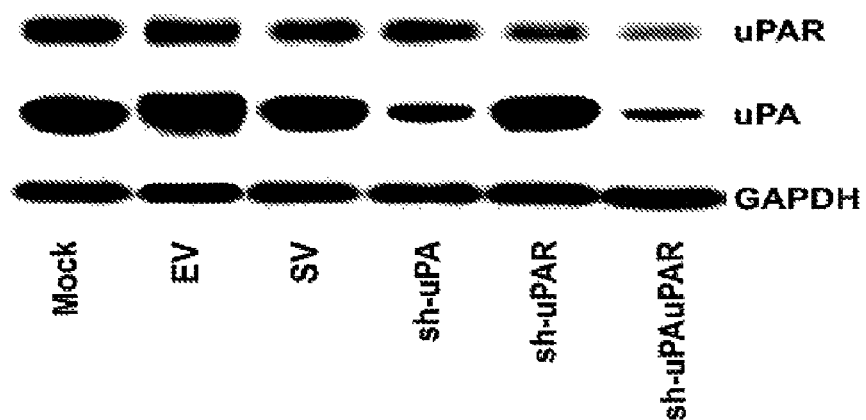

As shown in FIG. 2B, analysis of the shRNA-transfected cells for uPA and uPAR expression via semi-quantitative reverse transcription-PCR demonstrated a specific reduction in mRNA levels for each gene relative to the EV/SV-transfected cells or mock cells. However, the RNAi effect was more with the shRNA vector simultaneously targeting uPA and uPAR (FIG. 2B). Immunoblot analysis of cell extracts was carried out to determine whether decreased mRNA expression, as observed, correlated with decreased translation of the gene product. A similar trend was observed by immunoblot assay as well (FIG. 2C). No effects of RNAi were observed on the expression of GAPDH, which was used as an internal control for specificity and loading at mRNA level as well as protein level. In addition, EV/SV-transfected cells also showed that RNAi-directed uPA and uPAR knockdown is specific (FIGS. 2B & 2C).

Figure 2D:
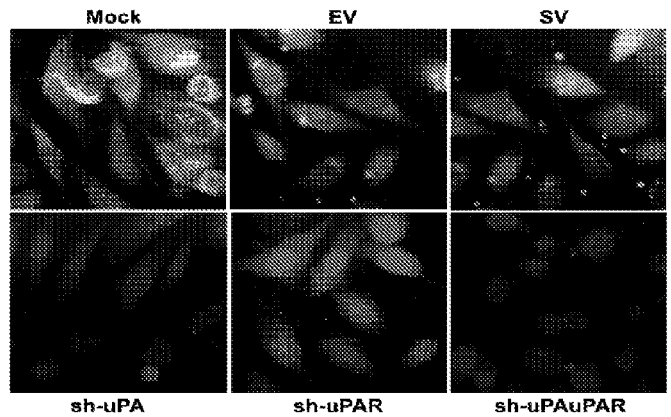

In addition, the effects of gene-specific shRNAs on uPA and uPAR protein expression were detected in PC3 cells using double immunostaining with anti-uPA and anti-uPAR antibodies. As shown in FIG. 2D, uPA and uPAR staining was drastically reduced by gene-specific shRNAs in comparison to EV/SV-transfected cells. uPA and uPAR double immunostaining was totally diminished in cells transfected with sh-uPAuPAR (FIG. 2D). In contrast, the PC3 cells transfected with EV and SV exhibited a similar staining intensity and pattern as the mock cells. These immunofluorescence studies confirmed the RT-PCR and immunoblot analyses.

Simultaneous inhibition of two genes using a plasmid-based siRNA system is a useful tool. RNAi effectively down-regulated uPA and uPAR mRNA as well as protein expression in the prostate cancer cell line PC3 (FIGS. 2B and 2C). These gene-specific RNAi plasmids reduced uPA and uPAR expression substantially compared to mock or EV/SV-transfected cells. Immunohistochemical staining data showed that mock or cells transfected with EV/SV revealed positive staining for uPA and uPAR, while the cells transfected with sh-uPAuPAR were barely stained, with the exception of DAPI nuclear staining, suggesting the knockdown of uPA and uPAR protein expression (FIG. 2D). Similarly, the intensity of immunostaining for uPA and uPAR was reduced by gene-specific RNAi.

Example 3

Knockdown of uPA and uPAR Expression by RNAi Inhibited Matrigel Invasion of PC3 Cells One of the functions of uPA and uPAR is promotion of invasion, a process necessary for tumor metastasis. The impact of uPA and uPAR knockdown on PC3 cellular invasion was evaluated by a Matrigel invasion assay using the shRNA-transfected cells. When compared with mock cells or cells transfected with EV/SV, sh-uPAuPAR-transfected cells showed a substantial reduction in invasive capacity (FIG. 3A). Invasion of PC3 cells was reduced to 75% of that of the controls (i.e., mock or EV/SV-transfected cells) by sh-uPA and to 90% by sh-uPAuPAR (FIG. 3B). Although knockdown of uPAR alone did not show a significant decrease in invasion, knockdown of uPA as well as uPAR had a significant effect (FIGS. 3A & 3B), suggesting that PC3 cell invasion into matrigel is substantially regulated by coordinated function of uPA and uPAR. These results show that uPA and uPAR expression is required for prostate cancer invasion as well as metastasis. The sh-uPAuPAR effect was significant that the cells could hardly invade through the matrigel membrane, suggesting that RNAi had significantly interfered with the uPA-uPAR system mediating proteolytic activity and cell viability.

Example 4

Figure 4A:
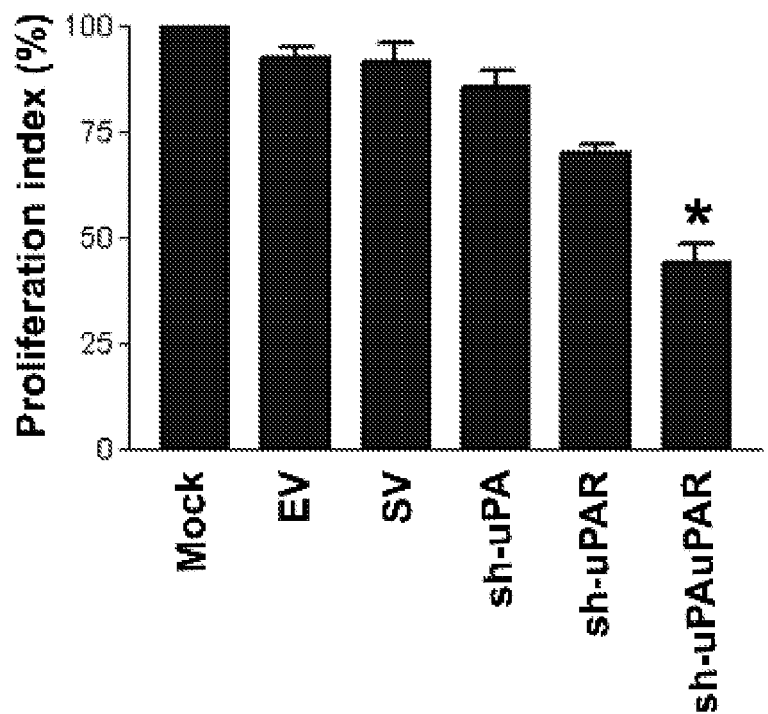

Knockdown of uPA and uPAR Expression by RNAi Inhibits Cell Proliferation and Induces Apoptosis The effects of RNAi-mediated uPA and uPAR silencing on cell proliferation and survival were examined by MTT analysis 72 h after transfection with sbRNA-specific to uPA and uPAR (FIG. 4A). RNAi-targeting against uPA had no effect on the proliferative ability of PC3 cells, whereas RNAi-specific to uPAR had a low inhibitory effect. In contrast, a dramatic reduction in proliferation of PC3 cells was observed with RNAi simultaneously targeting uPA and uPAR (FIG. 4A). The percentages of viable cells were reduced in the presence of uPAR and uPA-uPAR RNAi by approximately 30% and 60% on average, respectively, as compared to the control cells. These results suggest that increased uPA and/or uPAR levels in tumor cells might endow cells with enhanced growth and survival capacity. As such, reducing uPA and uPAR levels may induce apoptosis in cancer cells.

To examine this possibility, PC3 cells were transformed with plasmids expressing sh-uPA, sh-uPAR or sh-uPAuPAR.

Figure 4B:
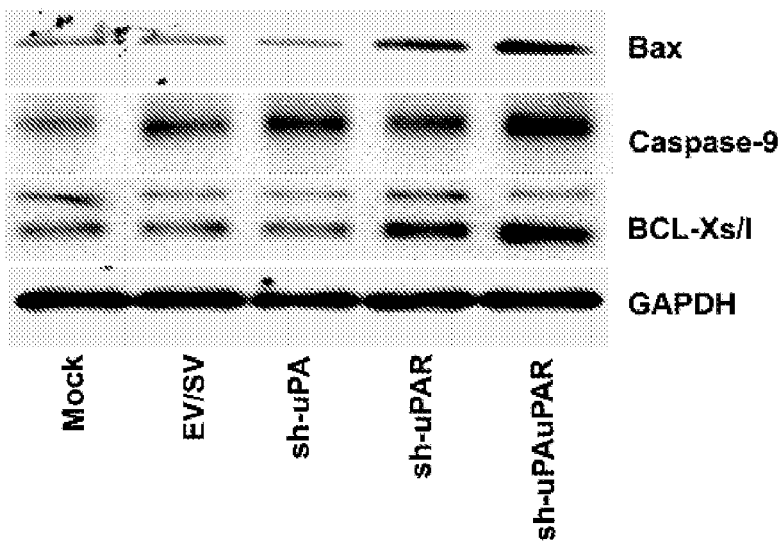
Figure 4C:
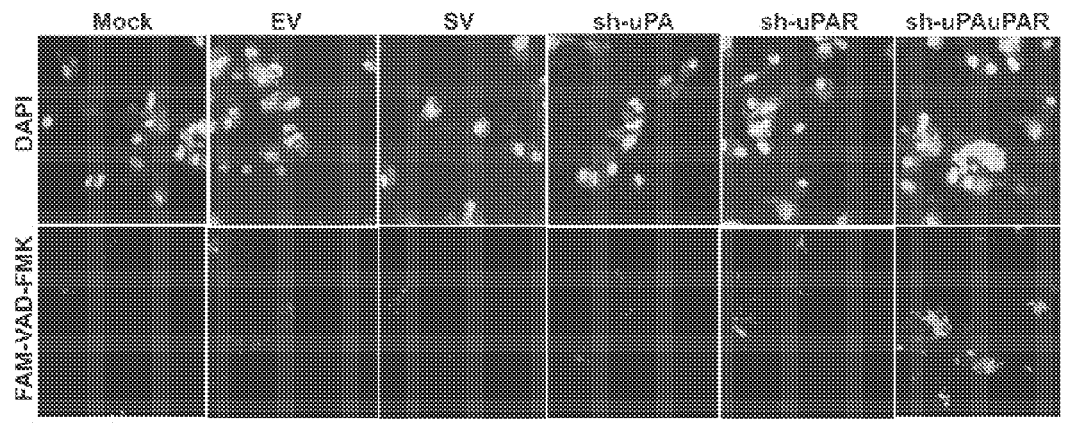
Figure 4D:
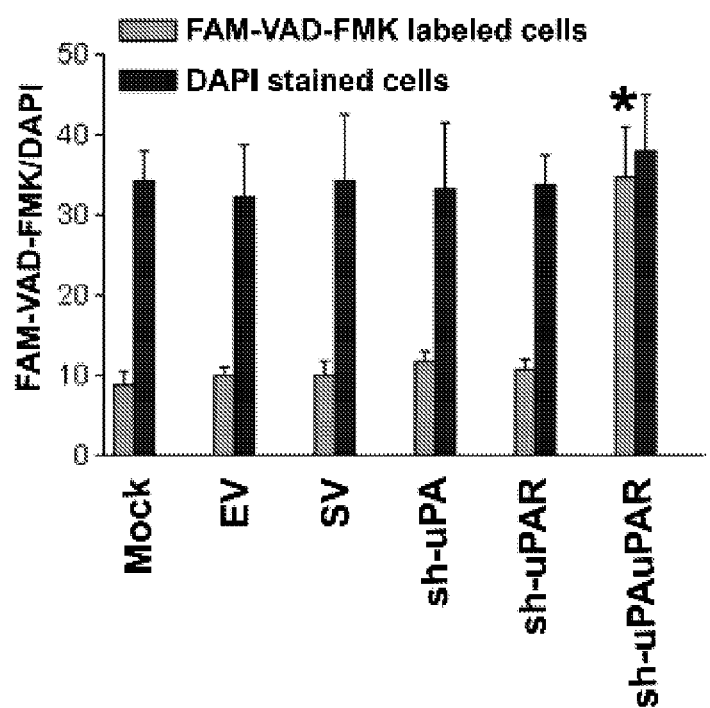
Figure 4E:
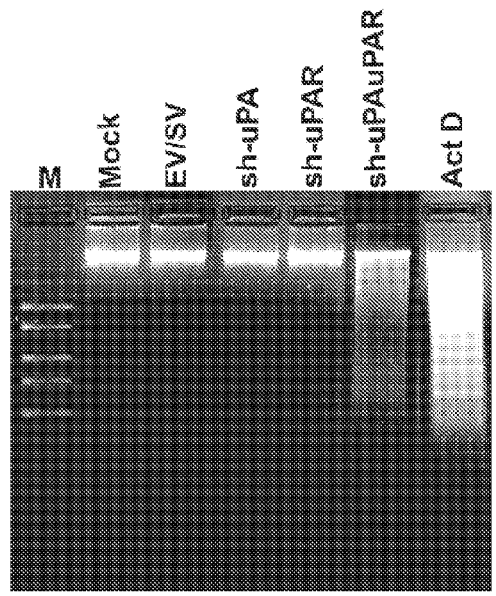

Molecular analysis of PC3 cell protein extracts revealed that the sh-uPAuPAR transfection induced pro-apoptotic genes, including Bax, Bcl-$X_{S/L}$, caspase 9 (FIG. 4B). Also, fluorescent dye staining of sh-uPAuPAR-transfected PC3 cells with FAM-VAD-FMK revealed enhanced caspase activity which was not detected in either the mock cells or EV/SV-transfected cells (FIGS. 4C & 4D). DNA fragmentation analysis provided further evidence of apoptotic induction. As FIG. 4E indicates, sh-uPAuPAR-transfected PC3 cells exhibited DNA laddering, a typical hallmark of apoptosis, on agarose gel electrophoresis that was not detected in either mock or EV/SV-transfected cells. This DNA laddering was similar to that of apoptosis induced by actinomycin D treatment (FIG. 4E), thereby confirming that the observed cell death was a result of apoptosis. In addition, DNA laddering was not observed in cells transfected with either sh-uPA or sh-uPAR. These results are also in agreement with caspase 9 induction and enhanced caspase activity in general as determined by FAM-VAD-FMK.

Example 5

Knockdown of uPA and uPAR Expression by RNAi Inhibits its Downstream Signaling and Tumorigenesis in Nude Mice The biological consequences due to uPA and uPAR silencing may be a result of changes in uPA-uPAR-mediated signaling and subsequent downstream functions. Since increased expression of uPA and uPAR activates ERK1/2 signaling, the status of mitogen-activated protein kinases in uPA-uPAR knockdown cells was examined. Immunoblot analysis shows that ERK 1/2 phosphorylation was completely abolished in the sh-uPAuPAR-transfected cells, but not in the control cells (FIG. 5A). The ERK phosphorylation did not change in cells transfected with either sh-uPA or sh-uPAR. The total, including phosphorylation, activity of Stat 3 was substantially suppressed in cells transfected with sh-uPAuPAR when compared with control cells (FIG. 5B). Furthermore, electrophoretic mobility shift assay (EMSA) with nuclear extracts from cells transfected with sh-uPAuPAR demonstrated that knockdown of uPA and uPAR expression inhibited binding of the extracts to the labeled Stat 3 binding sites (FIG. 5C). Since Stat 3 activation contributes to the stimulation of the anti-apoptotic pathway, the reduced level of phospho-Stat 3 as well as DNA binding activity may explain the increased susceptibility of sh-uPAuPAR-transfected PC3 cells to apoptotic cell death. Alternatively, constitutive ERK activation may contribute to cell survival.

Whether uPA-uPAR RNAi would also suppress the tumorigenicity of pre-established PC3 orthotopic tumors in nude mice was investigated. PC3 cells were inoculated intraprostatically in the lateral lobe of prostate. On days 7 and 14 post-implantation, the tumors were injected with plasmid constructs expressing sh-uPA, sh-uPAR or sh-uPAuPAR. The mice were then sacrificed 14-15 days after the second dose of RNAi treatment, as was necessitated by the morbidity resulting from the tumors that had formed in control groups. The gross morphology of primary tumors and sites of metastasis were examined (FIG. 6A). No secondary tumors were observed visually in mice treated with the sh-uPA, sh-uPAR and sh-uPAuPAR plasmids, whereas mice treated with EV, SV and mock presented with secondary tumors in addition to the primary tumor within the prostate gland (FIG. 6A). Tumors were dissected and weighed (FIG. 6B). A 90-100% incidence of primary as well as secondary tumors was observed in mock, EV and SV-treated groups. Although sh-uPA and sh-uPAR treatments did not inhibit tumor growth completely, the weights of the tumor masses formed from these treatments groups were smaller than tumors from the control treatment groups (FIG. 6B). A significant reduction in tumor weight was observed in mice treated with sh-uPAuPAR. Immunoblot analysis for protein levels in tumor samples confirmed that the tumors treated with sh-uPAuPAR had significantly decreased uPA and uPAR levels (FIG. 6C). Further 150 µg of sh-uPAuPAR completely regressed the pre-established prostate cancer.

Immunohistochemical analysis was performed on the harvested paraffin-embedded tumor tissues to assess the effects of sh-uPAuPAR on the in vivo behavior of PC3 cells. sh-uPAuPAR-directed RNAi expression did not change the general architecture of the prostate gland and H&E staining showed largely normal histology, whereas staining revealed both tumor and host cells in the control groups. RNAi-targeted against either uPA or uPAR alone slightly reduced tumor cells relative to the control groups. Presumably, there was no in vivo rescue from the uPA-uPAR RNAi induced apoptosis. To test this, the paraffin-embedded tumor sections from all treatment groups were stained for apoptotic markers using Klenow-FragEL DNA fragmentation analysis. This end labeling for apoptotic cells demonstrates significant differences between treatment groups. Tumors of mock, EV and SV-treated groups showed generalized, low level staining for FragEL, therefore indicating that the tumor cells were healthy. In contrast, most of the areas of the sh-uPAuPAR-treated PC3 prostate tumors were positive for Klenow staining.

Intratumoral coinjection of sh-uPA and sh-uPAR also resulted in almost complete regression of pre-established prostate tumor growth, whereas control groups of mock, EV and SV show reproducible and significant tumors (FIGS. 7A & 7B). Immunoblot analysis demonstrated the selective knockdown of uPA and uPAR protein levels in tumors cotreated with sh-uPA and sh-uPAR constructs (FIG. 7C). This cotreatment exhibited largely normal histology by H & E staining while tumors of mock, EV and SV treated groups displayed observable change in the general architecture of the prostate gland and H & E staining showed both tumor and host cells (FIG. 7D). The knockdown of uPA and uPAR via cotreatment also resulted in a significant induction of apoptotic cell death, as revealed by positive Klenow staining (FIGS. 7E & 7F). When combined with the data presented in FIGS. 6A-C and 7A-F, these results show that treatment with sh-uPAuPAR, however, has potent RNAi effect when compared to cotreatment with sh-uPA and sh-uPAR, which causes significant reduction in established tumor size.

The results of the in vitro DNA laddering analysis and an in vivo DNA fragment end-labeling assay show that the simultaneous knockdown of uPA and uPAR by shRNA-based RNAi induces apoptosis. uPA-uPAR-mediated downstream signaling is an excellent target for the treatment of hormone-independent prostate cancer. uPA-uPAR-mediated downstream signaling is likely required for cell invasion, survival and proliferation in the prostate cancer cell line PC3.

Example 6 uPA and uPAR Functional Signaling and Their Role in Tumorigenesis

Aberrant expression of uPA and uPAR was found to be one of the most frequent alterations in advanced stage prostate cancer. The fact that uPA and uPAR are overexpressed only in the advanced stage of prostate cancer suggests that uPA and uPAR affect the functional pathways that are relevant in determining the phenotypes of advanced stage of cancers, such as increased proliferation and invasion. Invasion through the extracellular matrix is a characteristic step in tumor metastasis. Abrogation of either uPA or uPAR expression to suppress tumorigenesis has been achieved using several different approaches. Coupling of uPA with uPAR orchestrates several different signaling molecules that form a unique network of several different types of biological responses, such as proliferation, migration, invasion, angiogenesis and metastasis. These biological responses to uPA-uPAR binding seem to be highly specific to cell-type, the nature of the downstream signaling molecule and the level of its expression. Binding of uPA with uPAR activates ERK 1 and 2 and that this induced ERK activity is required for uPA-induced MCF-7 breast cancer cell migration. A signaling cascade including FAK, Src and Shc is responsible for uPA-induced ERK activation and cell migration. In contrast, uPA-induced vascular smooth muscle cells (VSMC) migration and proliferation required activation of Stat pathway. In human breast cancer cells uPA-induced mitogenic activity requires activation of both Stat and ERK pathways. Antisense uPA inhibited PI3K/Akt signaling and sensitized cells to apoptosis by staurosporine in the glioblastoma cell line SNB 19. Binding of uPA with uPAR likely activates signaling cascades in order to regulate cell migration, invasion, proliferation and survival.

RNAi for uPA-uPAR in PC3 cells showed remarkable suppression of invasion and proliferation as well as induction of apoptosis (FIGS. 3-4). Suppression of the uPA-uPAR system and downstream signaling molecules (ERK and Stat 3) was observed in sh-uPAuPAR-transfected PC3 cells but not in mock or EV/SV-transfected cells (FIG. 5). This suggests that all of the observed phenotypic changes in these cells were mediated by suppressing the uPA-uPAR interaction and the phosphorylation status of its downstream molecules. uPA-uPAR signaling stimulates the both the Stat and ERK pathways and protects cancer cells from death. Several lines of evidence have shown that both ERK and Stat 3 pathways are capable of protecting cells from apoptotic cell death. Transfection with either sh-uPA or sh-uPAR did not trigger apoptosis in PC3 cells (FIG. 4). this may be because blocking either uPA or uPAR alone may not sufficiently affect the downstream signaling molecules ERK and Stat 3.

Since uPA-uPAR signaling modulates ERK and Stat 3 expression, simultaneous inhibition of uPA and uPAR may impair these pathways, leading to growth inhibition and induction of apoptosis. uPA-uPAR system likely functions as a positive regulator of cell survival by facilitating cell proliferation and survival, the two hallmarks of cancer. Therefore, when overexpressed in cancers, uPA and uPAR endows a cancer cell with increased proliferative and/or increased resistance to apoptosis. In contrast, knockdown of uPA-uPAR expression or function should inhibit cancer cell growth and induce apoptosis. Intercepting uPA-uPAR mediated signaling via knockdown of uPA and uPAR simultaneously inhibited cancer cell growth and induced apoptosis. Of note, uPA-uPAR RNAi worked in the hormone-resistant prostate cancer cell line PC3. This suggests that the knockdown of uPA-uPAR expression by RNAi is a strategy to inhibit hormone-resistant prostate tumor growth and survival.

Orthotopic implantation of human cancer cells in nude mice more closely resembles the biological behaviors of these cells in humans, particularly in regards to the development of metastases. This has proven particularly true for human prostate cancer cells, which form primary tumors and metastases with much lower efficiency when implanted ectopically in nude mice. A shRNA-based RNAi plasmid system represents a strategy that can effectively suppress uPA-uPAR expression in orthotopic prostate tumors as determined by immunoblot analysis (FIG. 6C). Furthermore, the in vivo treatment of pre-established orthotopic tumors with sh-uPAuPAR-directed RNAi demonstrated a near total inhibition of tumor growth, whereas only partial reduction was observed with either sh-uPA or sh-uPAR RNAi (FIG. 6B). In addition, the co-treatment of pre-established orthotopic tumors with sh-uPA and sh-uPAR also almost completely inhibited the tumor growth (FIG. 7). No deleterious effects were noted in RNAi-treated animal groups as compared with mock or EV/SV-treated groups. Moreover, this approach can target a wide variety of tumor types and inhibit uPA-uPAR-dependent malignant phenotypes in vitro as well in vivo. Therefore, this RNAi system provides a powerful new therapeutic tool and also to analyze uPA-uPAR downstream signaling pathways as well as offers treatment options for cancer intervention with clinical relevance. Furthermore, RNAi provides a novel, convenient and selective way to interfere with uPA-uPAR expression and to study the biological significance of their signaling in cancer biology.

Despite advances in understanding of the molecular mechanisms of human cancer, developing therapeutic approaches for the clinical treatment of human malignancies remains a major challenge. Knockdown of uPA-uPAR expression significantly inhibited the growth of PC3 cells in vitro as well as in vivo and ultimately resulted in apoptotic cell death. Distinct target genes (ERK and Stat 3) were regulated downstream of the uPA-uPAR signal. PC3 cells demonstrated low Stat 3 phosphorylation and ERK phosphorylation was totally abolished when transfected with sh-uPAuPAR. RNAi for uPA-uPAR induced cell death in PC3 cells in vitro as well as in vivo.

Example 7

Plasmid-Based CMV Promoter Driven 21 bp Inverted Repeats Targeted to uPAR and MMP-9 are Processed to siRNA To determine whether the CMV promoter-driven transcript (uPAR and MMP-9 targeted) is processed correctly to siRNA, SNB19 cells were transferred with control/EV, SV, puPAR, pMMP-9 and pUM. FIG. 8 illustrates a schematic representation of the construct. Cells were also transfected with an unrelated construct targeting GFP in non-GFP cells to determine the processing of the RNA transcript to siRNA, and confirm the fact that the results obtained are not just degradation products of the target gene. Non-GFP SNB 19 cells transfected with pGFP resulted in the processing of the RNA transcript to siRNA (FIG. 9A). Similarly, cells transfected with puPAR, pMMP-9 and pUM resulted in the processing of the RNA transcript to the appropriate siRNA. EV transfected cells did not produce any siRNA-like fragment targeting uPAR or MMP-9 indicating that the siRNA fragment seen is processed from the inverted repeat loops incorporated in the construct. SV transfected cells also did not produce any siRNA-like fragment targeting uPAR or MMP-9; SV consisted of an imperfect inverted repeat sequence with no homology to any known gene. When probed with a 21b sense oligo for SV, no 21 bp DNA:RNA hybrid was seen indicating that this construct did not process to siRNA-like fragments.

SNB 19 cells transfected with pUM caused the down regulation of both uPAR and MMP-9 mRNA. To determine whether the plasmid construct containing inverted 21 base pair sequences homologous to uPAR and MMP-9 would induce RNAi, SNF19 cells were transfected with control/EV, SV, puPAR, pMMP-9 and pUM. Total RNA was isolated from the transfected cells and the first strand cDNA was synthesized using a cDNA synthesis kit (Invitrogen). The cDNA was then subjected to PCR according to standard protocols known to those of skill in the art. Using specific primers for uPAR, MMP-9, and GAPDH (see Table 1) in cells transfected with control/EV and SV, there was no reduction in the levels of uPAR or MMP-9; whereas in cells transfected with puPAR and levels of uPAR, mRNA was reduced significantly, and the levels of MMP-9 mRNA were not changed. In cells transfected with pMMP-9, the levels of MMP-9 mRNA were reduced, whereas the levels of uPAR mRNA were not changed indicating the specificity of the vectors to target molecules. Cells transfected with pUM showed a decrease in both uPAR and MMP-9 mRNA levels. GAPDH levels did not change (FIG. 9B).

Example 8

Inhibition of MMP Activity and uPAR Protein Levels by RNA Interference

Figure 10A:
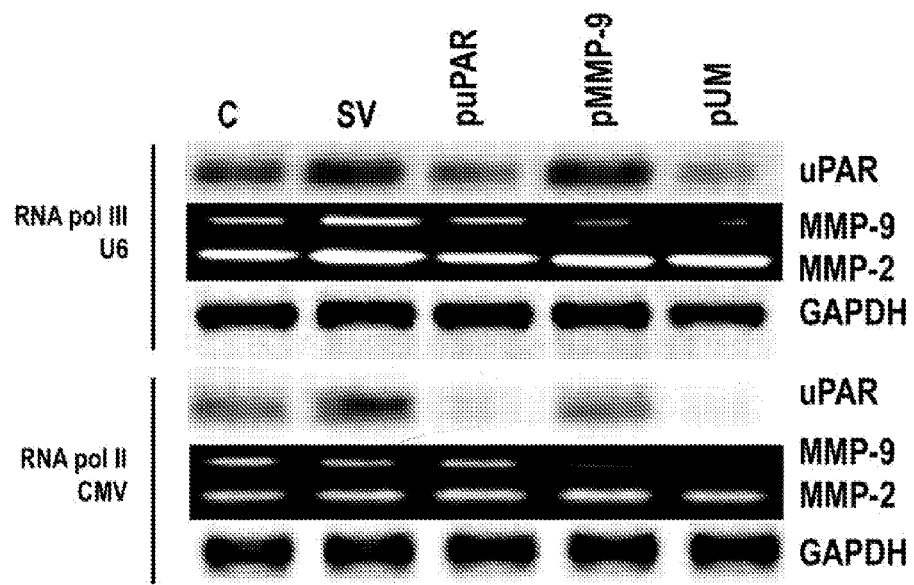
Figure 10B:
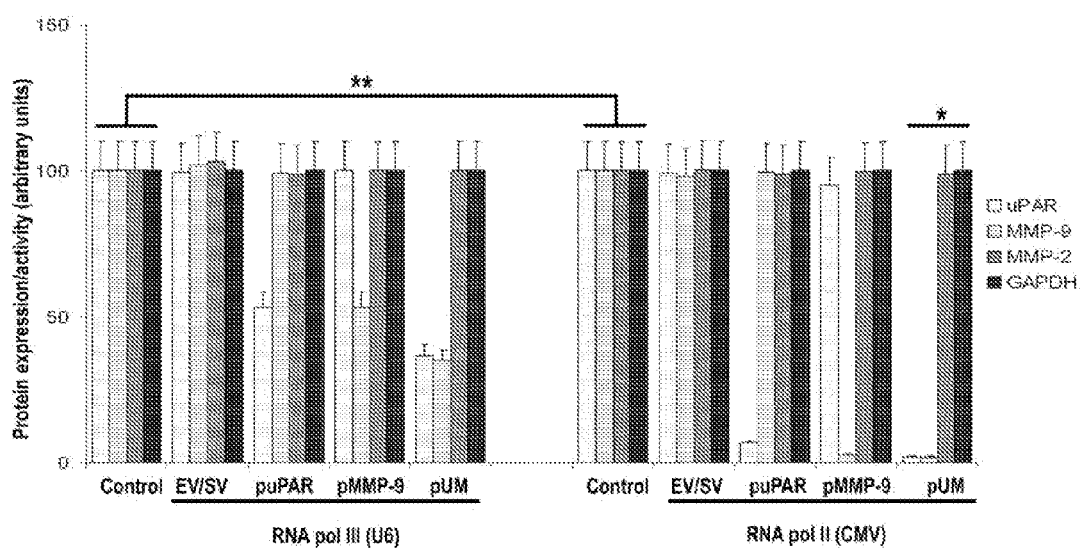

SNB19 cells were transfected with EV/SV, puPAR, pMMP-9 and pUM then determined uPAR and MMP-9 levels in cell lysates by western blotting and conditioned media by gelatin zymography respectively. SNB19 cells transfected with the pUM vector expressed decreased amounts of uPAR protein when compared to parental and EV/SV treated cells by western blotting (FIG. 10A). To determine whether this inhibitory effect was specific for uPAR, β-actin levels were assessed in the same blot. β-actin levels were similar in all the lanes confirming equal loading in all the lanes. Conditioned media from pUM-infected SNB19 cells expressed significantly low levels of MMP-9 activity compared to mock- and empty/scrambled vector-transfected cells (FIG. 10B). MMP-2 levels were not changed, indicating specific inhibition of the targeted protein. Quantitative analysis of uPAR and MMP-9 bands by densitometry revealed a significant decrease in uPAR protein (12- to 14-fold) and MMP-9 enzymatic activity (8- to 10-fold) in pUM transfected cells compared to parental and EV/SV transfected cells. Cells transfected with puPAR and pMMP-9 vectors inhibited levels of uPAR and MMP-9 (FIGS. 10A & 9B) in almost the same manner as the bicistronic construct, but the downregulation of the target molecules was more pronounced with the bicistronic construct compared to the single constructs.

Vector-mediated expression of short hairpin RNA (shRNA) for uPAR and MMP-9 can achieve effective and stable gene silencing in a glioma cell line in vitro and in vivo. RNAi-based gene silencing may be adapted to target overexpressed proteins in gliomas with significant therapeutic potential. Synthetic siRNA molecules also have the same effect in suppressing endogenous MMP-9 and uPAR levels.

Example 9

Inhibition of Cell Proliferation by siRNA for uPAR and MMP-9

The MTT assay was used to assess the effect of the siRNA vectors (EV/SV, puPAR, pMMP-9 and pUM) on proliferation of cells cultured on vitronectin-coated microplates. After 3 days of infection, the puPAR, the puPAR, pMMP-9 and pUM vector-infected SNB 19 cells showed a decrease in proliferation relative to that of parental and EV/SV transfected SNB 19 cells (FIG. 11). The pUM vector effect was much higher in SNB19 proliferation compared to the single siRNA constructs (puPAR and pMMP-9). There was no difference in proliferation between parental and EV/SV transfected SNB 19 cells.

Example 10

RNA Interference Inhibited uPAR and MMP-9 Immunofluorscence and Tumor-Induced Angiogenesis SNB 19 cells transfected with puPAR and pMMP-9 caused the down regulation of uPAR and MMP-9 protein levels as determined by immunocytochemistry respectively. Cells transfected with pUM caused the down regulation of both uPAR and MMP-9 protein levels as determined by immunocytochemistry (FIG. 12A). To determine the effect of the combined construct expressing siRNA for both uPAR and MMP-9, SNB19 cells were transfected with puPAR, pMMP-9 and pUM; cells were also transfected with EV and SV, which served as controls. From the results, it is clear that cells transfected with puPAR alone showed a down regulation of uPAR protein levels. Cells transfected with pMMP-9 showed a down regulation of MMP-9 alone, whereas cells transfected with pUM caused a down regulation of uPAR and MMP-9 protein levels, indicating that the dual construct was as efficient, if not more, at down regulating the target protein levels. To test if siRNA for uPAR and MMP-9 could also inhibit tumor-induced capillary formation, transfected and untransfected SNB19 glioma cells were co-cultured with human endothelial cells. Immunohistochemical analysis was performed using factor VIII antigen to evaluate tumor-induced vessel formation in an in vitro co-culture system and H&E staining of these co-cultures after transfection with EV/SV, puPAR or pMMP-9 and pUM. FIG. 12B shows that endothelial cells cultured with SNB19 cells formed distinct capillary-like networks in mock- and empty vector-transfected cultures within 24-48 h. In contrast, pUM-transfected SNB19 cells did not induce capillary-like network formation in endothelial cells. Quantification of the branch points and number of branches were significantly reduced in pUM transfected co-cultures compared to parental and empty/scrambled vector transfected co-culture (FIG. 12C). Further, the effect was less than 50% in puPAR and pMMP-9 vector and was less than 50% in puPA and pMMP vector transfected co-culture, when compared to parental EV/SV treated group in relation to capillary-like structure formation. Implantation of a chamber containing parental EV-transfected SNB19 cells resulted in microvessel development with curved, thin structures and many tiny bleeding spots. In contrast, implantation of SNB 19 cells transfected with the pUM vector did not result in the development of any additional microvessels (FIG. 12D).

Example 11 siRNA for uPAR and MMP-9 Inhibits Invasion of SNB19 Cells

Since siRNA expression inhibited uPAR and MMP-9, its ability to inhibit cell invasion was assessed. SNB19 cells transfected with EV/SV, puPAR, pMMP-9 and the pUM vector were allowed to invade through Matrigel-coated filters. FIG. 13A illustrates that the staining of pUM-transfected SNB19 cells was significantly less than that of the parental- and EV/SV-transfected cells. Quantitative analysis of cells showed that only 8% of pUM-transfected cells invaded compared to parental- and EV/SV-transfected cells (FIG. 13B).

Further, quantitative analysis of invasion of SNB19 cells transfected with puPAR and pMMP-9 vector invaded 25% and 50% as compared to parental and EV/SV transfected SNB19 cells (FIGS. 13A & 13B). RNAi also inhibited the invasion of SNB19 cells in a three-dimensional spheroid invasion model. FIG. 13C demonstrates that glioma spheroids transfected with mock and empty/scrambled vector attached to rat brain aggregates and progressively invaded the aggregates. However, co-cultures with pUM-transfected glioma spheroids failed to attach to rat brain aggregates and did not invade. Quantitative analysis indicated that only 2-4% of the fetal rat brain aggregates remained in the parental and EV/SV-transfected spheroids, whereas 90-95% of the fetal rat brain aggregates remained in the pUM-transfected spheroids (FIG. 13D). At 72 h, the rat brain aggregates revealed approximately 25% and 45% of invasion in the puPAR and pMMP-9 transfected co-cultures. Taken together, these findings provide strong evidence that RNAi-mediated silencing of uPAR and MMP-9 greatly inhibits glioma cell invasion in both in vitro models compared to single siRNA constructs for uPAR and MMP-9. These results showed that single siRNA constructs for uPAR was more effective than single siRNA construct for MMP-9.

Example 12

Therapeutic Effect of siRNA for uPAR and MMP-9

Figure 14A:
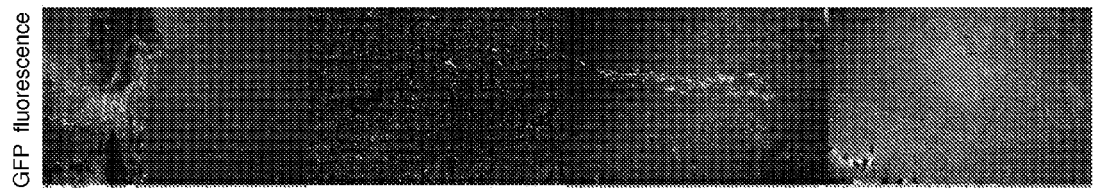
Figure 14B:
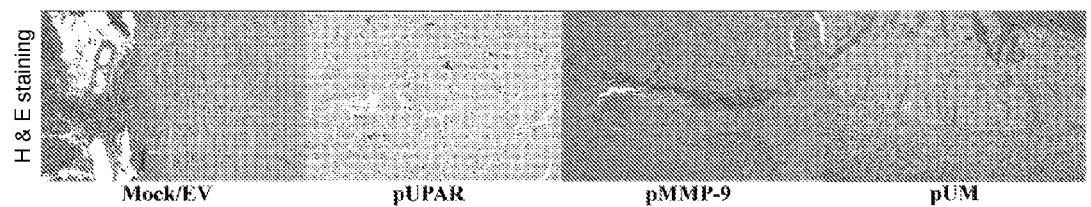
Figure 14C:
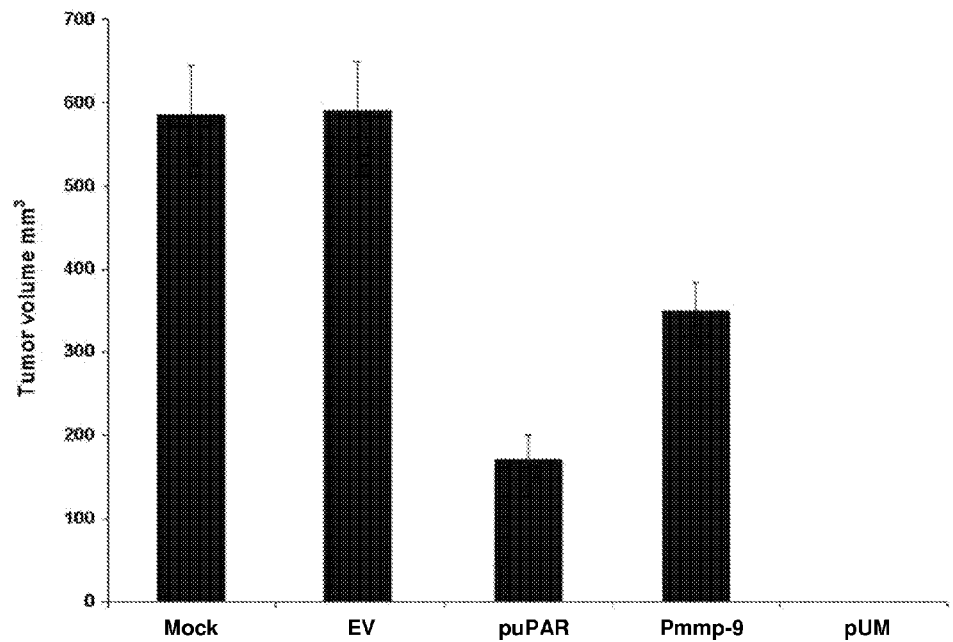

To evaluate the effectiveness of RNAi-mediated interference of uPAR and MMP-9 gene expression in tumor progression, the pUM vector was injected in tumor-bearing mice using a stereotactic pump. To facilitate the detection of invasive tumor cells, human glioblastoma cells (SNB19) were assessed with the cDNA for green fluorescent protein (SNB19-GFP). Microscopic examination of brain sections revealed that control animals receiving PBS or empty vector (EV) alone developed significant tumor growth after a 5-week follow-up period as visualized by GFP fluorescence and H&E staining of similar sections. In contrast, tumor growth or GFP fluorescence or H&E staining was not detected in animals receiving the pUM vector under the same conditions (FIGS. 14A & 14B). Quantification of hematoxylin and eosin-stained brain sections or GFP sections by a neuropathologist who was blinded as to treatment revealed no difference in tumor size between the control and empty vector treated groups; however, total regression of tumors was revealed in the pUM vector treated group (FIG. 14C). In the case of single siRNA-treated constructs for uPAR and MMP-9, pre-established intracranial tumor growth was inhibited 70% and 40%, respectively. Intraperitoneal injections of the pUM vector resulted in complete regression of pre-established intracranial tumor growth for lengthy period of 6 months. These results demonstrated that RNAi mediated suppression of uPAR and MMP-9 dramatically inhibited pre-established intracranial tumor growth.

RNAi-mediated inhibition of uPAR and MMP-9 may inhibit tumor growth in several interdependent ways. Apoptosis measured by DNA fragmentation was higher in the brains of animals injected with the antisense uPAR stable clones compared to parental cell line. The antitumor effects observed in the intracranial tumor model could be due to induction of tumor-cell death.

Tumor cells depend on angiogenesis to survive and proliferate. RNAi-mediated inhibition of uPAR and MMP-9 significantly inhibited tumor-induced in an in vitro co-culture system. The anti-angiogenic effects of the pUM vector suppressed the ability of tumor cells to recruit blood vessels necessary for survival and directed anti-invasive effects onto the tumor cells themselves. The capacity of siRNA for uPAR to block tumor progression could also include the blocking of the anti-apoptotic and angiogenic effects of uPA. In general no single anti-angiogenic agent (including angiostatin and endostatin) used as monotherapy in preclinical models is able to reduce tumor burden after tumors have reached 100 mm. It was reported that the absence of Plg, uPA, or tPA significantly decreased the development of experimental choroidal neovascularization compared with wild type or uPAR-deficient mice. This effect was suggested to be partly due to a modulation of matrix metalloproteinase activity. Although studies have demonstrated the antiangiogenic effect of synthetic MMP inhibitors, virtually all of these inhibitors lack specificity for a single MMP. For example, decreased vessel density and increased tumor cell apoptosis were observed in primary tumors and metastases in mice treated with KB-R7785, which inhibits MMP-1, -3 and -9. MMPIs have shown little clinical benefit when used as monotherapy in patients with advanced diseases. Thus, combined use of MMP inhibition with other modalities is also a strategy for cancer treatment.

Example 13 siRNA Against uPAR and MMP-9 Inhibits the Level of Phosphorylated ERK, MAPK and AKT ERK, MAPK and AKT pathways play a major role in cell proliferation and survival. Western blotting was used to compare the levels of total and phosphorylated forms of ERK, MAPK and AKT by using specific antibodies specific for these molecules after transfection of SNB19 cells with EV/SV, puPAR, pMMP-9 and pUM. There was no significant difference in the amounts of total MAPK, ERK and AKT by EV/SV, puPAR, pMMP-9 and pUM constructs (FIG. 15). But, levels of phosphorylated forms of MAPK, ERK and AKT was decreased significantly by pUM compared to EV/SV, puPAR and puPA transfected SNB19 cells (FIG. 15).

Binding of uPA to uPAR in MCF-7 cells activates ERK1 and ERK2, which are required in cell motility. In the prostate cancer cell line ($PC_3MLN_4$), hypoxia increased tumor cell invasion by up-regulating the expression of uPAR, which might be mediated through MAPK, ERK and p38 kinase signaling pathway. Further, up-regulation of uPAR expression by Bcl2 in hypoxia was mediated by SP1 DNA binding activity through ERK signaling pathway. In the absence of EGFR, an alternate pathway links uPAR to ERK. However, this pathway is silenced by EGFR expression, hence indicating the involvement of uPAR in cell motility. Stable transfection of PTEN (phosphatase and tension homologue) reduced MMP-9 secretion caused by hyaluronic acid-induced phosphorylation of focal adhesion kinase and ERK1/ERK2 signaling. Glioblastomas with EGFR VIII amplification demonstrated the highest levels of MMP-9. Transient transfection of SNB19 cells with mt ERK or mt JNK repressed MMP-9 promoter suggesting that interfering with either pathway could result in inhibiting MMP-9 expression. Regulation of MMP-9 activation by various stimuli or in different cellular settings may involve different signal transduction pathways. Inhibition of ERK by MEK-specific inhibitors blocked MMP-9 expression in breast cancer cells and decreased MMP-9 production and attenuated the in vivo invasiveness in head and neck squamous carcinoma cells. mt-ERK stable transfected cells were less invasive and significantly reduced levels of MMP-9. It has been reported that these two signaling pathways (MAPK and ERK1/2) are activated when uPA binds to uPAR pUM construct inhibits the phosphorylated forms of these signaling pathway molecules (FIGS. 15-16).

Example 14

RNAi Mediated Cancer Therapies and Delivery of siRNAs siRNA inhibition of genes such as, for example, uPAR and MMP-9 overexpression extends the list of available therapeutic modalities for the treatment of human cancer. Although antisense approaches, including antisense oligonucleotide and ribozyme technologies, are available, their efficiency is not satisfactory. RNAi-mediated inhibition of uPAR and MMP-9 completely suppressed pre-established glioma tumor growth in nude mice. Thus, RNAi is a more powerful alternative to other genetic tools such as antisense oligonucleotides and ribozyme technologies in reducing target gene expression. RNAi or RNAi-like effects were more potent than antisense effects in reducing target gene expression, also suggesting the potential applicability of RNAi. A peptide vector was used that include tumor-homing arginine-glycine-aspartic acid motif in a cyclic conformation, a DNA-binding oligo lysine and histidyl residues to facilitate delivery into the cytosol. The peptide vector can function as a carrier of siRNA. RNAi based gene therapy is a novel approach for the treatment of gliomas and other metastatic tumors, including prostate cancer, breast cancer, and melanoma.

Example 15

Figure 18A:
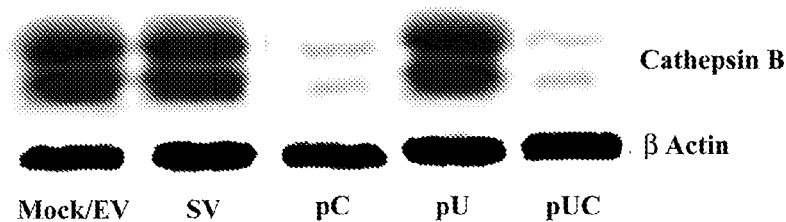
Figure 18B:
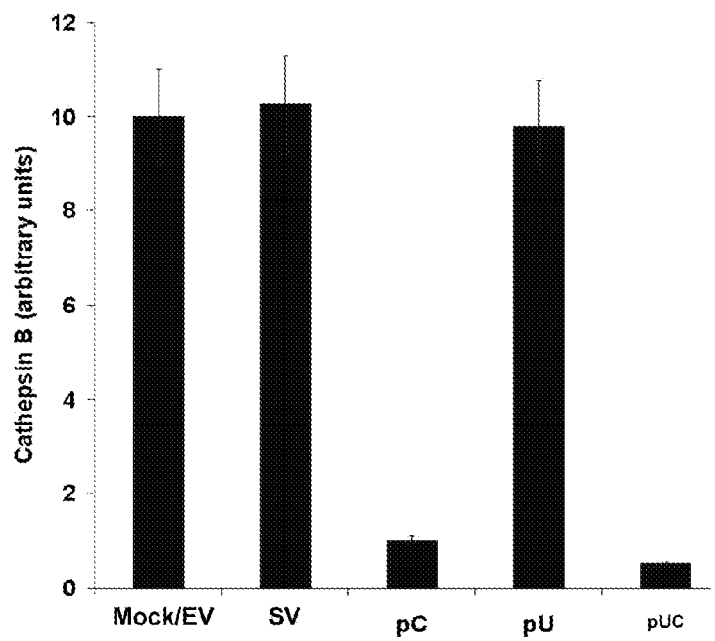
Figure 18C:
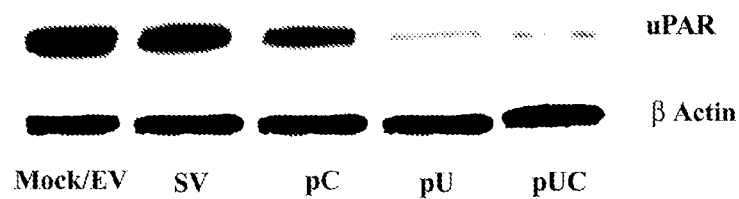
Figure 18D:
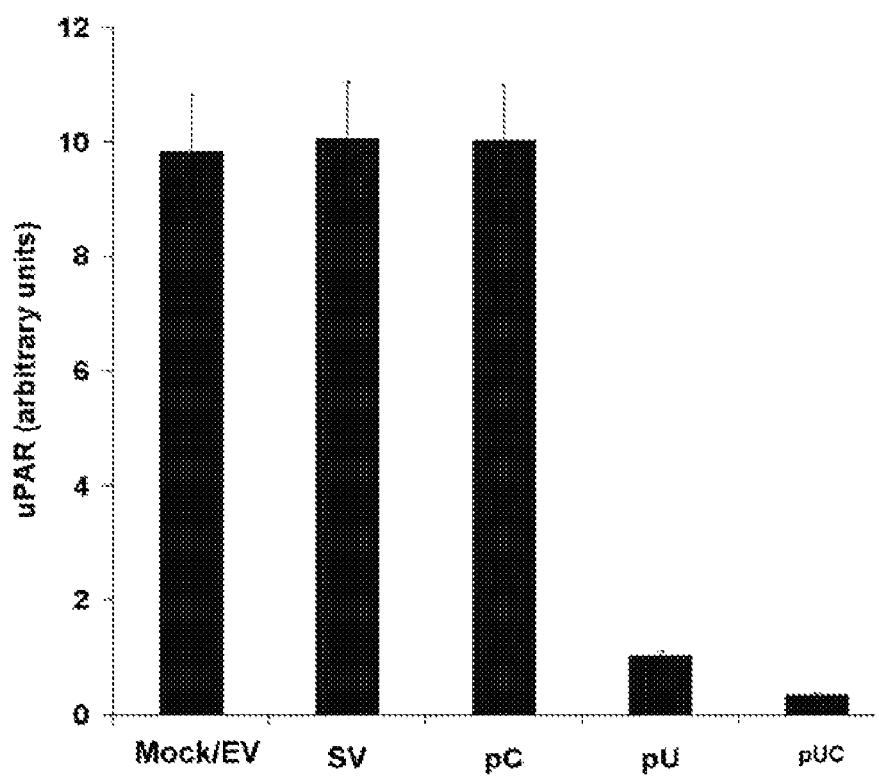

Effect of pCU Vector on Cathepsin B and uPAR Protein Levels in Total Cell Extracts RNAi targeted against proteolytic degradation is an intervention to prevent cancer cell invasion (FIG. 17). Cathepsin B and uPAR have been shown to play significant roles in ECM degradation. Transfection of SNB19 cells with the vector expressing siRNA for cathepsin B and uPAR (pCU) strongly inhibited the expression of both protein as compared to mock and empty vector (EV) controls (FIGS. 18 A & C). The levels of β-actin determined that equal quantities of protein were loaded in the gel (FIG. 18). Quantitative analysis of cathepsin B and uPAR bands by densitometry revealed a significant (P<0.001) decrease in cathepsin B (14 to 16 fold) and uPAR protein (10 to 12 fold) and in pCU transfected cells compared to mock and empty vector transfected cells (FIGS. 18B & D). Cells transfected with pU and pC vectors inhibited the levels for uPAR and cathepsin B, respectively (FIGS. 18A & C).

Example 16

Inhibition of Tumor Cell-Induced Capillary Network Formation by pCU Vector

Figure 19A:
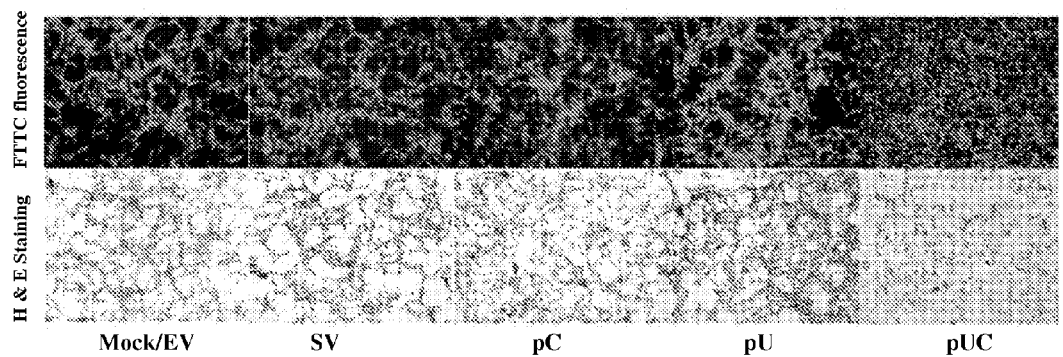
Figure 19B:
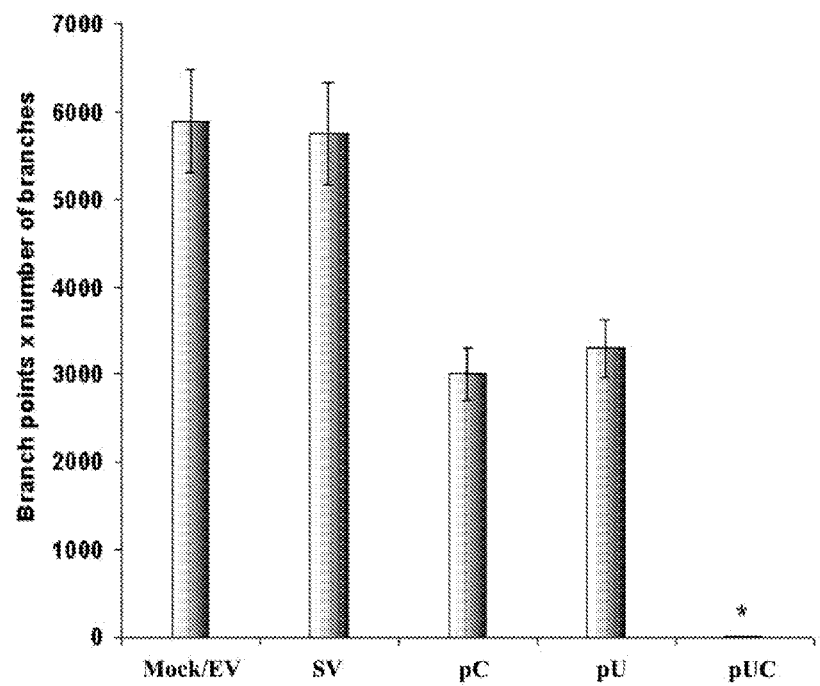
Figure 19C:
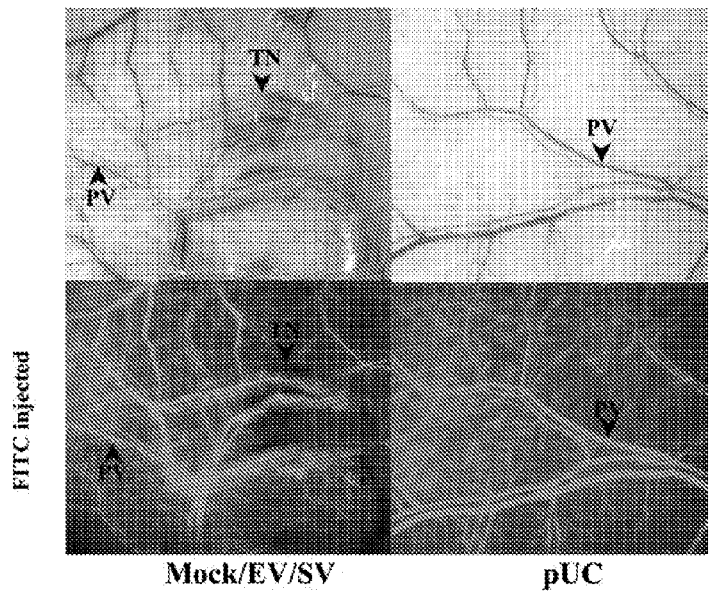

Emerging tumors are dependent on the formation of new blood vessels that fuel tumor growth. Because cathepsin B and uPAR have been reported to regulate angiogenesis, the effect of pCU on tumor cell-induced angiogenesis was assessed. Immunohistochemical analysis was performed using factor VIII antigen to evaluate tumor-induced vessel formation in an in vitro co-culture system and stain H & E for endothelial cells grown in the presence of conditioned media of SNB 19 cells after transfection with mock, empty vector, pC, pU or pCU. The results demonstrate that endothelial cells form capillary-like structures in the presence of mock and empty vector-transfected cells within 48 h; whereas, the pCU vector significantly inhibited tumor cell-induced capillary-like network formation (FIG. 19A). The quantification of the branch points and number of branches were undetectable in pCU transfected co-cultures compared to mock and empty vector (FIG. 19B). Further, the effect was less than 50% in pC or pU treated co-cultures when compared to pCU vector in relation to capillary-like structures. To confirm the in vitro co-culture experiments, whether the pCU vector can inhibit tumor angiogenesis was examined in vivo as assessed by the dorsal chamber model. Implanted chambers containing mock and empty vector (EV)-transfected SNB19 cells resulted in the development of microvessels (as indicated by arrows) with curved thin structures and many tiny bleeding spots. In contrast, implanted chambers of SNB19 cells transfected with the pCU vector did not result in the development of any additional microvessels (FIG. 19C).

Example 17

Inhibition of Migration of SNB19 Spheroids by siRNA

Figure 20A:
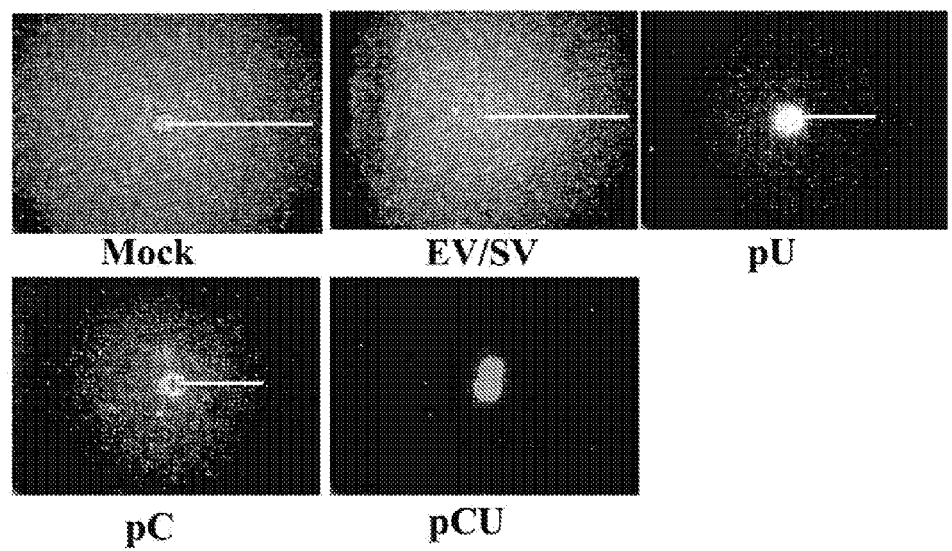
Figure 20B:
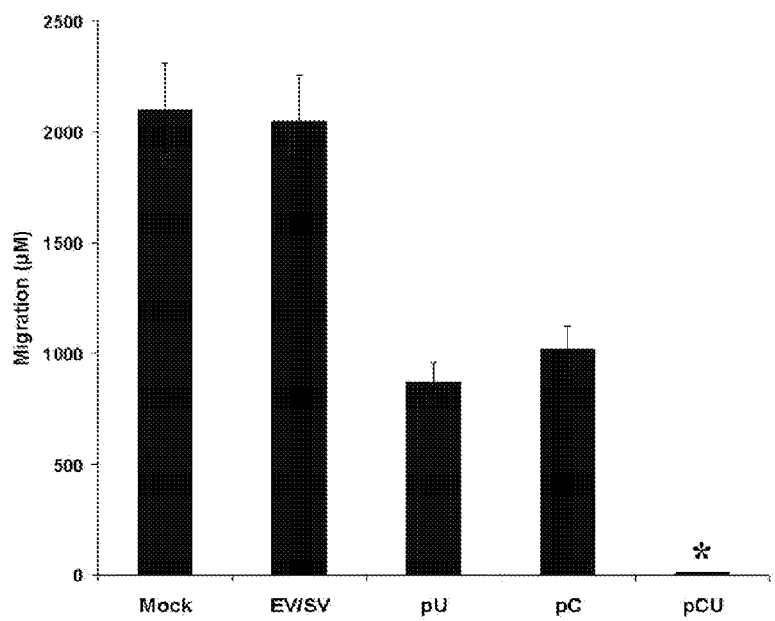

To determine whether cathepsin B and uPAR siRNA expression is capable of influencing tumor cell migration and proliferation, SNB19 spheroids were transfected with the pCU vector. As shown in FIG. 20A, there was much higher cell migration from spheroids transfected with mock and empty vector (EV) and up to 50% inhibition of migration was observed with single construct transfected spheroids. However, cell migration from tumor spheroids was completely inhibited in spheroids transfected with the pCU vector. The migration of the mock and empty vector transfected spheroids was significantly higher (P<0.001) compared to pC, pU and pCU transfected spheroids as quantitated by the number of cells migrating out from the spheroids (FIG. 20B). The migration of cells from the spheroids were inhibited with bicistronic construct compared to single RNAi constructs for these molecules. A few cells migrated from pCU-transfected SNB19 spheroids as compared to that of the mock and empty vector controls, thereby indicating the role of cathepsin B and uPAR in cell migration.

Example 18 siRNA Against Cathepsin B and uPAR Inhibits Tumor Cell Invasion

Figure 20C:
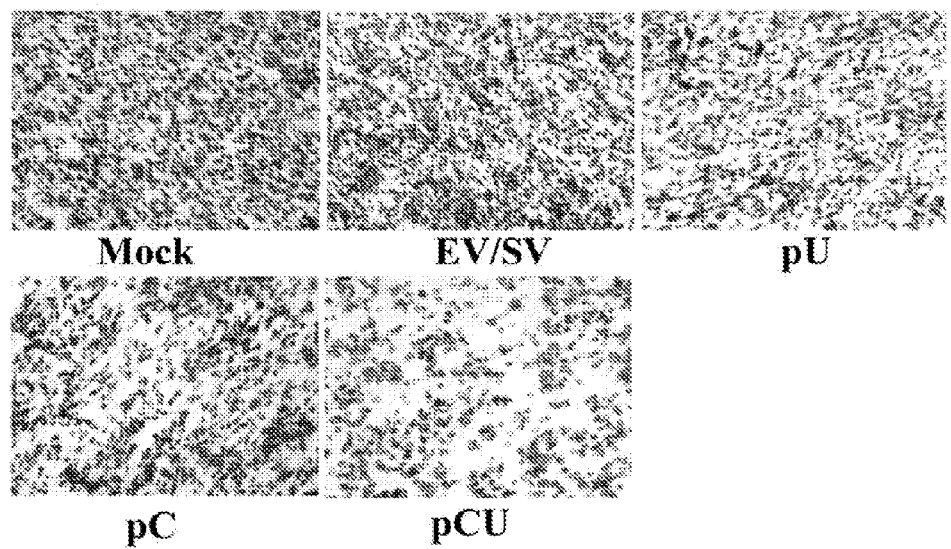
Figure 20D:
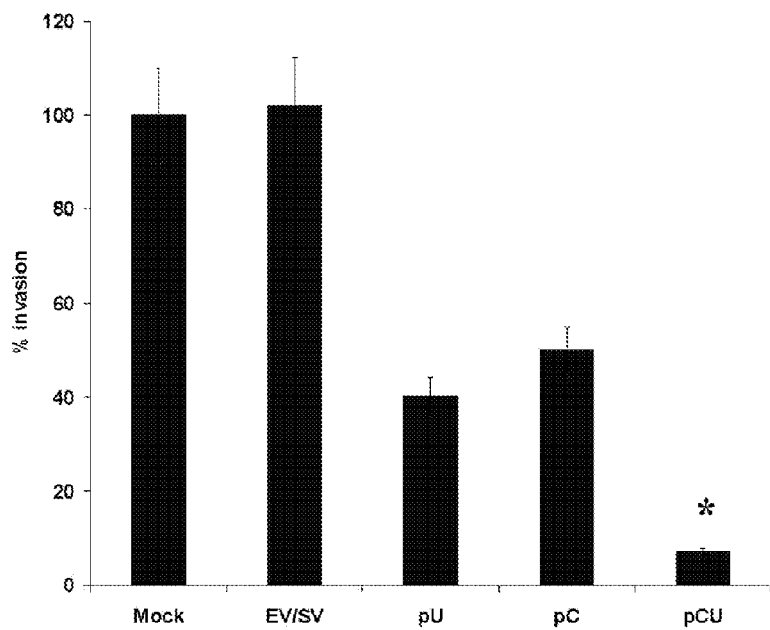

To evaluate the impact of siRNA-mediated inhibition of cathepsin B and uPAR on glioma invasiveness, a two-model system was used. SNB19 cells transfected with mock and empty vector extensively invaded the Matrigel-coated transwell inserts as observed by the intense staining of the cells. In contrast, the pC, pU and pCU-transfected cultures had less invasiveness through the reconstituted basement membrane, compared to mock and empty vector transfected cells (FIG. 20C). Quantitative determination of invasion confirmed that SNB19 cells transfected with the pC, pU and pCU vector invaded only 55%, 40% and 6% respectively as compared to mock and empty vector-transfected controls (FIG. 20D). Inhibition of the invasive behavior of these cells as determined by Matrigel invasion assay was much higher in the bicistronic construct transfected cells when compared to the single construct.

Figure 20E:
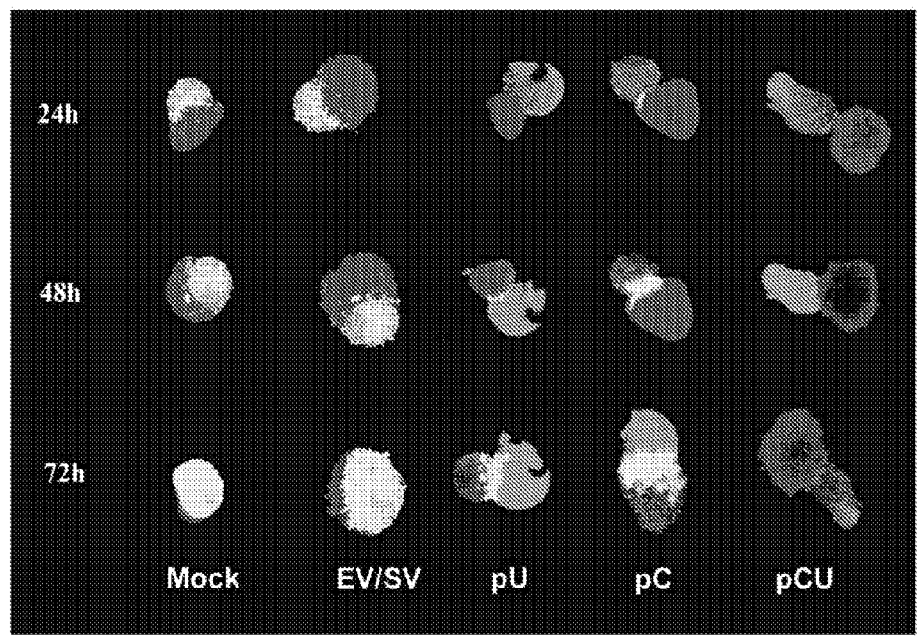
Figure 20F:
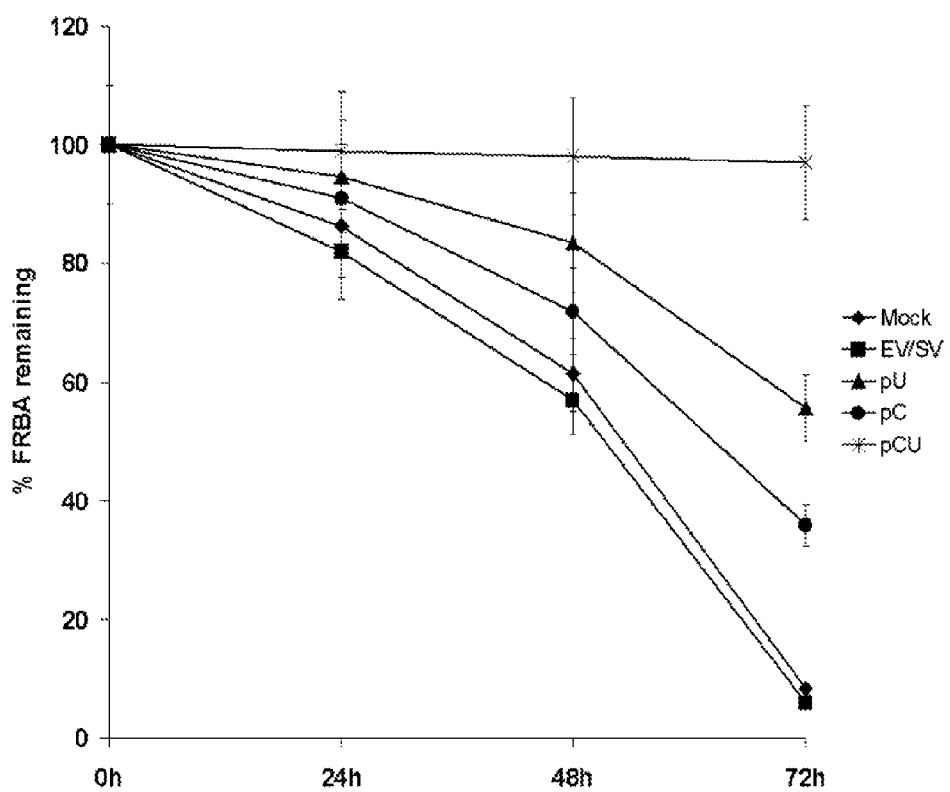

The extent of effect of pCU in spheroid invasion assay was tested. In the spheroid co-culture assay, control glioma spheroids and spheroids transfected with the empty vector progressively invaded fetal rat brain aggregates and resulted in partial to almost complete inhibition of invasion of spheroids transfected with pCU (FIG. 20E). Quantitation of the fetal rat brain aggregates revealed that glioma spheroids invaded the fetal rat brain aggregates by 25% within 24 h, >70% within 48 h and >90% at 72 h. In contrast, the tumor spheroids transfected with the pCU vector did not invade the fetal rat brain aggregates. At 72 h, the rat brain aggregates revealed invasion approximately 90%, 85%, 55% and 35% in the mock empty vector, pC, and pU transfected co-cultures, but only 2% to 3% invasion in the pCU transfected co-cultures (FIG. 20F). Taken together, these findings provide strong evidence that RNAi-mediated silencing of cathepsin B and uPAR strongly inhibits glioma cell invasion in both in vitro models, and that the effect was much higher with bicistronic construct compared to single constructs.

The acquisition of tumor cell invasiveness is one of the aspects of tumor progression. There are several reports to indicate that expression of cathepsin B and uPAR are essential components of the invasion process. Transfection with the pCU vector inhibited the invasiveness of SNB19 cells and spheroids in the Matrigel invasion and spheroid co-culture assays. The requirement of cathepsin B for Matrigel invasion could be due to its interaction with a network of proteases. Cathepsin B was shown to activate precursors of serine proteinases to their active forms, such as pro-uPA and metalloproteinases, such as prostromelysin. Invasiveness through Matrigel of transformed human breast epithelial cell lines was related to cathepsin B expression and was inhibited by cysteine proteinase inhibitors. In ovarian cancer cells, inhibition of cell surface cathepsin B prevents activation of pro-UPA, and subsequently, invasion of the carcinoma cells through Matrigel. Cathepsin B activity in human colon cancer is associated with the invasiveness of cancer cells, endothelial cells and inflammatory cells as well as apoptotic and necrotic cell death. uPA and uPAR are known to be overexpressed in various malignancies including breast, ovarian, and gastric cancers, and have been demonstrated to be essential in the maintenance of invasive and metastatic phenotype.

Example 19 siRNA Mediated Down Regulation of Cathepsin B and uPAR Reduces the Proliferation of SNB 19 Cells A standard MTT assay was used to assess the effect of the siRNA vectors (Control, EV, SV, pC, pU and pCU) on proliferation of cells cultured on vitronectin-coated microplates (FIG. 21). 72 h after infection, the pC, pU and pCU vector-infected SNB19 cells showed a decrease in proliferation relative to that of SNB19 and vector controls. PCU transfected cell did not show any appreciable growth even after 7 days of transfection. No floating cells or cell derby was seen in any of the transfected cells even after 7 days of assay indicating the absence of apoptosis.

Example 20 siRNA Mediated Down-regulation of uPAR and Cathepsin B Inhibits ERK1/2 and FAK Phosphorylation To determine the effect of down regulation of uPAR and cathepsin B on signaling pathway molecules, the phosphorylation of ERK and FAK were assayed by Western blotting both of which are directly involved in tumor cell survival, migration and proliferation. FIG. 22 shows that RNAi mediated simultaneous down regulation of uPAR and cathepsin B retards the phosphorylation of ERK1/2 and FAK and the effect was much less with single constructs.

Results demonstrate that the downregulation of uPAR and cathepsin B induces the down regulation of ERK1/2 and FAK phosphorylation which are directly responsible for cell survival and proliferation. The involvement of uPAR in the ERK-FAK cascade has previously been reported in human carcinoma cells HEp3, but the role of cathepsin B still remains unclear. A combinational downregulation of uPAR and cathepsin B is more effective in inhibiting phosphorylation of ERK1/2 and FAK.

Example 21

Cathepsin B and uPAR siRNA Suppresses Intracranial Tumor Growth

An intracranial tumor model was used to assess potential effects of RNAi-mediated inhibition on pre-established tumor growth in vivo. The brain sections of the untreated (mock) and EV-treated control groups were characterized by large spread tumor growth by H & E staining and high GFP fluorescence after a 5-week follow-up period (FIGS. 23A & B). However, GFP fluorescence was not detected in the brain sections of mice treated with the pCU vector (FIGS. 23A & B). Further quantification of H & E stained brain sections scored by a neuropathologist who was blind to the treatment, revealed no difference in tumor size between the mock and empty vector treatment groups and significant regression of tumor growth 55% and 65% in the pC and pU treated groups compared to controls. However, total regression of pre-established tumors was revealed in the pCU treated group (FIG. 23). These results demonstrate that RNAi-mediated suppression of cathepsin B and uPAR significantly inhibited intracranial tumor growth.

Local intracranial delivery of pCU using mini osmotic pumps effectively inhibited human malignant glioma growth. Mini osmotic pumps maintain a well-defined and consistent pattern of drug exposure for a significant period of time and can be used successfully to deliver agents to the brain. Downregulation of cathepsin B and uPAR results in inhibition of tumor-induced angiogenesis. A co-culture assay was used in vitro to test the effect of pCU on angiogenesis. The results demonstrate that cathepsin B and uPAR play relevant roles in stimulating angiogenesis, suggesting a possible mechanism of action for the in vivo antitumor activity of pCU in the intracranial tumor model. Intense staining for cathepsin B is present in endothelial cells of neo-vessels but not in pre-existing microvasculature in prostate. Likewise, strong immunostaining of cathepsin B was observed in rat brain microvascular endothelial cells as they formed capillary tubes in vitro. Since cathepsin B was shown to be an inhibitor of TIMPs and TIMPs are inhibitors of angiogenesis, cathepsin B could also stimulate angiogenesis, which has a relevant role in tumor spread. RNAi-mediated targeting of cathepsin B and uPAR suppressed pre-established intracranial tumor growth, possibly by inhibiting angiogenesis and invasiveness. These results also support that the siRNA-mediated downregulation of target gene expression is sufficiently stable within the brain microenvironment.

Example 22

Effect of siRNA Constructs on uPAR Protein, and uPA and MMP-9 Enzymatic Activity in SNB19 Glioblastoma Cells To simultaneously inhibit three endogenous genes with hairpin siRNA, a vector ($pU_2M$) was constructed expressing siRNA for uPAR (77-98 bases of human uPAR in RNA), uPA (346-367 bases of human uPA in RNA) and MMP-9 (360-381 bases of human MMP-9 in RNA) under the control of the CMV promoter (FIG. 24). The bases indicate the positions in a full length coding sequence. Western blot analysis was performed to examine the effect of empty vector/scrambled vector (EV/SV), puPAR, puPA, MMP-9 and $pU_2M$ transfection on uPAR protein concentrations in SNB19 cells. The uPAR protein band was present in SNB19 cells transfected with EV/SV, puPA and pMMP-9, whereas it was reduced significantly in puPAR- and $pU_2M$-treated cells (FIG. 25A). The effect of the tricistronic construct ($pU_2M$) was greater than the puPAR (FIG. 25A). The levels of GAPDH determined that equal quantities of protein were loaded in the gel (FIG. 25A). Fibrin zymography was performed to examine the effect of EV/SV, puPAR, puPA, pMMP-9 and $pU_2M$-treated SNB 19 cells on uPA enzymatic activity. Gelatin zymography was performed to determine the effect of these constructs on the levels of MMP-9 in SNB19 cells. MMP-9 levels were significantly reduced in SNB19 cells treated with puPAR, pMMP-9 and $pU_2M$ compared to parental, EV/SV- and puPA-treated cells (FIG. 25B). Interestingly, MMP-2 levels were also downregulated in $pU_2M$-treated cells. Care was taken to load equal quantity of proteins. (FIG. 25B). The uPA enzymatic activity (MR 55 000) was reduced significantly in puPA- and $pU_2M$-treated cells compared with the parental, EV/SV-, puPAR- and pMMP-9-treated groups (FIG. 25C).

The effect of the tricistronic construct was more pronounced than that of the single siRNA constructs for these molecules. Determined by immunohistochemical analysis, puPAR, puPA, pMMP-9 and $pU_2M$ transfection decreased uPAR, uPA and MMP-9 concentrations in SNB19 cells. FIG. 25D shows the protein levels of uPAR, uPA and MMP-9 in parental, EV/SV-, puPAR-, puPA-, pMMP-9- and $pU_2M$-transfected cells using specific antibodies for uPAR, uPA and MMP-9. The respective intensities of uPAR, uPA and MMP-9 were high in parental cells and in cells transfected with EV/SV. By contrast, uPAR intensity decreased in SNB19 cells transfected with puPAR and $pU_2M$. puPA and $pU_2M$ transfection significantly decreased the intensity of uPA protein compared with parental, EV/SV-, puPAR- and pMMP-9-transfected cells. Further, MMP-9 protein concentration decreased significantly in pMMP-9- and $pU_2M$-transfected cells compared with parental, EV/SV, puPA- and puPAR-transfected cells. These results demonstrate that the effect of the single constructs is molecule-specific and that the effect of the tricistronic construct is much more pronounced than that of the single constructs alone.

Figure 26A:
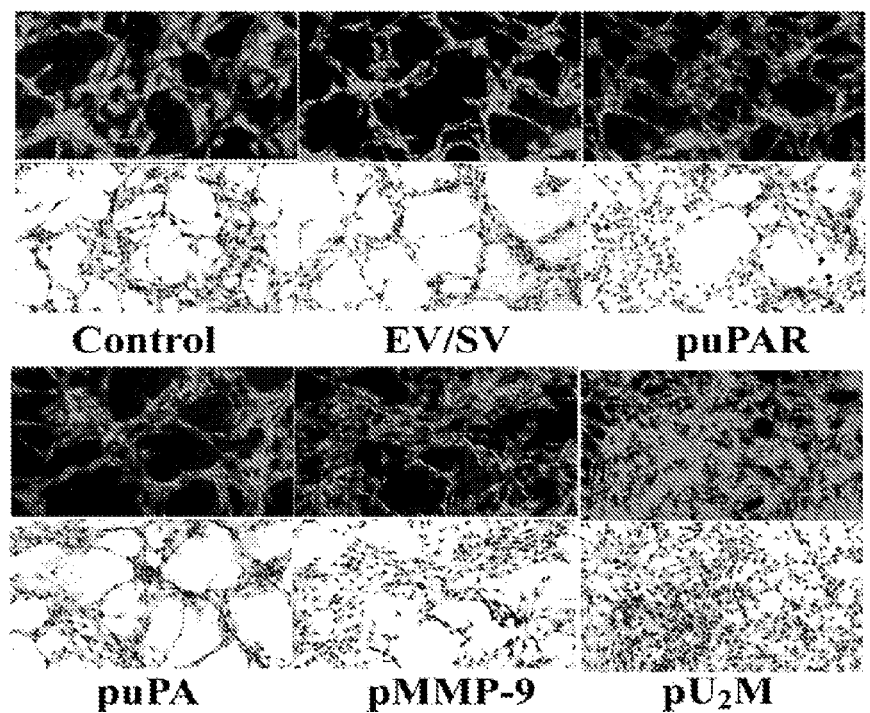

Example 23 puPAR, puPA, pMMP-9 and $pU_2M$ Inhibit Tumor-Induced Capillary Network Formation The growth of a glial tumor depends on the induction of new capillary blood vessels that are necessary to support the developing tumor mass. A co-culture system was used in which microvascular endothelial cells were induced by conditioned media from glial cells to form capillary-like structures to examine the effect of RNAi-mediated suppression of uPAR, uPA and MMP-9. Immunohistochemical analysis using factor VIII antigen to evaluate tumor-induced vessel formation in an in vitro co-culture system and performed H&E staining. Endothelial cells form capillary-like structures in the presence of conditioned media from SNB19 parental and EV/SV-transfected cells (FIG. 26A). By contrast, transfection of SNB19 cells with vectors expressing siRNA for uPA, uPAR and MMP-9 either individually or in combination partially or completely inhibited tumor-induced microvessel formation (FIG. 26A). New branch points and/or an increase in the number of branches were not detected in $pU_2M$-transfected cells compared with EV/SV-treated cells (FIG. 26A). Furthermore, compared with EV/SV-treated cells, the formation of capillary-like structures was inhibited by ~55% in puPAR-treated cultures, ~36% in puPA-treated cultures and ~60% in pMMP-9-treated cultures (FIG. 26B).

Figure 26B:
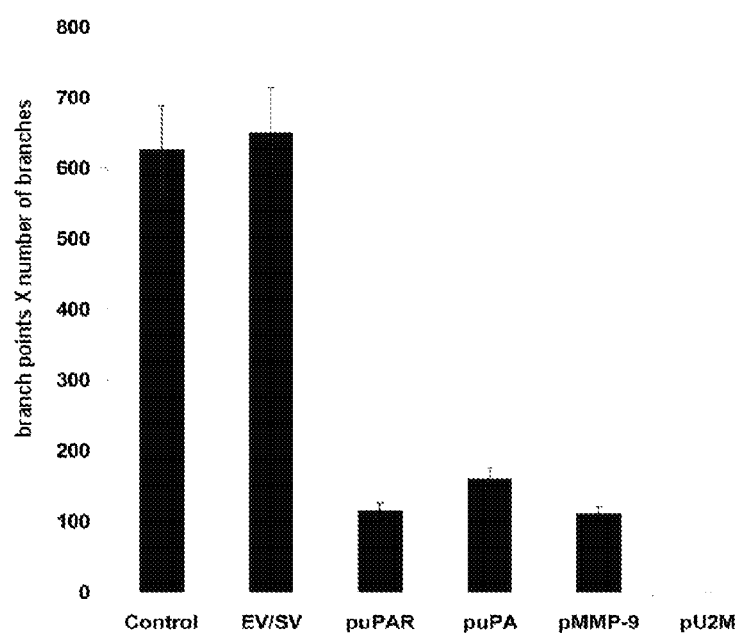

Conditioned medium from a glioblastoma cell line transfected with $pU_2M$ inhibited the capillary-like structures compared with mock or empty vector (FIG. 26A-B). This indicates that the angiogenic signal necessary for the induction of angiogenesis was not present in $pU_2M$-transfected cells. As demonstrated by the absence of angiogenic induction in $pU_2M$-transfected SNB19 glioma cells, downregulation of uPA, uPAR and MMP-9 by hpRNA caused the downregulation of angiogenic factors. The absence of uPA or tissue type plasminogen activator (tPA) significantly decreased the development of experimental choroidal neovascularization compared with wild-type (WT) or uPAR-deficient mice (uPA−/−). It has been reported that a significantly diminished primary tumor growth in uPA−/− and plasminogen activator inhibitor-1-deficient (PAI-1−/−) mice occurred, relative to WT mice and tumors in uPA−/− and PAI−/− mice displayed lower proliferative and higher apoptotic indices and also displayed a different neovascularmorphology, as compared with WT mice. Several peptides that have been shown to inhibit uPA binding by bacteriophage display inhibit angiogenesis and primary tumor growth in syngeneic mice.

Example 24 puPAR, puPA, pMMP-9 and $pU_2M$ Inhibit Invasion in SNB19 Cells

Figure 26C:
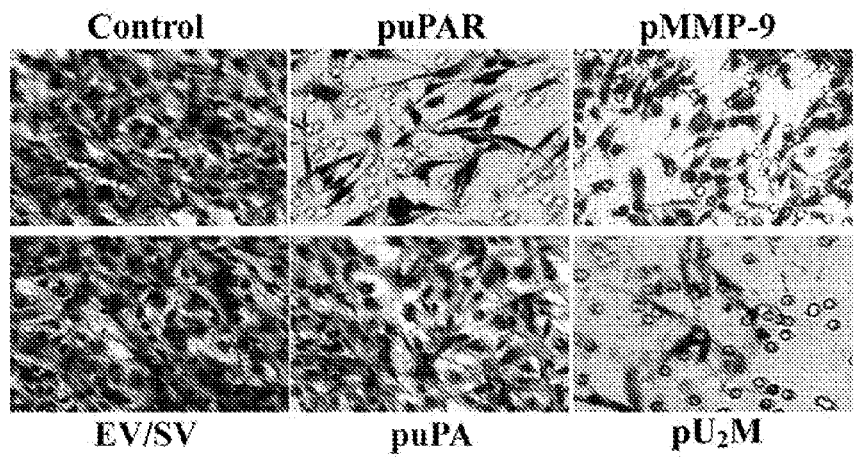
Figure 26D:
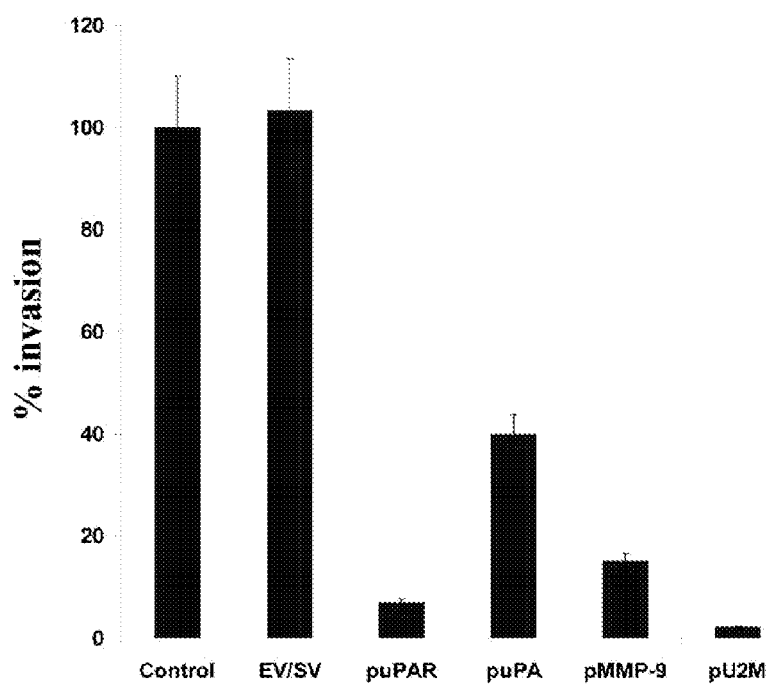

Proteolytic degradation of ECM components is relevant for tumor-cell invasion. To evaluate the impact of siRNA-mediated inhibition of uPAR, uPA and MMP-9 on glioma invasiveness, two models were utilized. In the first model, the invasive ability of SNB 19 cells transfected with puPAR, puPA, pMMP-9 and $pU_2M$ was compared to those infected with the EV/SV vector. SNB19 cells transfected with EV/SV and parental cells demonstrated extensive invasion through Matrigel-coated transwell inserts, as indicated by the intense staining of cells. By contrast, puPAR-, puPA-, pMMP-9- and $pU_2M$-transfected cultures were less invasive through the reconstituted basement membrane, as indicated by the staining intensity compared with the controls (FIG. 26C). Quantification confirmed that transfection with puPAR, puPA, pMMP-9 and $pU_2M$ vectors reduced invasion by SNB19 cells to 9%, 40%, 15% and 2%, respectively, compared with parental and EV/SV transfected controls (FIG. 26D). Inhibition of invasion was higher in cells transfected with the tricistronic construct when compared to single constructs alone.

Figure 27A:
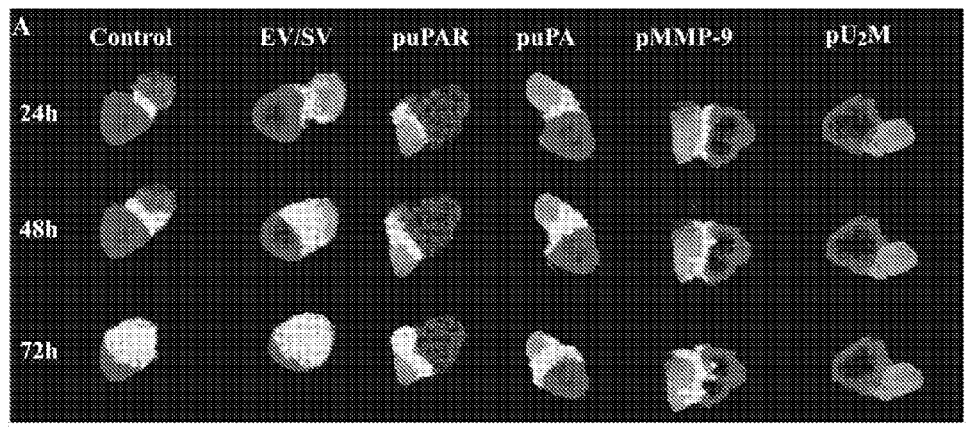
Figure 27B:
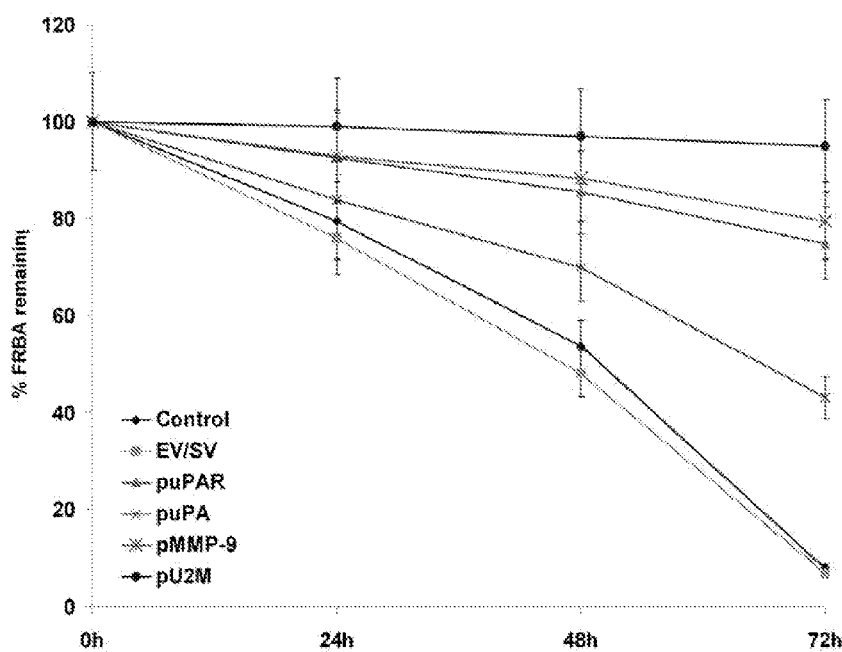

The effect of puPAR, puPA, pMMP-9 and $pU_2M$ vectors was examined using a spheroid invasion assay. A significant, potential advantage of using glioma spheroids is that tumor cells grown in three-dimensional cultures exhibit properties that more closely resemble those of tumors in vivo. In the spheroid co-culture system, control spheroids and spheroids transfected with the EV/SV vector progressively invaded fetal rat-brain aggregates whereas spheroids transfected with puPAR, puPA, pMMP-9 and pU$_2$M demonstrated partial to almost complete inhibition of invasion (FIG. 27A). Quantification revealed that glioma spheroids invaded the fetal rat brain aggregates by 30% within 1 day, 55% within 2 days and 95% by 3 days, at which time the tumor spheroid and brain aggregates had combined into single entity (FIG. 27B). A similar trend was observed with glioma spheroids transfected with the EV/SV vector. By contrast, tumor spheroids transfected with the pU$_2$M vector did not invade fetal rat brain aggregates. By 3 days, the rat brain aggregates were invaded by approximately 96%, 95%, 45%, 25% and 15% in the parental, EV/SV-, puPA-, pMMP-9- and puPAR-transfected co-cultures, and by 1% in the pU M-transfected co-cultures (FIG. 27B). These results provide strong evidence that pU$_2$M strongly inhibits glioma invasion in both in vitro models.

Example 25 pU$_2$M Completely Regresses Intracranial Tumor Growth

Figure 27C:
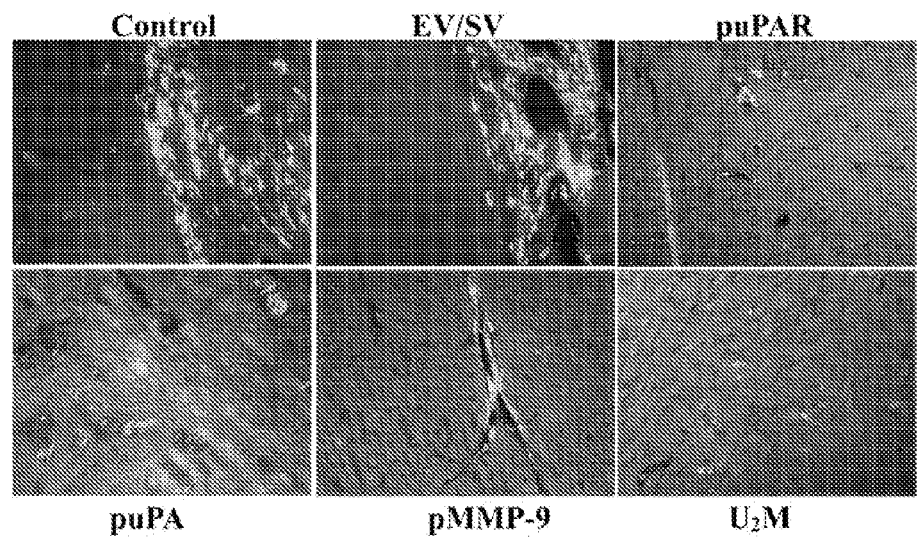
Figure 27D:
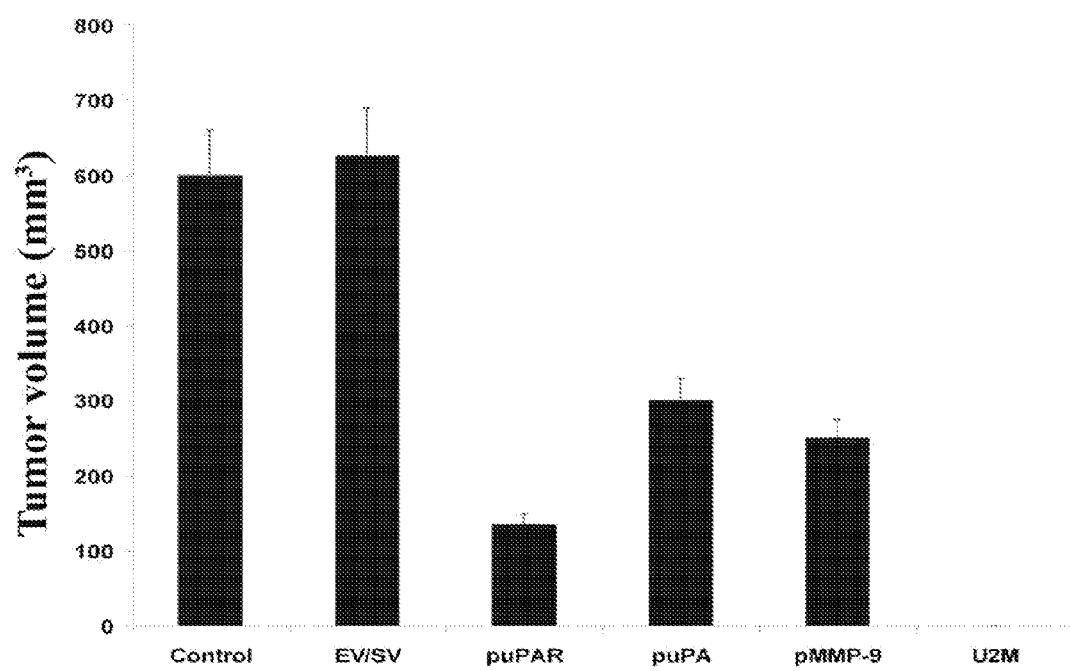

The downregulation of uPAR, uPA and MMP-9 levels was examined using either single or tricistronic constructs causes regression of pre-established intracranial tumor growth in nude mice. All animals in the control and EV/SV-treated groups had intact cerebral tumors that were characterized by strong GFP fluorescence (FIG. 27C) whereas brain sections of mice treated with puPAR, puPA and pMMP-9 had small tumors, illustrated by minimal GFP fluorescence. Notably, GFP fluorescence was not detected in brain sections of mice treated with pU$_2$M (FIG. 27C). Further quantification of these sections (scored by a neuropathologist blinded to treatment conditions) revealed no difference in tumor size between the parental and EV/SV treated groups and significant regression of pre-established intracranial tumor growth in the groups treated with puPAR, puPA and pMMP-9 (80%, 55%, and 68% respectively) compared to control groups (FIG. 27D). However, complete regression of pre-established intracranial tumor growth was revealed in the pU$_2$M treated group. These results demonstrate that RNAi-mediated suppression of uPAR, uPA and MMP-9 using a tricistronic construct completely eradicated malignant glioma growth in nude mice.

Example 26

Inhibition of ERK1/2 Phosphorylation

To better understand the effect of siRNA-mediated downregulation of uPAR, uPA and MMP-9 on signaling pathways, total and phosphorylated levels of ERK1/2 were assayed, which are involved directly in tumor-cell survival, migration and proliferation. Western blots showed that there was no significant difference in total ERK1/2 concentrations in control and EV/SV-transfected cells compared with puPAR-, puPA-, pMMP-9- and pU$_2$M-transfected cells (FIG. 28). However, the concentration of phospho-ERK1/2 was reduced significantly in SNB19 cells transfected with the pU$_2$M vector compared with the control, EV/SV-, puPAR-, puPA- and pMMP-9-transfected SNB19 cells. Notably, there was no effect on the levels phospho-ERK in SNB19 cells transfected with any of the single constructs. GAPDH levels indicated that equal quantities of protein were loaded in the gel (FIG. 28).

Example 27

Gene-Specific siRNAs Lower Expression of MMP-9 and Cathepsin B Protein in a Glioma Cell Line To test the effectiveness of simultaneously inhibiting two endogenous genes with a hairpin siRNA expression vector, a vector expressing siRNA for cathepsin B (732 to 753 bases of human cathepsin B mRNA) and MMP-9 (360 to 381 bases of human MMP-9 mRNA) were constructed under the control of the human cytomegalovirus (CMV) promoter (pCM) (FIG. 29). The bases indicate the positions in a full length coding sequence. FIG. 30A demonstrates that transfection with pC and pCM vector specifically inhibited cathepsin B levels compared to mock, empty, and pM vector controls. β-actin levels assessed in the same blot indicated that the inhibition of cathepsin B was specific and confirmed equal sample loading. MMP-2 and MMP-9 levels were determined in the conditioned medium in the transfected cells. The amount of MMP-9 released from the mock and empty vector (EV) transfected cells were the same. Cells transfected with pM and pCM vector expressed low levels of MMP-9 compared to the mock, EV, and pC controls. There was no change in the expression of MMP-2 demonstrating the sequence specific inhibition of the pM and pCM vector (FIG. 30B). To confirm that the decrease in MMP-9 activity was due to a decrease in protein expression, the conditioned medium was analyzed using immunoblotting with an MMP-9-specific antibody. MMP-9 protein band was decreased dramatically by immunoblotting of the conditioned medium from cells transfected with pM and pCM vector, but bands were significantly much higher in the conditioned medium from the cells infected with the empty vector or with pC vector (FIG. 30C).

Example 28

Inhibition of Tumor Cell-Induced Capillary Network Formation by PCM Vector

Figure 31A:
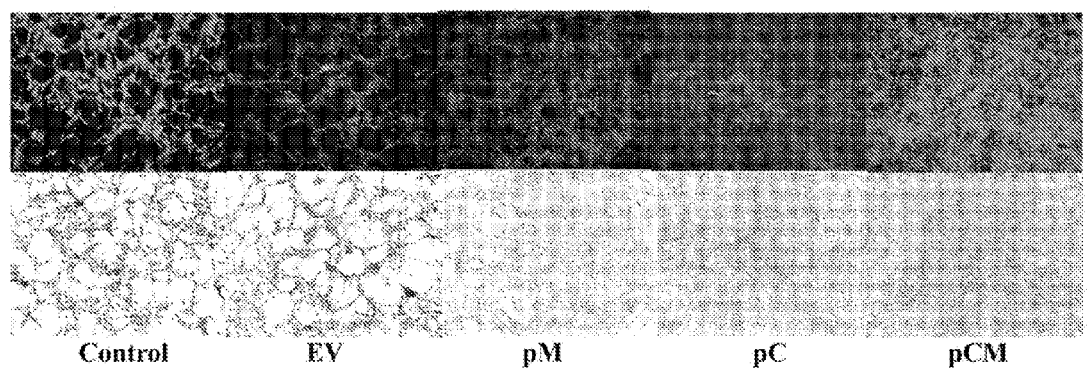
Figure 31B:
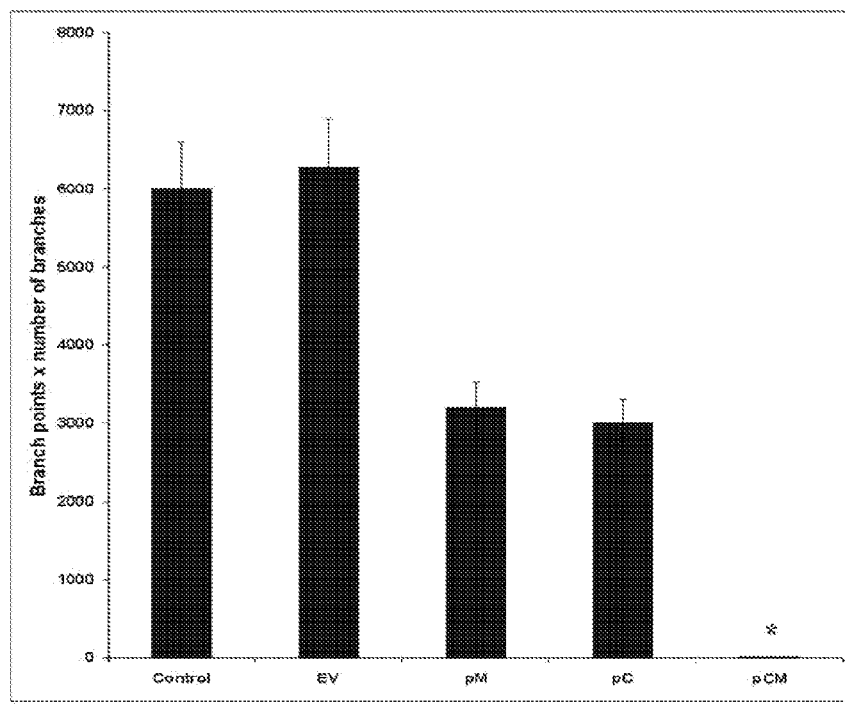
Figure 31C:
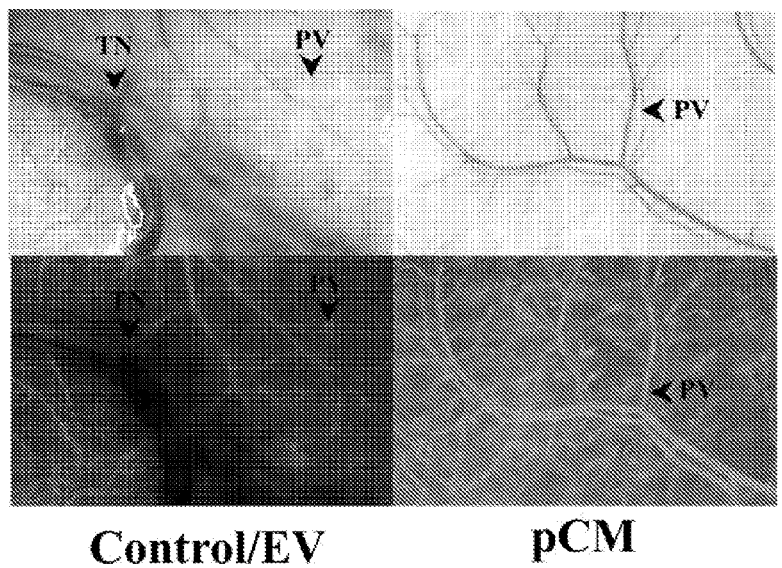

The growth of a glial tumor depends on the induction of new capillary blood vessels as they are necessary to support the developing tumor mass. A co-culture system was used in which microvascular endothelial cells were induced by glial cells to form capillary-like structures in order to examine the RNAi-mediated suppression of cathepsin B and MMP-9. SNB19 cells induced endothelial cells to differentiate into capillary-like structures within 72 h. In contrast, transfection of SNB19 cells with the vector expressing siRNA for cathepsin B and MMP-9 completely inhibited tumor cell-induced microvessel morphogenesis (FIG. 31A). Further quantification of the branch points and number of branches were undetectable in pCM transfected co-cultures compared to mock and empty vector (FIG. 31B). Further, the effect was only 50% in pC or pM treated co-cultures when compared to pCM vector in relation to capillary-like structures. To confirm the in vitro co-culture experiments, whether the pCM vector could inhibit tumor angiogenesis were examined in vivo as assessed by the dorsal window model. Implantation of a chamber containing mock and empty vector (EV) transfected SNB19 cells resulted in the development of microvessels (as indicated by arrows) with curved thin structures and many tiny bleeding spots. In contrast, implantation of SNB19 cells transfected with the pCM vector did not result in the development of any additional microvessels (FIG. 31C).

Growth maintenance of malignant tumors is closely related with development of the vascular network that supplies the tumor with nutrients. The formation of a vascular network characterized by closed polygons and complex mesh-like structures in cells treated with the pCM vector was not observed. This network is typically observed when glioma cells are co-cultured with endothelial cells. Proteolysis of extracellular matrix components allows endothelial cells to migrate and releases stored angiogenic signaling molecules from the extracellular matrix. Immunohistochemical analysis demonstrated that cathepsin B was strongly expressed in malignant anaplastic astrocytomas and glioblastomas as compared to normal brain tissue.

These results show that MMPs can promote angiogenesis and that absolute lack of MMP activity can prevent new blood vessel formation. The tumor regression achieved by the combined treatment in the present disclosure is due to the complementary actions of cathepsin B and MMP-9. Targeting expression of cathepsin B and MMP-9 in tumor cells is an effective approach to control angiogenesis and tumor growth.

Example 29

Suppressive Effects of pCM Vector on Glioma Migration and Invasion

Figure 32A:
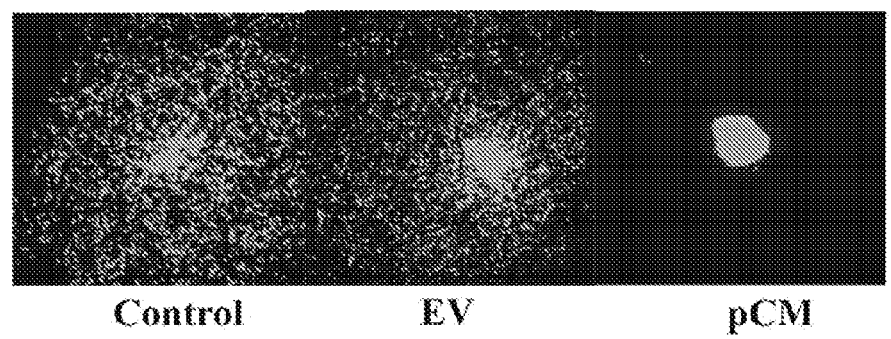
Figure 32B:
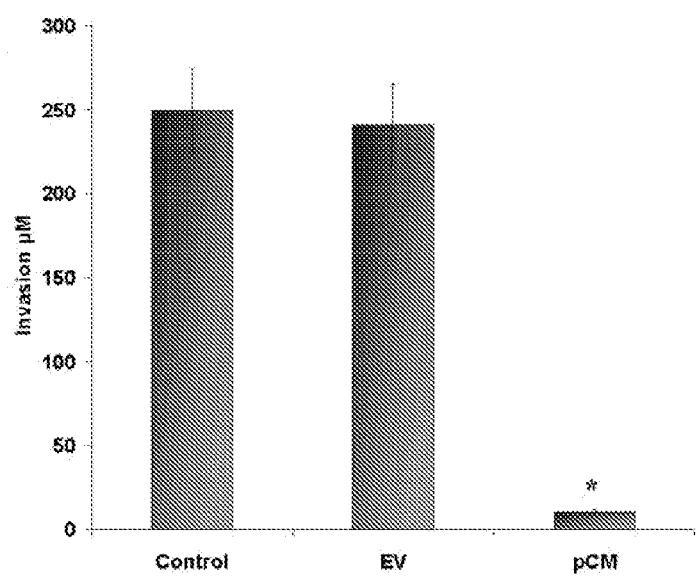

Cell migration requires the coordinated regulation of cell-cell attachments, cell-matrix attachment and matrix remodeling. The influence of suppressing cathepsin B and MMP-9 on the capacity of the cells to migrate on vitronectin in a spheroid migration assay was studied. Multicellular glioma spheroids were grown from SNB19-GFP cells in 6-well plates coated with agarose. After checking for viability using morphology and trypan blue exclusion, spheroids of similar diameter (100-200 μm) were transfected with mock, empty vector (EV) or the pCM vector expressing siRNA for cathepsin B and MMP-9. Three days later, single spheroids were placed on vitronectin-coated plates and allowed to migrate. FIG. 32A indicates that cells from the control spheroids and spheroids infected with the empty vector showed a significantly higher capability of cells to migrate as compared to the pCM vector-infected cells. Proteolytic degradation of extracellular matrix components is relevant for tumor cell invasion. To investigate whether expression of siRNA for cathepsin B and MMP-9 plays a role in glioma invasiveness, the invasive ability of SNB19 cells transfected with the pCM vector to those cells infected with mock and empty vector were compared. SNB19 cells transfected with mock and empty vector (EV) invaded through Matrigel more extensively compared to the pCM vector transfected cells penetrated through the matrigel (FIG. 32B).

Figure 32C:
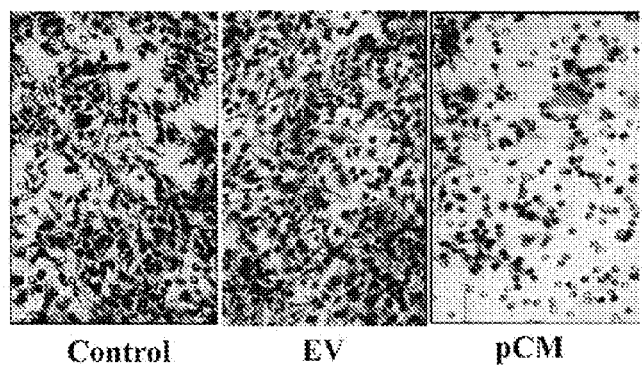
Figure 32D:
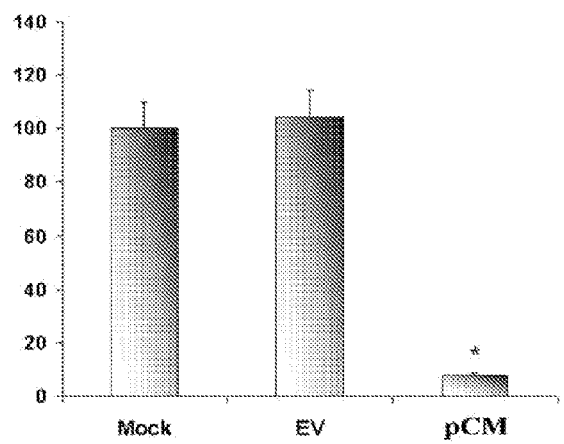
Figure 32E:
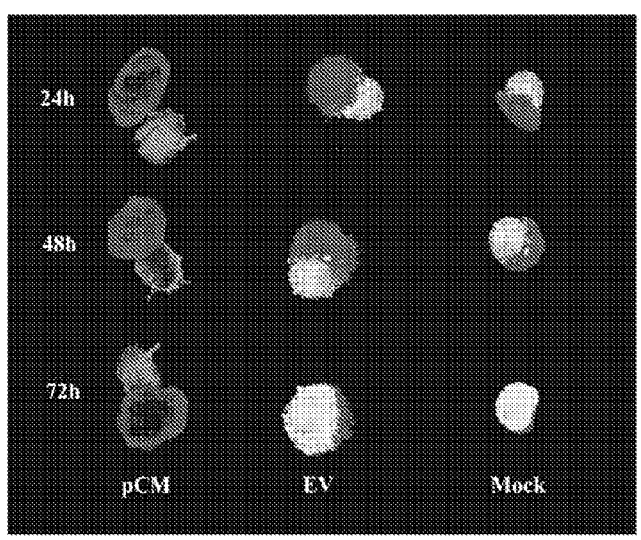
Figure 32F:
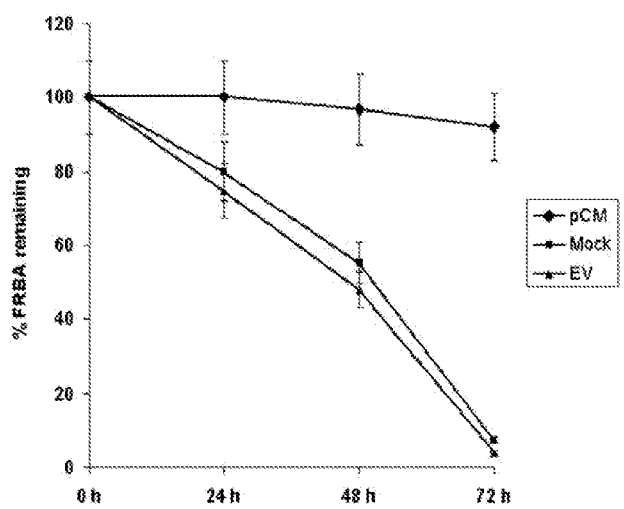

The extent of suppressive effects of the siRNA in a spheroid invasion assay were examined. A potential advantage of using glioma spheroids is that tumor cells grown in three-dimensional cultures have been shown to exhibit properties that more closely resemble those of tumors in vivo. Mock- and empty vector-transfected spheroids invaded 25% of the normal brain aggregates within one day, 50% within two days and by three days, 95% of the tumor spheroid and brain aggregate had combined into a single entity (FIG. 32C). In contrast, glioma spheroids transfected with the pCM vector expressing siRNA for cathepsin B and MMP-9 remained separate from the normal brain aggregates.

Present disclosure shows that the CMV promoter-driven expression of siRNA against cathepsin B and MMP-9 (pCM) can successfully silence cathepsin B and MMP-9 expression in the SNB19 glioblastoma cell line, as analyzed by Western blotting and gelatin zymography. Results also demonstrated that the invasive potential of glioma cells treated with the pCM vector was significantly inhibited. Cancer cells must detach from the neighboring cells and extracellular matrix components to migrate and invade. Matrix proteolysis can directly modulate cell-matrix adhesion either by removal of adhesion sites or by exposing a binding site, which in turn may effect cell migration. RNAi-mediated inhibition of cathepsin B and MMP-9 significantly blocked the migration of SNB19 glioma cells as shown in a spheroid migration assay.

Example 30

RNAi Induces Complete Regression of Glioblastoma Tumors in Nude Mice

The capacity of the siRNA for MMP-9 and cathepsin B to inhibit regression of intracranial SNB19 tumors was tested in nude mice. Mice with pre-established glioma growth were stereotactically injected with PBS (mock), empty vector (EV), pC, pM and pCM vector. Brain sections of mice treated with mock and EV showed rapid tumor growth whereas mice injected with the pCM vector using mini osmotic pumps into a pre-established tumor, resulted in complete inhibition of tumor growth over a 5-week time period (FIGS. 32A & 32B). Quantification of tumor size showed a total regression of tumor in the pCM vector treated group compared to the mock or empty vector (FIG. 33C). Brain sections of mice treated with pC or pM vector treated group, resulted in around 50% tumor regression compared to control groups. Intraperitoneal injections of the vector also resulted in complete regression of pre-established intracranial tumor growth with no indication of tumor cells for long period of several months (FIG. 33D). Thus, RNAi was able to completely eradicate malignant glioma tumor growth in this nude mouse model. The sustained suppression of glioma growth could be due to siRNA amplification. siRNA against cathepsin B and MMP-9 suppressed glioma growth more efficiently than antisense oligodeoxynucleotide for MMP-9 and cathepsin B. Thus, the control of both cathepsin B and MMP-9 expression has considerable significance for regulation of tumor progression.

The anticancer efficacy of RNAi-mediated inhibition of cathepsin B and MMP-9 was demonstrated. Comparison of the suppressive effects of antisense oligonucleotides and siRNAs directed against the same targets in mammalian cells revealed that the IC50 value for the siRNA was about 100-fold lower than that of the antisense oligonucleotides. The ability of siRNA to silence sequence-specific target genes and the lower concentrations required to inhibit gene expression make RNAi a powerful tool for gene therapy.

Example 31

Reduced Immunogenic Response for siRNAs from Circular Plasmids

To develop a vector capable of producing hairpin siRNA molecules for uPA and uPAR, the mammalian expression plasmid vector pCDNA 3 was used. FIGS. 34-35 illustrate schematic representations of the various forms of U6 and CMV driven RNAi constructs. Self-complementary inverted repeat sequences spaced by a 9 base G C deficient region targeted to uPA (346 to 367) and uPAR (77 to 89) were synthesized. Oligos for uPA were terminated with HindIII sites and the oligos for uPAR were terminated with BamHI and self annealed by heating to 100° C. for 5 min and cooled to room temperature in 6×SSC which resulted in the formation of double-stranded DNA molecules with the respective sticky restriction site ends. These dsDNA molecules were ligated to the BamHI and HindIII sites of the pCDNA3 plasmid vector, resulting in the formation of a plasmid containing inverted repeats for uPA and uPAR downstream of the CMV promoter and terminated by a BGH terminator. The resultant plasmid, termed pU2, when transfected to mammalian cells resulted in the production of a dual hairpin siRNA molecule targeting both to uPA and uPAR which were further processed by a dsRNA recognizing enzyme (DICER) to produce individual siRNA molecules to induce RNAi. A sequence homologous to GFP was used in the construction of a scrambled vector. Imperfect sequences, which do not form a perfect hairpin structure, were used to develop the scrambled vector. Two self-complementary oligos were synthesized and annealed to generate a dsDNA molecule with HindIII sites. This dsDNA molecule was ligated in the HindIII site of pCDNA3 plasmid. The resulting plasmid was called pSV. The resulting CMV-driven transcript had no hairpin like structure and was not homologous to any native gene.

An expression cassette expressing siRNA for uPA and uPAR was subcloned into the Ad5 shuttle vector in the ΔE1 region driven with either a RNA pol II or RNA pol III promoter. The resultant plasmid was co-transfected with Ad 5 genomic plasmid (like PJM17) into 293 replication permissive cells to generate recombinant replication deficient Ad 5 virus particles containing siRNA expression cassette for uPA and uPAR (FIG. 36). A GFP RNAi vector was constructed to determine the specificity of targeting using RNAi. Stable SNB19 cells expressing GFP were used as controls and transfected with RNAi targeted against GFP. Cells transfected with GFP RNAi lost the GFP expression (FIG. 37) whereas no change in the expression of GAPDH mRNA as seen in the RT-PCR reaction (FIG. 44).

To determine whether circular plasmids with either the U6 (RNA pol III) or CMV (RNA pol II) promoter induce cellular level immune response, 5 constructs were used with either the U6 or CMV promoter. SNB19 human glioma cells were transfected with circular plasmids containing either the U6 or CMV promoter to drive the following: no insert called empty vector (EV), GFP RNAi insert which did not form perfect hairpin structure called scrambled vector (SV), RNAi hairpin expressor for uPAR (puPAR), uPA (puPA), and a dual RNAi hairpin expression for both uPAR and uPA (pU2). RT-PCR was performed to determine OAS1 expression levels. Total RNA was isolated from each of the transfected cells after 48 h of transfection and RT-PCR was performed to determine the level of OAS1 expression per 50 ng of total RNA. (RT-PCR was performed as per manufacturer's instructions (Invitrogen)). There was no change in the levels of OAS1 mRNA or GAPDH mRNA levels in SNB19 cells transfected with circular plasmids containing either the U6 or CMV promoter (FIG. 38).

Example 32

Comparison of RNA pol II (CMV) and RNA pol III (U6) as Promoters for the Initiation of RNAi To determine the activity and the effectiveness of RNA pol II and RNA pol III RNAi vectors were constructed in pSilencer plasmid (Ambion, Austin Tex.) for scrambled vector, uPAR, uPA and uPAR-uPA combination as in pcDNA3. The pSilencer constructs were terminated with tetra Ts as per manufacturer's instructions. SNB19 cells were transfected in two sets, one set contained RNA pol II promoter CMV and the second set contained RNA pol III promoter U6 (C, SV, puPAR, puPA and pU2). 48 h after transfection, proteins were extracted from cells as per standard protocol and loaded onto a (10 µg/lane) on 12% Poly acrylamide SDS gel. Western blotting and fibrin zymography was performed as per standard protocol and probed for uPAR and uPA and the loading control was determined by probing for GAPDH. From FIG. 39 it was clear that the RNA pol II promoter constructs were more efficient at down regulating the target molecules when compared to the RNA pol III promoter constructs.

Example 33

Determination of Interferon Response Gene OAS1

Plasmid constructs for empty vector (EV), scrambled vector (SV), uPAR (puPAR), uPA (puPA), and the bicistronic construct for uPAR and uPA (pU2) were used to determine the level of interferon induction in the SNB19 human glioma cell line. OAS1 gene expression was used as an indicator for interferon induction. Circular plasmids (C), linear expression cassette (L), and BGH poly A signal sequence deleted linear expression cassette (ΔA) were used. SNB19 cells were transfected with equivalent amounts of the above plasmid or expression cassettes (C, L, ΔA schematic representation) and total RNA was isolated after 48 h of transfection using standard protocols. RT-PCR was performed on the above samples and the levels of OAS1 amplicon were determined on an agarose gel. The primers used for OAS1 amplification were 5'-aggtggtaaagggtggctcc-3' (SEQ ID NO: 13) and 5'-acaaccaggtcagcgtcagat-3' (SEQ ID NO: 14). Primers used to amplify the expression cassette from the above plasmids (EV, SV, puPAR, puPA and pU2) were: forward primer 5'ctggtgtcgacctgcttccgcgatgtacgggc3' (SEQ ID NO: 15) and reverse primer 5'ctggtgtcgacacatccccagcatgcctgctat3' (SEQ ID NO: 16) (FIG. 40).

RT-PCR for OAS1 (2'5'-oligoadenylate synthetase) mRNA induction was performed to determine the relevance of a poly A signal sequence. Circular, linear (expression cassette alone) and expression cassette with deleted poly A signal sequence were used (C, L and AA respectively). In the case of EV and SV, no induction of OAS1 mRNA was detected (FIG. 41). In the case of EV, the overall length of the transcript was not expected to be more than 1 kb and the predicted structure of the transcript had no significant dsRNA structure to induce an immune response with or without a poly A tail as seen in the figure (also in SV) (FIG. 44). In contrast, with puPAR, puPA and pU2 the predicted secondary structure did possess dsRNA structures but with the presence of a poly A tail, yet the induction of immune response was not detected (OAS1 expression). In the case of expression cassette alone where a poly A signal sequence was present but the transfected construct was linear, it did induce an immune response. This indicated that the presence of a circular molecule did produce a viable poly A tail; and since the linear construct was terminated right after the poly A signal sequence, the initiation of a viable poly A tail was not initiated or was incomplete. In the case of linear constructs with a deleted poly A signal sequence immune response was initiated, indicating that the presence of a poly A tail may be required in the prevention of an immune response and in the stability of the transcribed RNA molecule (FIGS. 41-42).

The predicted mRNA from the bicistronic construct had no resemblance to miRNA and had perfect hairpin loop structure for both uPAR and uPA sequences. A 48-base sequence forming a partial dsRNA of 24 bases was introduced between uPAR and uPA sequences to enable the efficient transcription of both siRNA molecules. The bicistronic sequence was terminated with a poly A sequence coded by a BGH poly-AA signal sequence (FIG. 43).

RT-PCR for the OAS1 gene, a classic antiviral response gene, indicated that there was no immune response as in transfected control cells and EV/SV. RT-PCR was also conducted for uPA and uPAR transcripts in antisense and RNAi-transfected cells. As determined by RT-PCR, no change in uPAR or uPA mRNA transcripts was seen in the antisense transfected cells, whereas mRNA levels of uPAR or uPA in the RNAi-transfected cells were reduced, indicating a destruction of the respective mRNA (24 h). The mechanism of RNAi involves the destruction of the target mRNA molecules. OAS1 expression was similar to control groups (PGFP, pEV and pSV) indicating the absence of cellular level immune response (FIG. 44).

Example 34

In Situ Localization of RNAi Expressing Vectors

Paraffin-embedded sections were deparaffinized and rehydrated as per standard protocol under nuclease-free conditions. These sections were treated with proteinase K to reveal any DNA bound to proteins. DNA was denatured as per standard protocol. pcDNA 3 plasmid was taken and the expression cassette containing the CMV promoter (Nru I Hind III digest) was labeled with thermostable alkaline phosphatase (Amersham Biosciences, Piscataway, N.J.) and hybridized to the treated sections. Hybridization was conducted as per the manufacturer's instructions. Mock-injected mice did not show any activity of alkaline phosphatase, whereas mice treated with IP injections of EV, SV, puPAR, puPA or pU2 showed activity of alkaline phosphatase, indicating the presence of the CMV promoter. Activity of alkaline phosphatase was in most cases localized around blood vessels and showed radiating patterns around vasculature, indicating the crossing of the CMV-bearing plasmid vectors across the blood brain barrier (FIG. 45).

Example 35

Determination of Interferon Response Gene OAS1 for uPAR-Cathepsin B Circular Plasmids Plasmid constructs for empty vector (EV), scrambled vector (SV), uPAR (pU), cathepsin B (pC), and the bicistronic construct for uPAR and cathepsin B (pCU) were used to determine the level of interferon induction in the SNB19 human glioma cell line. OAS1 gene expression was used as an indicator for interferon induction. Circular plasmids (C), linear expression cassette (L), and BGH poly A signal sequence deleted linear expression cassette (-A) were used. SNB19 cells were transfected with equivalent amounts of the above plasmid or expression cassettes and total RNA was isolated after 48 h of transfection using standard protocols. RT PCR was performed on the above samples and the levels of OAS1 amplicon were determined on an agarose gel. The primers used for OAS1 amplification were 5'-aggtggtaaagggtggctcc-3' (SEQ ID NO: 13) and 5'-acaaccaggtcagcgtcagat-3' (SEQ ID NO: 14). Primers used to amplify the expression cassette from the above plasmids (EV, SV, pU, pC and pCU) were: forward primer 5'ctggtgtcgacctgcttccgcgatgtacgggc3' (SEQ ID NO: 15) and reverse primer 5'ctggtgtcgacatccccagcatgc-ctgctat3 (SEQ ID NO: 16).

RT-PCR for OAS1 (2'5'-oligoadenylate synthetase) mRNA induction was performed to determine the relevance of a poly A signal sequence. Circular, linear (expression cassette alone) and expression cassette with deleted poly A signal sequence were used (C, L, and -A respectively). In the case of EV and SV, no over induction of OAS1 mRNA was detected. In the case of EV, the overall length of the transcript was not expected to be more than 1 kb and the predicted structure of the transcript had no significant dsRNA structure to induce an immune response with or without a poly A tail as seen in the figure (also in SV). In contrast, with pU, pC and pCU the predicted secondary structure did possess dsRNA structures but with the presence of a poly A tail, yet the induction of immune response was not detected (OAS1 expression). In the case of expression cassette alone where a poly A signal sequence was present but the transfected construct was linear, it did induce an immune response. This indicated that the presence of a circular molecule did produce a viable poly A tail; and since the linear construct was terminated right after the poly A signal sequence, the initiation of a viable poly A tail was not initiated or was incomplete. In the case of linear constructs with a deleted poly A signal sequence immune response was initiated, indicating that the presence of a poly A tail may be important in the prevention of an immune response and in the stability of the transcribed RNA molecule.

The induction of OAS1 was examined in intracranial xenograft tumors treated with EV, SV, pU, pC and pCU. Normal mice that were treated with interferon α (3 μg/mouse) intracranially were included and sacrificed 5 hours later. Spleen and liver were used as normal control tissues to substantiate the specificity of the antibody where the presence of OAS 1 expression was present under normal conditional. In addition to immunohistochemistry, in situ hybridization was performed in these tissues using sense (acaaccaggtcagcgtca-gat) oligos to determine OAS1 mRNA levels. Only very minimal expression of OAS1 mRNA and protein in the mouse brains with intracranial tumors or in the brains of the mice treated with pU, pC and pCU. Notably, there was no induction of OAS1 in the pCU-treated group.

Example 36

Intraperitoneal Injection of an hpRNA-Expressing Plasmid Targeting uPAR and uPA Retards Angiogenesis and Inhibits Intracranial Tumor Growth in Nude Mice This Example demonstrates the therapeutic potential of using plasmid expressed RNAi targeting uPAR and uPA to treat human glioma. Plasmid based RNAi was used to simultaneously downregulate the expression of uPAR and uPA in SNB19 glioma cell lines and EGFR overexpressing 4910 human glioma xenografts in vitro and in vivo, and the intraperitoneal route was evaluated for RNAi expressing plasmid administered to target intracranial glioma.

Total RNA was isolated from control cells and cells transfected with empty vector (EV), scrambled vector (SV), puPAR, puPA or pU2 (FIG. 46). RNA was also isolated from cells transfected with antisense expression vectors for uPAR and uPA, and from cells transfected with a plasmid vector expressing siRNA for GFP. RT-PCR was performed per standard protocol for uPAR and uPA. To determine whether these siRNA-expressing plasmids induce an interferon response, RT-PCR for OAS1 was performed. As a positive control, cells were also treated with interferon alpha (0.5 ng/ml) to visualize OAS1 mRNA expression (FIG. 46A). SNB19 cells were transfected with mock, EV/SV, puPA, puPAR or pU2. After 48 h, cells were collected and total cell lysates were prepared in extraction buffer containing Tris [0.1 M (pH 7.5)], Triton-X114 (1.0%), EDTA (10 mM), aprotinin, and phenylmethyl-sulfonyl fluoride as described previously. Subsequently, 20 μg of protein from these samples were separated under nonreducing conditions by 12% SDS-PAGE and transferred to nitrocellulose membranes (Schleicher & Schuell, Keene, N.H.). The membranes were probed for 2 h with antibodies against uPAR (FIG. 46B). The membranes were subsequently washed three times with PBS to remove excess primary antibody, incubated with a secondary antibody as required, and then developed per standard protocol. For loading control, the membranes were stripped and probed with monoclonal antibodies for GAPDH. The enzymatic activity and molecular weight of electrophoretically separated forms of uPA were determined from the conditioned media of SNB19 cells transfected with mock, EV/SV, puPA, puPAR or pU2 by SDS-PAGE (FIG. 46B). Western blot analysis was also performed using cell lysates of 4910 EGFR-overexpressing 4910 xenograft cells transfected with mock, EV/SV, puPA, puPAR or pU2. Western blots were immunoprobed for EGFR and VEGF per standard protocols (FIG. 46C).

To visualize VEGF and EGFR expression in EGFR-overexpressing 4910 cells, $1 \times 10^4$ cells were seeded on vitronectin-coated 8-well chamber slides, incubated for 24 h, and transfected with mock, empty vector (EV) and a vector expressing siRNA for uPAR (puPAR), uPA (puPA), or both (pU2). After 72 h, cells were fixed with 3.7% formaldehyde and incubated with 1% bovine serum albumin in PBS at room temperature for 1 h for blocking. After the slides were washed with PBS, either IgG anti-VEGF (mouse) or IgG anti-EGFR (mouse) was added at a concentration of 1:200. The slides were incubated at room temperature for 1 h and washed three times with PBS to remove excess primary antibody. Cells were then incubated with anti-mouse FITC conjugated IgG (1:500 dilution) for 1 h at room temperature. The slides were washed three times, covered with glass cover slips with DAPI-containing mounting media, and fluorescent photomicrographs were obtained. Expression of EGFR and VEGF in control and EV/SV-, puPAR-, puPA- and pU2-transfected 4910 cells was determined. To determine in vitro angiogenesis, 4910 or SNB319 cells ($2 \times 10^4$/well) were seeded in 8-well chamber slides and transfected with mock, empty vector (EV) and a vector expressing siRNA for uPAR (puPAR), uPA (puPA), or both (pU2). After a 24 h incubation period, the conditioned medium was removed and added to $4 \times 10^4$ human dermal endothelial cell monolayer in 8-well chamber slides. The human dermal endothelial cells were allowed to grow for 72 h. Cells were then fixed in 3.7% formaldehyde, blocked with 2% bovine serum albumin, and incubated with factor VIII primary antibody (DAKO Corp., Carpinteria, Calif.). The cells were then washed with PBS and incubated with a FITC-conjugated secondary antibody for 1 h. The slides were washed and the formation of capillary-like structures was observed using fluorescent microscopy. Endothelial cells were also grown in conditioned media of 4910 or SNB19 cells transfected with mock, empty vector (EV) and a vector expressing siRNA for uPAR (puPAR), uPA (puPA), or both (pU2). Endothelial cells were allowed to grow for 72 h, and H&E stained for visualization of network formation. As determined by in vitro angiogenesis quantification, similar results were obtained for SNB19 and 4910 cells. The degree of angiogenic induction was quantified for both SNB19 and 4910 cells based on the numerical value for the product of the number of branches and number of branch points (*p value=0.005) (FIG. 47). In vivo angiogenic assay using the dorsal skin fold model was performed as described herein. Briefly, the animals were implanted with diffusion chambers containing control or pU2-transfected 4910 cells in a dorsal cavity. Ten days after implantation, the animals were sacrificed and vasculature flushed with FITC solution. The skin fold covering the diffusion chamber was observed for FITC fluorescence and in visible light for the presence of tumor-induced neovasculature (TN) and pre-existing vasculature (PV).

Spheroids of SNB19 or 4910 cells were prepared by seeding a suspension of $2 \times 10^6$ cells in Dulbecco's modified Eagle medium on ultra low attachment 100 mm tissue culture plates and cultured until spheroid aggregates formed. Spheroids measuring ~150 μm in diameter (about $4 \times 10^4$ cells/spheroid) were selected and transfected with mock, empty vector (EV) and a vector expressing siRNA for uPAR (puPAR), uPA (puPA) or both (pU2). Three days after infection, single glioma spheroids were placed in the center of each well in vitronectin-coated (50 μg/ml) 96-well microplates and 200 μl of serum-free medium was added to each well. Spheroids were incubated at 37° C. for 24 h, after which the spheroids were fixed and stained with Hema-3 and photographed. Cell migration from spheroids to monolayers was quantified using a microscope calibrated with a stage and ocular micrometer and represented graphically (FIG. 48A). In vitro invasion of SNB19 and 4910 cells was determined by measuring the cells that invaded through matrigel-coated (Collaborative Research, Inc., Boston, Mass.) transwell inserts (Costar, Cambridge, Mass.). Briefly, transwell inserts with 8 μm pores were coated with a final concentration of 1 mg/ml of matrigel, SNB19 cells transfected with mock, EV/SV, puPAR, puPA or pU2 were trypsinized, and 200 μl aliquots of cell suspension ($1 \times 10^6$ cells/ml) were added to the wells in triplicate. After a 24 h incubation period, cells that passed through the filter into the lower wells were quantified as described earlier and expressed as a percentage of cells in the lower wells. Cells on the lower side of the membrane were fixed, stained with Hema-3 and quantified as percent invasion (FIG. 48B). SNB19 and 4910 spheroids were cultured in 6-well ultra low attachment plates. Briefly, $3 \times 10^6$ cells were suspended in 10 ml of medium, seeded onto the plates and cultured until spheroids formed. Spheroids, 100-200 μm in diameter, were selected and transfected with mock, EV/SV, puPAR, puPA or pU2. Three days after infection, tumor spheroids were stained with the fluorescent dye DiI and confronted with fetal rat brain aggregates stained with DiO. The progressive destruction of fetal rat brain aggregates and invasion of SNB19 cells were observed by confocal laser scanning microscopy and photographed. The remaining volume of the rat brain aggregates at 24, 48 and 72 h were quantified using image analysis software as described previously and graphically represented (FIG. 48C).

As shown in FIG. 49, $2 \times 10^6$ 4910 xenograft tumor cells were intracerebrally injected into nude mice. Ten days after tumor implantation, the mice were treated with intraperitoneal injections of pU2 (150 μg/injection/mouse) every other day three times. Control mice were either injected with PBS alone or with an empty plasmid vector (150 μg/injection/mouse). Five weeks after tumor inoculation, six mice from each group were sacrificed via cardiac perfusion with 3.5% formaldehyde in PBS, their brains removed, and paraffin sections prepared. Sections were stained with hematoxylin and eosin to visualize tumor cells and to examine tumor volume (arrows point to approximate site of intracranial implantation site) (FIGS. 49A & 5B). To visualize the expression levels of uPAR and uPA in intracranial tumors, mouse brains were fixed in formaldehyde and embedded in paraffin per standard protocols. Sections were deparaffinized, blocked in 1% BSA in PBS for 1 h, and subsequently transferred to primary antibody (uPAR and uPA) diluted in 1% BSA in PBS (1:500). Sections were allowed to incubate in the primary antibody solution for 2 h at 4° C. in a humidified chamber, followed by a wash in 1% BSA in PBS and placed in a solution with the appropriate (anti-mouse and anti-rabbit FITC) secondary antibody. The sections were allowed to incubate with the secondary antibody for 1 h and visualized using a confocal microscope. Images were obtained for FITC. Transmitted light images were also obtained after H&E staining to visualize the morphology of the sections. A control study was performed using a normal rabbit immunoglobulin fraction as the primary antibody (control Ab) instead of uPAR or uPA (FIG. 49C). In situ hybridization was performed to determine the presence of transfected plasmid intracranially after intraperitoneal injections. Briefly, ten days after tumor implantation the mice were treated with intraperitoneal injections of control, EV/SV, puPAR, puPA or pU2 (150 µg/injection/mouse) every other day three times. Control mice were injected with PBS alone. Five weeks after tumor inoculation, six mice from each group were sacrificed and brains processed as described in Methods. Sections were deparaffinized and probed for pcDNA3-CMV promoter using specific alkaline phosphatase-labeled DNA oligo (CTGGTGTCGACCT-GCTTCCGCGATGTACGGGC) (SEQ ID NO: 15) per standard protocols. The presence of CMV promoter was determined by the development of a blue precipitate of NBT alkaline phosphatase substrate. Arrows point to region of localization (FIG. 49D). The presence of plasmids intracranially was also determined by PCR amplification of CMV to BGH construct region of the plasmid using deparaffinized intracranial sections of control, EV/SV-, puPAR-, puPA- or pU2-intraperitoneally injected mice. To determine if interferon induction was present intracranially, total RNA was isolated from fresh or paraffin-embedded brain tissue from mice injected with control, EV/SV, puPAR, puPA, pU2, or interferon (0.5 ng) intracranially and RT-PCR was performed using primers specific for OAS1 (FIG. 49E). Nude mice were implanted with intracranial xenograft tumors and their survival ability was determined. Two sets of animals were used (6 mice/group). Both sets of mice were implanted with intracranial xenograft tumors as described previously. Ten days after tumor implantation, the mice were treated with intraperitoneal injections of pU2 plasmid (150 µg/injection/mouse) three times every other day. Control mice were either injected with PBS alone or with empty plasmid vector (150 µg/injection/mouse). The mice were maintained in clean room conditions and monitored every day for 112 days after which the experiment was artificially terminated. Brains were harvested, paraffin embedded, sectioned, and H&E stained as per standard protocols. Survival curve was plotted per standard methods and graphically represented (FIG. 49F).

Plasmid mediated RNAi targeting uPAR and uPA did not induce OAS1 expression as seen from RT-PCR analysis. In 4910 EGFR-over expressing cells, downregulation of uPAR and uPA induced the downregulation of EGFR and VEGF and inhibited angiogenesis in both in vitro and in vivo angiogenic assays. In addition, invasion and migration were inhibited as indicated by in vitro spheroid cell migration, matrigel invasion and spheroid invasion assays. OAS1 expression was not observed in mice with pre-established intracranial tumors, which were given intraperitoneal injections of plasmid expressing siRNA targeting uPAR and uPA. Furthermore, the siRNA plasmid targeting uPAR and uPA caused regression of pre-established intracranial tumors when compared to the control mice. Thus, the plasmid expressed RNAi targeting uPAR and uPA via the intraperitoneal route is clinically relevant for the treatment of glioma.

The delivery approach of Ad-vectors and antisense technology to intracellularly target RNA seems to be a crucial limiting factor in exerting its inhibitory effect on the targeted molecule. The siRNA duplex is significantly more stable in cells than the cognate single stranded sense or antisense RNA, with transcription, under the control of the identical promoter in each case. A single construct driven by a cytomegalovirus promoter (CMV) was used to deliver hpRNA molecules for both uPAR and uPA. Vectors expressing hpRNA molecules for more than one target molecule using a single promoter and the subsequent, effective inhibition of glioma cell invasion, angiogenesis and tumor growth both in vitro and in vivo are demonstrated.

Direct intraperitoneal injections of plasmids expressing siRNA targeting uPAR and uPA inhibited intracranial tumor growth in nude mice. Extracellular matrix (ECM) destruction is dependent on the expression of proteases, which are known to be overexpressed in gliomas. A simple cytomegalovirus plasmid vector driving the production of hairpin-like RNA molecules was utilized therapeutically. The use of an mRNA-like molecule possessing a poly A tail and having 21 bp inverted repeats, which target uPAR and uPA, did not induce an interferon-like response, which is not desirable. Using lentiviral vectors induced OAS1. Induction of OAS1 was not observed herein. The presence of a poly A tail mimicking cellular mRNA and appearing as "self" to the cell may be responsible for the lack of undesirable OAS1 response. Target mRNA molecule downregulation was observed with siRNA, whereas no downregulation was observed with the use of an antisense sequence. With an antisense approach, equimolar quantities of the antisense molecule are required to silence the target gene. This is not required with RNAi where the RISC behaves like a catalyst and is reused. In essence, a small amount of RNAi inducing molecules, such as siRNA or hpRNA, is sufficient to induce silencing of target genes. Data demonstrate that therapeutic use of RNAi to treat gliomas is efficient.

Simultaneous downregulation of uPAR and uPA causes the downregulation of EGFR and VEGF in EGFR-overexpressing glioma xenograft cells (4910). In situ studies confirm western blot analysis results in also demonstrating the downregulation of EGFR and VEGF. In situ angiogenic assays have shown that endothelial cells co-cultured with EGFR-overexpressing 4910 cells induce the endothelial cells to form a network-like pattern mimicking tumor angiogenesis. Progressive reduction in the network formation was seen in puPAR- and puPA-transfected cells. In cells transfected with pU2, complete regression of network formation was observed, indicating that the simultaneous downregulation of uPAR and uPA causes the tumor cells to retard or stop secreting factors necessary for the induction of angiogenesis. The dorsal skin fold assay, an in vivo angiogenic assay, revealed complete inhibition of angiogenesis by pU2-transfected 4910 cells. An adenovirus-mediated strategy required 100 MOI of virus particles were required to achieve the same effect as 6 µg of plasmid. Similar results were observed with the other assays. For example, spheroid migration was significantly inhibited in pU2-treated SNB19 and 4910 xenograft cells. Invasion studies demonstrated that after transfection with pU2, both SNB19 and 4910 cells exhibited a significant reduction in their invasive ability, only 5%-8% invasion when compared to the controls. From these spheroid invasion assay results, it is clear that the simultaneous downregulation of uPAR and uPA retards the invasion of fetal rat brain aggregates.

Animal studies demonstrate that the simultaneous downregulation of uPAR and uPA causes the regression of intracranial tumors. Nude mice implanted with 4910 xenograft cells intracranially usually die in 4 weeks due to tumor invasion. In contrast, mice injected with pU2 intraperitoneally do not exhibit tumor establishment and survived for over 112 days after implantation. The in situ hybridization studies indicated that there was translocation of the intraperitoneally injected plasmid to the brain. The plasmids may pass through the blood brain barrier (BBB) probably due to the already compromised BBB at the tumor site. The presence of the plasmid intracranially in control was seen primarily surrounding vessels (not shown). As such, the potential for using siRNA vectors for therapy is effective. In spite of being injected intraperitoneally, siRNA-expressing plasmids localize intracranially and effectively downregulate uPAR and uPA. RT-PCR of the brain tissue showed that even though plasmid localization was observed in the brain, no OAS1 induction was detected. This indicates that the presence of a poly A tail probably prevented the induction of an interferon-like response. the RNAi-mediated downregulation of uPAR and uPA has clear clinical implications for the treatment of gliomas as well as other cancers.

Example 37

Downregulation of uPAR and MMP-9 Results in Overexpression of APAF-1, Nuclear Accumulation of AIF and Modulates NIK Expression in Human Glioma SNB19 Cells Malignant gliomas are characterized by invasive and infiltrative behavior that generally involves the destruction of normal brain tissue. Strategies to treat infiltrating gliomas, such as chemotherapy and gene therapy, have remained largely unsuccessful. The infiltrative nature of gliomas can be attributed largely to proteases, which include serine, metallo and cysteine proteases. A relationship between uPAR and MMP-9 expression, which is indicative of the infiltrative phenotype of gliomas. Simultaneous downregulation of uPAR and MMP-9 using RNAi induced apoptosis in the SNB19 human glioma cell line. Using western blot analysis, the levels of APAF-1 were observed to be increased in uPAR- and MMP-9-downregulated cells, whereas the levels of TRADD and TRAF-2 decreased. Further, levels of NIK increased in uPAR- and MMP-9-downregulated cells when compared to controls. Levels of NIK decreased in uPAR-downregulated cells but no appreciable change was observed in MMP-9-downregulated cells. To determine the nuclear localization of AIF and Iκαβ, the levels of AIF, Iκβα, and p-Iκβα were analyzed in the cytosolic and nuclear fractions of cells downregulated for uPAR, MMP-9, or uPAR and MMP-9 simultaneously. Western blot analysis revealed that the simultaneous downregulation of uPAR and MMP-9 resulted in the translocation of AIF to the nucleus and also inhibited nuclear localization of p-Iκβα To confirm the involvement of AIF, FACS analysis was performed to determine the integrity of the mitochondrial membrane using the Mito-PT method and immunolocalization of AIF. FACS analysis showed that the simultaneous downregulation of uPAR and MMP-9 caused a collapse in the mitochondrial cell membrane. Immunolocalization of AIF revealed that in uPAR- and MMP-9-downregulated cells, AIF translocates to the nucleus, thereby enabling the induction of apoptosis. Western blot analysis of PARP demonstrated an increase in cleavage, which is indicative of caspase activation and DNA degradation. Tunnel assay confirmed DNA degradation in uPAR- and MMP-9-downregulated cells. The results demonstrate that the simultaneous downregulation of uPAR and MMP-9 induces APAF-1 and AIF-mediated apoptosis and shows therapeutic potential for glioma therapy.

Thus, The simultaneous suppression of uPAR and MMP-9 in SNB19 human glioma cells causes: overexpression of APAF-1; retardation of phosphorylated IB nuclear accumulation; accumulation of cells in sub G phase; nuclear translocation of AIF; collapse in the mitochondrial membrane potential; and activation of caspases.

Example 38

Simultaneous Downregulation of uPAR and MMP-9 Induces Apoptosis Via Upregulation of MAP4K and JUN and Retards Nuclear Localization of CD44ICD and NFκB in Human Glioma Xenograft Cells Glioblastoma multiforme is a highly malignant, primary central nervous system neoplasm that is extremely refractory to therapy. Glioblastoma are resistant to treatment due to the tendency of the tumor cells to invade normal brain tissue. Simultaneous downregulation of uPAR and MMP-9 resulted in the regression of pre-established intracranial tumors in nude mice. Molecular mechanisms involved in glioma tumor regression are analyzed via the simultaneous downregulation of uPAR and MMP-9. The results from the RT-PCR real time arrays show that the simultaneous downregulation of uPAR and MMP-9 caused a 23-fold upregulation of MAP4K, a 5-fold increase in JUN, and a 5-fold decrease in CDKN1A, which preceded caspase 9-mediated apoptosis. To determine the involvement of CD44 in uPAR and MMP-9 downregulated cells, CD44 levels were measured in cytoplasmic and nuclear extracts; these analyses indicated that the levels of CD44ICD in the nucleus were reduced when compared to controls. CD44 has been shown to be involved in multiple functions and is also suspected to have transcriptional activity. From Western blots of nuclear and extracellular fractions of CD44 under various treatment conditions using antibody for total CD44, localization of CD44ICD was shown to be in the nucleus. CD44 was detected in the conditioned media indicating its cleavage by various proteases such as MT1-MMP and MMP-9. Total CD44 levels decreased in uPAR and MMP-9 downregulated cells, and the CD44ICD domain in the nucleus was almost undetectable. Caspase 9 activation was initiated and accompanied the dephosphorylation of ERK1/2, and nuclear and cytoplasmic levels of NFκB p65 and 50 were decreased. Mobility shift assay with oligos specific for NF B further confirmed NFκB downregulation. The real time RT-PCR array results showed that MEK levels did not change and the levels of MAP3K2 decreased, whereas the levels of MAP4K1 levels increased, thereby indicating the activation of the JUN pathway. Taken together, it is evident that glioma cells, which overexpress uPAR and MMP-9, have the potential to undergo apoptosis upon the downregulation of uPAR and MMP-9. Hence, the simultaneous targeting of uPAR and MMP-9 is clinically relevant for glioma therapy.

Thus, The simultaneous down regulation of uPAR and MMP-9 in human glioma xenograft cells causes the: up regulation of MAP4K1 and JUN; retardation of the accumulation of CD44 on cell surface; inhibition of the nuclear translocation of CD44; retardation of translocation and expression of NF B p50 and p65 to the nucleus; and induction of Caspase 9 cleavage.

MATERIALS AND METHODS

Construction of Small Hairpin RNAs Expressing Plasmids:

uPA-uPAR: Small interfering oligonucleotides specific for uPA from 346 to 367 bases (agcttGagagccctgctggcgcgc-catatataatggcgcgccagcagggctctca) (SEQ ID NO: 17) and for uPAR from 77 to 98 bases (gatccTacagcagtggagagcgattatatataataatcgctctccactgctgtag) (SEQ ID NO: 18) were synthesized and annealed. An uPA-uPAR RNAi plasmid vector that expresses shRNAs for both uPA and uPAR under the control of a human CMV promoter was constructed by inserting pairs of the annealed DNA oligonucleotides specific for uPA at the Hind III site and uPAR at BamHI site sequentially into the pcDNA3 vector (sh-uPAuPAR). Also, shRNA expression vectors for uPA (sh-uPA) and uPAR (sh-uPAR) singly were constructed. A pcDNA3-scrambled vector with an imperfect sequence, which does not form a perfect hairpin structure, was used to develop the scrambled vector for use as a control. The empty vector (EV) and scrambled vector (SV) controls have been tested in multiple cell lines and does not demonstrate any toxicity to cells as demonstrated by MTT assay after transfection as well as having no effect on the expression of housekeeping genes, GAPDH and ÿ-actin.

uPAR and MMP-9. pcDNA 3 was used for the construction of a vector expressing siRNA for both uPAR and MMP-9 downstream of the cytomegalovirus (CMV) promoter (Scheme 1). The uPAR sequence from +77 to +98 was used as the target sequence and for convenience a self-complementary oligo was used. The uPAR sequence 21 bases in length with a 9 base loop region and BamHI sites were incorporated at the ends (gatcctacagcagtggagagcgattatatataataatcgctctccactgctgtag) (SEQ ID NO: 18) The oligo was self-annealed in 6×SSC using standard protocols and ligated on to the BamHI site of a pcDNA-3 vector plasmid. Similarly, a MMP-9 complementary sequence from +360 to +381 (aattcaagtggcaccaccacaacaatatataattgttgtggtggtgccacttg) (SEQ ID NO: 19) with EcoRI sites incorporated at the ends was ligated into the EcoRI site of the vector containing the siRNA sequence for uPAR. This finally resulted in a siRNA expression plasmid for uPAR and MMP-9 with a 35 bp separation. The orientation of either insert did not matter since the oligos are self-complementary and have a bilateral symmetry. The SV40 terminator served as a stop signal for RNA synthesis.

Cathepsin B and uPA: pcDNA 3 was used for the construction of a vector expressing siRNA for both cathepsin B and uPAR downstream of the cytomegalovirus (CMV) promoter (FIG. 17). The uPAR sequence from +77 to +98 was used as the target sequence and for convenience a self-complementary oligo was used. The uPAR sequence 21 bases in length with a 9 base loop region with BamHI sites incorporated at the ends (gatcctacagcagtggagagcgattatatataataatcgctctccactgctgtag) (SEQ ID NO: 18) was used. The oligo was self-annealed in 6×SSC using standard protocols and ligated on to the BamHI site of a pcDNA-3 vector plasmid. Similarly, a cathepsin B complementary sequence from +732 to +753 (tcgaggtggcctctatgaatcccaatatataattgggattcatagaggccacc) (SEQ ID NO: 20) with XhoI sites incorporated at the ends was ligated into the XhoI site of the vector containing the siRNA sequence for uPAR. This finally resulted in a siRNA expression plasmid for cathepsin B and uPAR designated pCU. Single siRNA expression vectors for uPAR (pU) and cathepsin B (pC) were also constructed. The orientation of either insert in the single or bisistronic did not matter since the oligos were self-complementary and had bilateral symmetry. BGH poly A terminator served as a stop signal for RNA synthesis for all three constructs.

uPAR, uPA and MMP-9: pcDNA3 was used for the construction of a vector expressing siRNA for uPAR, uPA and MMP-9 downstream of the cytomegalovirus (CMV) promoter. The uPAR sequence from +77 to +98 was used as the target sequence and for convenience a self-complementary oligo was used. The uPAR sequence 21 bases long with a 9 base loop region with BamHI sites incorporated at the ends (gatcctacagcagtggagagcgattatatataataatcgctctccactgctgtag) (SEQ ID NO: 18) was used. The oligo was self-annealed in 6×SSC using standard protocols and ligated into the BamHI site of a pcDNA3 vector plasmid. Similarly, uPA complementary sequence from +346 to +367 (agcttgagagccctgctgcgcgccatatataatggcgcgccagcagggctctca) (SEQ ID NO: 17) with HindIII sites incorporated at the ends was ligated into the HindIII site and MMP-9+360 to +381 (aattcaagtggcaccaccacaacaatatataattgttgtggtggtgccacttg) (SEQ ID NO: 19) was ligated into the EcoRI site of the vector containing the siRNA sequence for uPAR and uPA. This finally resulted in a siRNA expression plasmid for uPAR, uPA and MMP-9 designated pU$_2$M. Single siRNA expression vectors for uPAR (puPAR), uPA (puPA) and MMP-9 (pMMP-9) were also constructed. The orientation of the insert in either the single or tricistronic construct was not a factor because the oligos were self-complementary and had bilateral symmetry. BGH poly A terminator served as a stop signal for RNA synthesis for all four constructs.

Cathepsin B and MMP-9: Self-complementary inverted repeat sequences spaced by a 9 base G C deficient region targeted to cathepsin B (732 to 753) and MMP-9 (360 to 381) were synthesized. Oligos for cathepsin B were terminated with XhoI sites and the oligos for MMP-9 were terminated with EcoR1 and self annealed by heating to 100° C. for 5 min and cooled to room temperature in 6×SSC which would result in the formation of double-stranded DNA molecules with the respective sticky restriction site ends. These dsDNA molecules were ligated to the XhoI and EcoR1 sites of the pCDNA plasmid vector, resulting in the formation of a plasmid containing inverted repeats for cathepsin B and MMP-9 down stream of the CMV promoter and terminated by a SV40 terminator. The resultant plasmid termed pCM transfected to mammalian cells would result in the production of a dual hairpin siRNA molecule targeted both to Cathepsin B and MMP-9 which would be further processed by a dsRNA recognizing enzyme (DICER) to produce individual siRNA molecules to induce RNAi (Scheme 1).

Cell Culture and Transfection Conditions:

Prostate cancer cells: Human prostate cancer cell lines LNCaP, DU145 and PC3 were obtained from the American Type Culture Collection (Manassas, Va.). LNCaP cells were grown in RPMI medium supplemented with 2 mM L-glutamine, 1.5 g/L sodium bicarbonate, 4.5 g/L glucose, 10 mM HEPES, and 1.0 mM Sodium pyruvate (Invitrogen, Carlsbad, Calif.). PC3 and DU145 cells were grown in minimum essential medium. Both media contained 10% fetal bovine serum (GIBCO BRL, Lewisville, Tex.) and 5% penicillin/streptomycin and were maintained in a 37° C. incubator in a 5% CO$_2$ humidified atmosphere. Transfections were performed using Lipofectamine™ 2000 reagent (Life technologies, Rockville, Md.) per the manufacturer's instructions. After 72 h of transfection, cells were used for cell proliferation assays, immunoblot analysis, RT-PCR analysis, Matrigel invasion assay, DNA fragmentation assay, EMSA assay and caspase activity assay. For DAPI and double immunostaining, transfections were carried out in Lab-Tek II chamber slides (Nalge Nunc International, Naperville, Ill.).

Glioblastoma cells: The human glioblastoma cell line SNB19 was maintained in DMEM F-12 (Sigma Chemical Co., St. Louis, Mo.) supplemented with 10% FCS, 100-µg/ml streptomycin and 100-units/ml penicillin (Invitrogen, Carlsbad, Calif.) at 37° C. in a humidified 5% CO$_2$ atmosphere. Cells were transfected with pC pU or pCU plasmid expressing siRNA using the Lipofectamine reagent (Invitrogen Grand Island, N.Y.) as per manufacturer's instructions. After transfection, cells were incubated in serum-containing medium for 48 h.

Fibrin zymography: The enzymatic activity and molecular weight of electrophoretically separated forms of uPA were determined in conditioned medium of prostate cancer cell lines LNCaP, DU145 and PC3 by SDS-PAGE. Briefly, the SDS-PAGE gel contains acrylamide to which purified plasminogen and fibrinogen were substrates before polymerization. After polymerization, equal amounts of proteins in the samples were electrophoresed and the gel was washed and stained. SNB19 cells transfected with EV/SV puPAR, puPA, pMMP-9 and pU$_2$M were also performed as described herein.

Gelatin zymography. Conditioned media were collected from cells transfected with EV/SV, puPAR, pMMP-9 and pUM and centrifuged to remove cellular debris. Twenty micrograms of the resulting samples were assayed for gelatinase activity using 10% sodium dodecyl sulfate-polyacrylamide gels containing gelatin (0.5 mg/ml). Gels were stained with Amido black (Sigma Aldrich ST LOUIS Mo.) and gelatinase activity was visualized as areas of clear bands in gels. SNB19 cells transfected with EV/SV, puPAR, puPA, pMMP-9 and pU$_2$M were also performed as described herein.

Reverse Transcription-PCR Analysis:

uPA-uPAR: Cellular RNA was isolated using the Qiagen RNeasy kit and 1 g of RNA was DNase treated (10 units/g of RNA, 1 h) and used as a template for the reverse transcription reaction (RT, 20 l). RT reaction mix (Invitrogen) contained 1 l (10 pm) of primers. The resultant cDNA was then used in PCR reactions and analyzed by gel electrophoresis. The following primers were used:

```
uPA-sense:
5'TGCGTCCTGGTCGTGAGCGA 3'        (SEQ ID NO: 21);

uPA-antisense:
5'CTACAGCGCTGACACGCTTG 3'        (SEQ ID NO: 22);

uPAR-sense:
5'CATGCAGTGTAAGACCCAACGGGGA 3'   (SEQ ID NO: 23);

uPAR-antisense:
5'AATAGGTGACAGCCCGGCCAGAGT 3'    (SEQ ID NO: 24);

GAPDH-sense:
5'CGGAGTCAACGGATTTGGTCGTAT 3'    (SEQ ID NO: 25);
and

GAPDH-antisense:
5'AGCCTTCTCCATGGTGGTGAAGAC 3'    (SEQ ID NO: 26).
```

TABLE 1

| RT-PCR Primers (MMP-9, UPAR) | uPAR | CATGCAGTGTAAGACCCAACGGGGA (SEQ ID NO: 23) AATAGGTGACAGCCCGGCCAGAGT (SEQ ID NO: 24) |
|---|---|---|
| | MMP-9 | GTTCGAAATTAGTTTGGTTAAC (SEQ ID NO: 27) CCGAATAACTAATATTATAAACG (SEQ ID NO: 28) |
| | GAPDH | CGGAGTCAACGGATTTGGTCGTAT (SEQ ID NO: 25) AGCCTTCTCCATGGTGGTGAAGAC (SEQ ID NO: 26) |
| Probes used | sGFP (3) | GAGCTGTTCACCGGGGTGGTG (SEQ ID NO: 29) |
| | suPAR (1) | CTACAGCAGTGGAGAGCGATT (SEQ ID NO: 30) |
| | sMMP-9(2) | CAAGTGGCACCACCACAACAA (SEQ ID NO: 31) |

RT-PCR analysis for SNB19 cells transfected with control/EV, SV, puPAR, pMMP-9 and pUM were performed as described herein.

PCR conditions were as follows: 95° C. for 5 minutes, followed by 35 cycles of 95° C. for 1 min, 55° C. for 1 minute, and 72° C. for 1 minute. The final extension was at 72° C. for 5 min. The annealing temperature varies depending upon the sequence of the various constructs and were performed following standard procedures.

PC3 Immunofluorescence detection: PC3 cells transfected with various shRNA plasmids were fixed with 4% paraformaldehyde and incubated with anti-uPA (1:500; Biomeda, Foster City, Calif.) and/or anti-uPAR (1:500; American Diagnostics Inc., Greenwich, Conn.). After washing, fluorescent secondary antibodies (Santa Cruz Biotechnology, Santa Cruz, Calif.) were added at a 1:500 dilution. The cells were again washed three times with PBS, and counter-stained with DAPI. Fluorescent images were acquired using a charge-coupled device RT Slider Spot Camera (Diagnostic Instruments Inc, Burroughs Sterling Heights, Mich.) connected to a microscope (Olympus, Melville, N.Y.) and managed by a computer equipped with the spot RT software v3.5 (Diagnostic instruments, Burroughs Sterling Heights, Mich.).

PC3 Cells Matrigel invasion assay: After transfection, cells were detached and washed twice in PBS. 5×10$^5$ cells were seeded in the upper chamber of a Transwell insert (12 μM pores) coated with Matrigel (0.7 mg/ml) (Collaborative Research Inc., Boston, Mass.). The lower chamber was filled with 400 l of RPMI medium. After a 24 h incubation period, the non-migrated cells in the upper chamber were gently scraped away and adherent cells present on the lower surface of the insert were stained with Hema-3 and photographed.

In situ caspase activity assay: Caspase activation was detected using the polycaspase detection kit (Immunochemistry Technologies, Bloomington, Ill.) per manufacturer's instructions. In this assay, the cell permeable, non-cytotoxic Fluorochrome Inhibitors of Caspases (FLICA) binds covalently to a reactive cysteine residue on the large subunit of the active caspase heterodimer, thereby inhibiting further enzymatic activity. This kit uses a carboxyfluorescein-labeled fluoromethyl ketone peptide inhibitor of many caspases (caspase 1, -3, -4, -5, -6, -7, -8 and -9; FAM-VAD-FMK), which is a generic probe for the detection of most caspases and emits green fluorescence. The green fluorescent signal is a direct measure of the amount of active caspase in the cell at the time the reagent was added. After 72 h of transfection, caspase activation was detected by staining the cells with the FAM-VAD-FMK dye (in situ marker). The bound marker was localized by fluorescence detection as observed with a confocal microscope. DAPI was used for nuclear staining.

DNA laddering assay: After transfection, cells were harvested and washed twice in PBS. Cell pellets were resuspended in lysis buffer (10 mM Tris-HCl, 400 mM NaCl, 1 mM EDTA and 1% TritonX-100) containing 0.1 mg/ml Proteinase K (Invitrogen) and then incubated at 37° C. for 2 h. DNA was cleared from the lysates by centrifugation and then extracted using an equal volume of phenol/chloroform and precipitated by adding absolute ethanol and 0.3 M sodium acetate (pH 5.2) at −80° C. for 2 h. The DNA was resuspended in Tris-EDTA buffer (10 mM Tris-HCl; pH 7.5, 1 mM EDTA), treated with RNase A at 37° C. for 1 h, and then resolved on a 1.5% agarose gel stained with ethidium bromide (0.5 g/ml).

Electrophoretic mobility shift assay (EMSA): After transfection, nuclear proteins were extracted using a protein extraction kit (Ambion, Austin, Tex.) as per the manufacturer's instructions. Concentrations of nuclear proteins were determined on diluted samples using a bicinchoninic acid procedure (Pierce Biochemical Company, Rockford, Ill.). Interaction between Stat 3 in the protein extract and DNA probe was investigated using an electrophoretic mobility shift assay (EMSA) kit from Panomics (Redwood City, Calif.) as per the manufacturer's instructions.

DNA fragment end labeling assay: shRNA-treated or control prostate tumor tissue sections (5 M thick) were de-paraffinized and rehydrated. Next, the tissue sections were permeabilized by covering the entire specimen with Proteinase K solution (20 g/ml Proteinase K in 10 mM Tris, pH 8) and incubated for 20 min at room temperature. The tissue sections were then washed in Tris-buffered saline (1×TBS, 20 mM Tris pH 7.6, 140 mM NaCl). Inactivation of endogenous peroxidases was accomplished by immersing the tissue sections in 3% hydrogen peroxide diluted in methanol for 5 min at room temperature. The glass slides were then placed in Klenow equilibration buffer (50 mM Tris pH 8, 50 mM NaCl, 10 mM $MgCl_2$) for 30 min. The tissue sections were then incubated with 60 l of a solution containing a mixture of labeled and unlabeled deoxynucleotides at a ratio optimum for DNA fragment end labeling with Klenow, according to the manufacture's instructions (Klenow-FragEL DNA fragmentation detection kit, Oncogene Research Products, Cambridge, Mass.) at 37° C. for 90 min in a humidified chamber. The enzymatic reaction was stopped by incubation with EDTA (0.5 M, pH 8) for 5 min at room temperature. The slides were then washed with TBS and immersed in blocking buffer for 10 min (4% BSA in PBS) followed by incubation with 100 l of a solution containing peroxidase streptavidin for 30 min in a humidified chamber at room temperature. The tissue sections were then washed in TBS and covered with a solution containing 3,3'diaminobenzidine (DAB, 0.7 mg/ml), hydrogen peroxide and urea (0.6 mg/ml). Next, the slides were washed with distilled water and counterstained with methyl green (0.3%) for 30 sec and examined under an Olympus fluorescence microscope. The positive DNA fragment end labeled staining was scored from six randomly captured images/sample using spot RT software v3.5 (Diagnostic instruments, MI).

Orthotopic mouse prostate treatment model: Athymic male nude mice (nulnu; 6-8 weeks of age) were obtained from Harlan Sprague-Dawley (Indianapolis, Ind.). Animal handling and experimental procedures were approved by the University of Illinois College of Medicine animal experiments committee. Orthotopic implantation was carried out as described previously. Briefly, after total body anesthesia with ketamine (50 mg/kg) and xylazine (10 mg/kg), a low midline incision was made in the lower abdomen. A suspension of PC3 cells ($1\times10^6$) in 30 µl PBS was injected into a lateral lobe of the prostate and the wound was closed with surgical metal clips. This cell concentration was necessary to achieve consistent local tumor growth within 7 days of implantation. Mice were divided in to five treatment groups with six mice per treatment group. At days 7 and 14 post-implantation, a low midline incision was performed and the tumors were injected with plasmid constructs expressing sh-uPA, sh-uPAR, sh-uPA-uPAR or EV/SV controls (75 µg/150 µg each). In another set of experiments, the orthotopically-implanted mice were intratumorally coinjected with sh-uPA and sh-uPAR plasmids (150 µg each) on days 7 and 14. Mice were sacrificed 14-15 days after the final shRNA plasmid injection and the primary tumor growth and sites of metastasis were determined by visual inspection and photographed. The primary tumors were then excised, measured and weighed. Specimens were fixed in formalin and embedded in paraffin for H&E staining. Also, some of the tissue was snap frozen immediately for immunoblotting.

Western blotting. SNB19 cells were transfected with mock, empty vector, pC, pU or pCU and cultured 48 hr. At the end of incubation, cells were harvested, washed twice with cold PBS and lysed in buffer (150 mM NaCl, 50 mM Tris-Hcl, 2 mMEDTA, 1% NP-40, PH 7.4), containing protease inhibitors. Equal amounts of protein (30 µg/lane) from supernatants or cells were electrophoresed under non-reducing conditions on 10% acrylamide gels. After SDS-PAGE, proteins were transferred to a polyvinylidene difluoride membrane (Bio-Rad). To block non-specific binding, the membrane was incubated for 2 h in PBS with 0.1% Tween-20 [T-PBS] containing 5% nonfat skim milk for 2 h. Subsequently, the membrane was incubated for 2 h with antibody against cathepsin B, uPAR, ERK, pERK, FAK or pFAK respectively in T-PBS+ 5% nonfat milk. After washing in T-PBS, protein on the membrane was visualized using the ECL™ detection kit with a peroxidase-labeled antirabbit antibody (Amersham Pharmacia Biotech, Amersham, UK) per manufacturer's instructions. For loading control, the membranes were stripped and probed with monoclonal antibodies for β-actin, as per standard protocols. Immunoblot analysis for SNB19 cells were transfected with EV/SV, puPAR, puPA, pMMP-9 and $pU_2M$ were also performed as described herein. The following antibodies were used for uPA-uPAR immunoblot analysis: anti-uPA (Biomeda, Foster City, Calif.), anti-uPAR (American Diagnostics Inc., Greenwich, Conn.), anti-Bax (Santa Cruz Biotechnology, Santa Cruz, Calif.), anti-Bcl-$X_{S/L}$ (Santa Cruz Biotechnology, Santa Cruz, Calif.), anti-caspase 9 (Cell Signaling Technology Inc., Beverly, Mass.), and anti-GAPDH (Abcam, Cambridge, Mass.). Antibodies against total and phospho forms of ERK, JNK, p38 and Stat 3 were obtained from Santa Cruz Biotechnology (Santa Cruz, Calif.). Western blotting for SNB19 cells were transfected with EV/SV, puPAR, puPA, pMMP-9 and $pU_2M$ were also performed as described herein.

Immunohistochemical analysis. SNB19 cells ($1\times10^4$) were seeded on vitronectin-coated 8-well chamber slides, incubated for 24 h and transfected with EV/SV, puPAR, pMMP-9 and pUM. After another 72 h, cells were fixed with 3.7% formaldehyde and incubated with 1% bovine serum albumin in PBS at room temperature for 1 h for blocking.

After the slides were washed with PBS, either IgG anti-uPAR (rabbit) or IgG anti-MMP-9 (mouse) was added at a concentration of 1:200. The slides were incubated at 4° C. overnight and washed three times with PBS to remove excess primary antibody. Cells were then incubated with anti-mouse FITC conjugate or anti-FITC conjugates IgG (1:500 dilution) for 1 h at room temperature. The slides were then washed three times, covered with glass cover slips and fluorescent photomicrographs were obtained. Composite merged images were obtained to visualize the expression of uPAR and MMP-9 in control EV, SV, puPAR, pMMP-9 and pUM transfected cells.

SNB19 Cell proliferation assay. Cell growth was assessed by MTS assay. To detect the effect of these constructs on the growth of the SNB19 cells in vitro, viable cell mass using the Cell Titer 96™ colorimetric assay were measured. $5\times10^3$ glioblastoma cells were seeded in triplicate into 96- or 24-well plates and allowed to grow for 24 h before transfection with culture medium alone (mock), EV, SV, pC, pU and pCU vectors for 48 h. These cells were then changed to serum containing medium and allowed different time intervals. Before each time point, MTS reagent was added and continued incubation for an additional 2 h to permit color development. A490 was measured in each well using an ELISA plate reader. Absorbance readings for short term vs. long term cell cultures was compared, and the effects of these constructs were interpreted with respect to the growth of corresponding untreated/control groups. Percent inhibition of growth due to the siRNA constructs was calculated relative to the growth rate of the same cells in the same medium minus these constructs.

PC3 Cell proliferation assays: Viability of cells 72 h after transfection was evaluated using a MTT assay. MTT [3-(4,5-dimethylthiazol-2-yl)-2,5-diphenyltetrazolium bromide] (Sigma) was added to the culture medium in each well at a concentration of 500 g/ml, and plates were incubated for 4 h at 37° C. Acid-isopropanol (0.04 N HCl/isopropanol) was immediately added to all wells and mixed vigorously so that the dark blue crystals dissolved effectively. Absorbance was measured at 570 nm (Benchmark, BIORAD, Hercules, Calif.).

In vitro angiogenic assay. SNB19 cells ($2 \times 10^4$) were seeded in 8-well chamber slides and transfected with mock, EV, pU, pC and pCU as per standard protocols. After a 24 h incubation period, the medium was removed and $4 \times 10^4$ human dermal endothelial cells were seeded and allowed to co-culture for 72 h. After fixation in 3.7% formaldehyde, endothelial cells were immuno-probed for factor VIII antigen. Factor VIII antibody was purchased from the DAKO Corporation (Carpinteria, Calif.). Cells were washed with PBS and incubated with FITC conjugated secondary antibody for 1 h. and were then washed and examined under a fluorescent microscope. Similar slides of endothelial cells grown in the presence of conditioned media from the SNB19 mock, EV, pU, pC or pCU transfected cell were stained with H & E to visualize network formation. Image Pro software was used for quantification of angiogenesis, the degree of angiogenesis was measured by the following method: number of branch points and the total number of branches per point were counted at random (per 10 fields), with the product indicating the degree of angiogenesis compared to the controls. In vitro angiogenic assays for SNB19 cells ($2 \times 10^4$) seeded in 8-well chamber slides and transfected with mock/EV, puPAR, pMMP-9 and pUM were performed as described herein. Angiogenic assays for SNB19 cells ($1 \times 10^4$ well$^{-1}$) seeded in 8-well chamber slides, incubated for 24 hours and transfected with EV/SV, puPAR, puPA, pMMP-9 and pU$_2$M were performed as described herein.

4910 and SNB19 cells ($2 \times 10^4$/well) were seeded in 8-well chamber slides and transfected with mock, EV, puPAR, puPA, or pU2. After a 24 h incubation period, the conditioned medium was removed and added to a $4 \times 10^4$ human dermal endothelial cell monolayer in 8-well chamber slides and the human dermal endothelial cells were allowed to grow for 72 h. Cells were then fixed in 3.7% formaldehyde, blocked with 2% bovine serum albumin, and the endothelial cells were incubated with factor VIII primary antibody (DAKO Corp., Carpinteria, Calif.). Cells were washed with PBS and incubated with a FITC-conjugated secondary antibody for 1 h. The slides were then washed and the formation of capillary-like structures was observed by fluorescent microscopy. Endothelial cells were also grown in conditioned media of either 4910 or SNB19 cells transfected with mock, EV, puPAR, puPA or pU2. Endothelial cells were allowed to grow for 72 h and H&E stained to visualize capillary network formation. The degree of angiogenesis was quantified based on the numerical value for the product of the number of branches and number of branch points as an average of 10 fields.

Dorsal skin-fold chamber model: Athymic nude mice (nu/nu; 18 male/female, 28-32 g) were bred and maintained within a specific-pathogen, germ-free environment. The implantation technique of the dorsal skin-fold chamber model. Sterile small-animal surgical techniques were followed. Mice were anesthetized by ip injection with ketamine (50 mg/kg) zylazine (10 mg/kg). Once the animal was anesthetized completely, a dorsal air sac was made in the mouse by injecting 10 ml of air. Diffusion chambers (Fisher) were prepared by aligning a 0.45-micron Millipore membranes (Fisher) on both sides of the rim of the "O" ring (Fisher) with sealant. Once the chambers were dry (2-3 min), they were sterilized by UV radiation for 20 min. 20 µl of PBS was used to wet the membranes. $2 \times 10^6$ SNB19 cells (mock, empty vector or pCU transfected), suspended in 100-150 µl of sterile PBS, were injected into the chamber through the opening of the "O" ring. The opening was sealed by a small amount of bone wax. A 1½ to 2 cm superficial incision was made horizontally along the edge of the dorsal air sac and the air sac was opened. With the help of forceps the chambers were placed underneath the skin and sutured carefully. After 10 days the animals were anesthetized with ketamine/xylazine and sacrificed by intracardiac perfusion with saline (10 ml) followed by a 10 ml of 10% formalin/0.1 M phosphate solution and followed by 0.001% FITC solution in PBS. The animals were carefully skinned around the implanted chambers and the implanted chambers were removed from the s.c air fascia. The skin fold covering the chambers were photographed under visible light and for FITC fluorescence. The numbers of blood vessels within the chamber in the area of the air sac fascia were counted and their lengths measured. SNB19 cells transfected with EV/SV, puPAR, pMMP-9 and pUM were also utilized for dorsal skin-fold chamber model as described herein.

SNB19 Cell Migration Assay: A suspension of $2 \times 10^6$ cells in Dulbecco's modified Eagle medium of a GFP-expressing variant of SNB19 cells was seeded on ultra low attachment 100 mm tissue culture plates and cultured until spheroid aggregates formed. Spheroids measuring ~150 µm in diameter (about $4 \times 10^4$ cells/spheroid) were selected, transfected with mock, empty vector, pC, pU and pCU and cultured for 48 h. 72 h after transfection, a single glioma spheroid was placed in each well of a vitronectin-coated (50 µg/mL) 96-well microplate and cultured with 200 µl of serum-free medium. Spheroids were incubated at 37° C. for 24 h, after which the spheroids were fixed and stained with Hema-3 and photographed. The migration of cells from spheroids to monolayers was measured using a microscope calibrated with a stage and ocular micrometer and used as an index of cell migration. Glioblastoma cells were seeded in triplicate into 96- or 24-well plates and allowed to grow for 24 h before transfection with culture medium alone (mock), EV/SV, puPAR, pMMP-9 and pUM as described herein. Cell migration assays for SNB19 cells transfected with EV/SV, puPAR, pMMP-9 and pUM were performed as described herein. Assays for SNB19 cells ($1 \times 10^4$ well$^{-1}$) were seeded in 8-well chamber slides, incubated for 24 hours and transfected with EV/SV, puPAR, puPA, pMMP-9 and pU$_2$M were performed as described herein.

SNB19 cells Boyden chamber invasion assay: The in vitro invasiveness of SNB19 cells in the presence of the vector expressing siRNA for cathepsin B and uPAR was assessed using a modified Boyden chamber assay. SNB19 cells were transfected with mock, EV, pU, pC or pCU vector expressing siRNA for cathepsin B and uPAR single or together for 48 h. $1 \times 10^6$ cells were suspended in 600 µl of serum-free medium supplemented with 0.2% BSA and placed in the upper compartment of the transwell chambers (Corning Costar Fischer Scientific Cat No. 07-200-158, Pittsburgh, Pa.) coated with Matrigel (0.7 mg/ml). The lower compartment of the chamber was filled with 200 µl of serum-free medium and the cells were allowed to migrate for 24 h. After incubation, the cells were fixed and stained with Hema-3 and photographed. Quantification of the invasion assay was performed. Assays for SNB19 cells ($1\times10^4$ well$^{-1}$) were seeded in 8-well chamber slides, incubated for 24 hours and transfected with EV/SV, puPAR, puPA, pMMP-9 and pU$_2$M were performed as described herein.

SNB19 Spheroid assay: SNB19 glioblastoma cells ($3\times10^6$) were seeded in 100 mm tissue culture plates (Corning, Corning, N.Y.) pre-coated with 0.75% agar prepared in DMEM and cultured until spheroid aggregates formed. Spheroids of 100-200 µm in diameter were selected and transfected with mock, empty vector, pC, pU and pCU for 48 h. Three days after infection, SNB19 spheroids were stained with the fluorescent dye DiI and placed in contact with fetal rat brain aggregates stained with DiO. The progressive destruction of fetal rat brain aggregates and invasion of SNB19 cells were observed by confocal laser scanning microscopy and photographed as described previously. The remaining volume of brain aggregates or tumor spheroids during co-cultures was determined as described previously. Spheroid assays for SNB19 cells transfected with EV/SV, puPAR, pMMP-9 and pUM were performed as described herein. Assays for SNB19 cells ($1\times10^4$ well$^{-1}$) were seeded in 8-well chamber slides, incubated for 24 hours and transfected with EV/SV, puPAR, puPA, pMMP-9 and pU$_2$M were performed as described herein.

Mice experiments for glioma analysis. SNB19 GFP cells ($2\times10^6$) were injected into the brains of nude mice using a stereotactic frame. After 8-10 days, the mice were treated with mock, empty vector EV/SV, pC, pU and pCU. The in vivo intracranial delivery of vectors was performed using Alzet (Direct Corp. Cupertino, Calif.) mini-osmotic pumps at the rate of 0.25 µl/hr, mock (PBS) of 150 µg vector DNA, 150 Rg pC, 150 µg pU, 150 µg pCU or puPAR vector (150 µg), pMMP-9 vector (150 µg) and pUM vector (150 µg) were injected into the brain (100 uL per mouse). All experiments were performed in compliance with institutional guidelines set by the Institutional Animal Control Users Committee that approves experiments at the University of Illinois College of Medicine at Peoria. After 5 weeks, or when the control mice started showing symptoms, mice were euthanized by cardiac perfusion with formaldehyde. The brains were then removed and paraffin embedded as per standard protocols. Sections were prepared and observed for GFP expression or were stained with H&E. The sections were blindly reviewed and scored semiquantitatively for tumor size in each case. The average tumor area per section was used to calculate tumor volume and compared between controls and treated groups. Experiments for SNB19 cells ($1\times10^4$ well$^{-1}$) were seeded in 8-well chamber slides, incubated for 24 hours and transfected with EV/SV, puPAR, puPA, pMMP-9 and pU$_2$M were performed as described herein.

Statistical Analysis: Statistical comparisons were performed using ANOVA for analysis of significance between different values using GraphPad Prism software (San Diego, Calif.). Values are expressed as mean SD from at least three separate experiments and differences were considered significant at a P value of less than 0.05.

Intracranial tumor growth inhibition. For the intracerebral tumor model, $2\times10^6$ SNB19 GFP cells were injected intracerebrally into nude mice. Tumors were allowed to grow for 10 days. At this time, animals were randomized into seven groups and EV/SV, puPAR, puPA, pMMP-9 and pU$_2$M (150 µg of each construct were injected into the brain using Alzet mini pumps at the rate of 0.25 µl h$^{-1}$ (six mice in each group). Five weeks after tumor inoculation, six mice from each group were sacrificed by cardiac perfusion with 3.5% formaldehyde in PBS. Their brains were removed and placed in 4% paraformaldehyde for 24 hours, paraffin embedded and sectioned. The sections were screened for GFP fluorescence to examine tumor growth under a fluorescent microscope. The sections were reviewed blindly and scored semiquantitatively for tumor size. The average tumor area in each section was used to calculate tumor volume and compared between controls and treated groups.

Matrigel invasion assay. The invasiveness of the transfected SNB19 cells was tested in vitro with the Boyden chamber invasion assay after transfection with either the empty vector (EV) or the vector expressing siRNA for cathepsin B and MMP-9 (pCM). Briefly, transwell inserts with 8-µm pores were coated with Matrigel (0.7 mg/ml) (Collaborative Research, Inc., Boston, Mass.). SNB19 cells were trypsinized and 500 µl of the cell suspension ($1\times10^6$ cells/ml) was added to the wells in triplicate. After incubation for 24 h at 37° C., cells that passed through the filters into the lower wells were quantified and expressed as a percentage of the sum of the cells in the upper and lower wells. Cells on the lower side of the membrane were fixed, stained with Hema-3 and photographed. Assays for other constructs described were also performed following the procedures described herein.

Delivery of nucleic acids: Delivery of the nucleic acids are accomplished using any type of methods such as for example, lipophilic agent, viruses including adeno, adeno associated or lenti or with modified viruses. Naked plasmid constructs that are circular or linear with blunt or sticky ends, as double stranded RNA, single stranded RNA, or DNA-RNA hybrids where one of the strands is DNA and the other is RNA, or having ribose or deoxy-ribose backbone on the same strand are also used. DNA, RNA or DNA-RNA hybrids coated with proteins or carbohydrates or combinations thereof, or used in conjunction with hormones or hormone derivatives. Chemically modified DNA or RNA or DNA-RNA hybrids can also be used as therapeutic molecules to induce RNAi targeting of uPAR, uPA, MMP-9 and Cathepsin B in any combination. The intended use would be on eukaryotic organisms or cell lines, preferably human and human cell lines.

Methods and therapeutic compositions known to those of skilled in art for delivering siRNAs or shRNAs are within the scope of the present disclosure. For example, siRNAs, shRNAs and other nucleic acids disclosed herein can be delivered into mammalian cells through techniques such as viral vector delivery, lipofection, electrochemical, and biochemical methods. Virus based delivery includes generating recombinant adenoviral, lentiviral, retroviral or any suitable vectors that harbor a nucleic acid of interest and delivering the viral vectors using techniques known to those of skilled in the art. Liposomes-based delivery systems include lipofection and cardiolipin-based compositions. Direct delivery of naked nucleic acids and in combination with chemical or biochemical adjuvants is within the scope of this disclosure. For example, circular plasmids harboring siRNAs against a target sequence such as, for example, uPA, uPAR, MMP-9, and cathepsin B can be directly injected or delivered intratumorally or can be injected intra-peritoneally. Similarly, synthetic or chemically prepared nucleic acids also can be delivered intratumorally or intraperitoneally. In addition, selective or specific delivery of siRNAs or nucleic acids that express siRNAs can also be achieved through appropriate coupling with another agent such as a peptide nucleic acid (PNA) or an antibody or any suitable targeting agent. The above-mentioned techniques and methods are suitable and adaptable to deliver nucleic acid sequences inter cellularly, intra cellularly, in vitro cell cultures, in vivo, inside an organ, across the blood-brain barrier, to prostrate cancers, gliomas, breast cancers, and colon cancers.

Intracranial tumor growth inhibition: For the intracerebral tumor model, 2×106 4910 xenograft tumor cells were intracerebrally injected into nude mice. Ten days after tumor implantation, the mice were treated with intraperitoneal injections of pU2 (150 μg/injection/mouse) every other day three times. Control mice were either injected with PBS alone or with empty plasmid, vector (150 μg/injection/mouse). Five weeks after tumor inoculation, six mice from each group were sacrificed by cardiac perfusion with 3.5% formaldehyde in PBS, their brains removed, and paraffin sections prepared. Sections were stained with hematoxylin and eosin to visualize tumor cells and to examine tumor volume (32, 33). The sections were blindly reviewed and scored semiquantitatively for tumor size. Whole mount images of brains were also taken to determine infiltrative tumor morphology. The average tumor area per section integrated to the number of sections where the tumor was visible was used to calculate tumor volume and compared between controls and treated groups. RT-PCR was performed on fresh or paraffin-embedded brain tissue for OAS1 pcDNA3 plasmid and GAPDH as previously described.

Animal survival analysis: Nude mice were implanted with intracranial 4910 xenograft tumors and their survival ability was determined based on symptoms of intracranial pressure, arched back and dehydration. If the animals exhibited excessive pain, they were euthanized. Two sets of animals were used (6 mice/group). Both sets were implanted with intracranial xenograft tumors as described previously. Ten days after tumor implantation, the mice were treated with intraperitoneal injections of pU2 (150 μg/injection/mouse) every other day three times. Control mice were either injected with PBS alone or EV/SV (150 μg/injection/mouse). The mice were maintained in clean room conditions and monitored every day for 112 days after which the experiment was artificially terminated. Brains were collected from the control and treated mice, paraffin embedded, sectioned, and H & E stained per standard protocols. The survival curve was plotted as per standard methods and graphically represented as percent survival.

Construction of hpRNA expressing plasmid: A pcDNA3 plasmid with a CMV promoter was used in the construction of the hpRNA-expressing vector. The uPA sequence agcttGagagccctgctggcgcgccatatataatggcgcgccagcagggctctca (SEQ ID NO: 17) and uPAR sequence gatccTacagcagtggagagcgattatatataataatcgctctccactgctgtag (SEQ ID NO: 18) were used for the siRNA sequence. Inverted repeat sequences were synthesized for both uPA and uPAR. The inverted repeats were laterally symmetrical making them self-complimentary with a five-base pair mismatch in the loop region. This five-base pair mismatch would aid in the loop formation of the hpRNA.

Primers used for PCR and RT-PCR for Example 36:

```
CMV to BGH:
Forward      CTGGTGTCGACCTGCTTCCGCGATGTACGGGC
             (SEQ ID NO: 15),
Reverse      CTGGTGTCGACATCCCCAGCATGCCTGCTAT
             (SEQ ID NO: 16)

uPAR:
Forward      CATGCAGTGTAAGACCCAACGGGGA
             (SEQ ID NO: 23)
```

```
                       -continued
Reverse      AATAGGTGACAGCCCGGCCAGAGT
             (SEQ ID NO: 24)

uPA:
Forward      TGCGTCCTGGTCGTGAGCGA
             (SEQ ID NO: 21)
Reverse      CAAGCGTGTCAGCGCTGTAG
             (SEQ ID NO: 39)

GAPDH:
Forward      CGGAGTCAACGGATTTGGTCGTAT
             (SEQ ID NO: 25)
Reverse      AGCCTTCTCCATGGTGGTGAAGAC
             (SEQ ID NO: 26)

OAS1:
Forward      AGGTGGTAAAGGGTGGCTCC
             (SEQ ID NO: 13)
Reverse      ACAACCAGGTCAGCGTCAGAT
             (SEQ ID NO: 14)
```

Sequences: Sequences for various siRNA constructs (partial sequence) are disclosed herein. The underlined portion indicates the self-complementary inverted repeats. The bold indicates the intervening loop sequence.

UPAR-uPA (SEQ ID NO: 32)

GCTAACTAGA GAACCCACTG CTTACTGGCT TATCGAAATT

AATACGACTC ACTATAGGGA GACCCA agcttGagagccctgctggcg cgccatatataatggcgcgccagcagggctctca AGCT TGGTACCGAG CTCG gatccTacagcagtggagagcgattatatataata atcgctctccactgctgtag GATCCA CTAGTAACGG CCGCCAGTGT

GCTGGAATTC TGCAGATATC CATCACACTG GCGGCCGCTC

GAGCATGCAT CTAGAGGGCC CTATTCTATA GTGTCACCTA

AATGCTAGAG CTCGCTGATC AGCCTCGACT GTGCCTTCTA

GTTGCCAGCC ATCTGTTGTT TGCCCCTCCC CCGTGCCTTC

CTTGACCCTG GAAGGTGCCA CTCCCACTGT CCTTTCCTAA

TAAAAaaaaaaaaaaaaaaaaaaa

Space between hairpin loops 22 bases

UPAR-MMP-9 (SEQ ID NO: 33)

GCTAACTAGA GAACCCACTG CTTACTGGCT TATCGAAATT

AATACGACTC ACTATAGGGA GACCCA AGCT TGGTACCGAG CTCG gatccTacagcagtggagagcgattatatataataatcgctctccactg ctgtag GATCCA CTAGTAACGG CCGCCAGTGT GCTGG aattCaagt ggcaccaccacaacaatatataattgttgtggtggtgccacttg AATTC

TGCAGATATC CATCACACTG GCGGCCGCTC GAGCATGCAT

CTAGAGGGCC CTATTCTATA GTGTCACCTA AATGCTAGAG

CTCGCTGATC AGCCTCGACT GTGCCTTCTA GTTGCCAGCC

ATCTGTTGTT TGCCCCTCCC CCGTGCCTTC CTTGACCCTG

GAAGGTGCCA CTCCCACTGT CCTTTCCTAA TAAAAaaaaaaaaaaaa aaaaaaa

Space between hairpin loops 35 bases

UPAR CB (SEQ ID NO: 34)

```
GCTAACTAGA GAACCCACTG CTTACTGGCT TATCGAAATT

AATACGACTC ACTATAGGGA GACCCA AGCT TGGTACCGAG CTCG gatccTacagcagtggagagcgattatatataataatcgctctccactg ctgtag GATCCA CTAGTAACGG CCGCCAGTGT GCTGG AATTC TGCAGATATC CATCACACTG GCGGCCGC tcgaGgtggcctctatgaa tcccaatatataattgggattcatagaggccacc TC GAGCATGCAT

CTAGAGGGCC CTATTCTATA GTGTCACCTA AATGCTAGAG

CTCGCTGATC AGCCTCGACT GTGCCTTCTA GTTGCCAGCC

ATCTGTTGTT TGCCCCTCCC CCGTGCCTTC CTTGACCCTG

GAAGGTGCCA CTCCCACTGT CCTTTCCTAA TAAAAaaaaaaaaaaaa aaaaaaa

Space between hairpin loops 68 bases
```

MMP9-CB (SEQ ID NO: 35)

```
GCTAACTAGA GAACCCACTG CTTACTGGCT TATCGAAATT

AATACGACTC ACTATAGGGA GACCCA AGCT TGGTACCGAG CTCG

GATCCA CTAGTAACGG CCGCCAGTGT GCTGG aattCaagtggcacc accacaacaatatataattgttgtggtggtgccacttg AATTC TGCAGATATC CATCACACTG GCGGCCGC tcgaGgtggcctctatgaa tcccaatatataattgggattcatagaggccacc TC GAGCATGCAT

CTAGAGGGCC CTATTCTATA GTGTCACCTA AATGCTAGAG

CTCGCTGATC AGCCTCGACT GTGCCTTCTA GTTGCCAGCC

ATCTGTTGTT TGCCCCTCCC CCGTGCCTTC CTTGACCCTG

GAAGGTGCCA CTCCCACTGT CCTTTCCTAA TAAAAaaaaaaaaaaaa aaaaaaa

Space between hairpin loops 37 bases
```

UPAR, uPA and Cath B (SEQ ID NO: 36)

```
GCTAACTAGA GAACCCACTG CTTACTGGCT TATCGAAATT

AATACGACTC ACTATAGGGA GACCCA AGCT TGGTACCGAG CTCG gatccTacagcagtggagagcgattatatataataatcgctctccactg ctgtag GATCCA CTAGTAACGG CCGCCAcTacagcagtggagagcga ttatatataataatcgctctccactgctgtagGTGT GCTGG AATTC TGCAGATATC CATCACACTG GCGGCCGC tcgaGgtggcctctatgaa tcccaatatataattgggattcatagaggccacc TC GAGCATGCAT

CTAGAGGGCC CTATTCTATA GTGTCACCTA AATGCTAGAG

CTCGCTGATC AGCCTCGACT GTGCCTTCTA GTTGCCAGCC

ATCTGTTGTT TGCCCCTCCC CCGTGCCTTC CTTGACCCTG

GAAGGTGCCA CTCCCACTGT CCTTTCCTAA TAAAAaaaaaaaaaaaa aaaaaaa
```

DOCUMENTS CITED

These documents are listed only to the extent they relate to materials and methods in the present disclosure.

Adachi, Y. et al., (2001) *J Biol Chem* 276, 47171-47177
Aguirre-Ghiso, J. A., et al., (2003) *Cancer Res.* (2003) 63, 1684-1695
Aguirre Ghiso, et al., (1999) *J. Cell Biol* 147, 89-104
Ahmed, N., et al., (2003) *Br. J. Cancer* 89, 374-384
Aoki, I., et al., (2003) *J Steroid Biochem Mol Biol* 84, 217-222
Bergers, G., et al., (1999) *Science* 284, 808-812
Blasi, F., Carmeliet, P. (2002) *Nat. Rev. Mol Cell Biol* 3, 932-943
Boyd, D. D., et al., (2003) *Am. J. Pathol.* 162, 619-626
Brown, P. D., et al., (1993) *J Natl Cancer Inst* 85, 574-578
Caplen, N. J., et al., (2001) *Proc Natl Acad Sci USA* 98, 9742-9747
Chandrasekar, N., et al., (2003) *Oncogene* 22, 392-400
Choe, G., et al., (2002) *Clin Cancer Res* 8, 2894-2901
D'Alessio, S., et al., (2004) *Int. J. Cancer* 110, 125-133
Dahiya, R., et al., (1994) *Int J. Cancer* 59, 126-132
Degryse, B., et al., (2001) *J Cell Biol* 152, 1197-1206
Drummond, A. H., et al., (1999) *Ann N Y Acad Sci* 878, 228-235
Dumler, I., et al., (1998) *J. Biol. Chem.* 273: 315-321
Elbashir, S. M., et al., (2002) *Methods* 26, 199-213
Ellis, V. and Dano, K. (1993) *J Biol Chem* 268, 4806-4813
Fabbrini, M. S., et al., (1997) *FASEB J.* 11, 1169-1176
Forsyth, P. A., et al (1999) *Br J Cancer* 79, 1828-1835
Giannelli, V., Fontana, et al (1997) *Infect Immun* 65, 331-334
Giese, A. and Westphal, M. (1996) *Neurosurgery* 39, 235-250
Go, Y., et al (1997) *Clin Exp Metastasis* 15, 440-446
Guo, Y., et al (2000) *FASEB J* 14, 1400-1410
Hidalgo, M., et al (2002) *Nature* 418, 244-251
Hood, J. D., et al (2002) *Science* 296, 2404-2407
Hoosein, N. M., et al (1991) *Cancer Commun.* 3, 255-264
Jemal, A., et al (2003) *CA Cancer J. Clin.* 53, 5-26
Jiang, M., et al (2004) *Oligonucleotides* 14, 239-248
Jo, M., et al (2003) *J Biol Chem* 278, 1642-1646
Joossens, J., et al (2004) *J. Med. Chem.* 47, 2411-2413
Kajita, M., et al (2001) *J Cell Biol* 153, 893-904
Keer, H. N., et al (1991) *Prostate* 18, 201-14
Kim, S. J., et al (2003) *Clin Cancer Res.* 9, 5161-5170
Kim, S. J., et al (2004) *Cancer Res.* 64, 4201-4208
Kin, Y., et al (2000) *Int J Oncol* 17, 61-65
Kondraganti, S., et al (2000) *Cancer Res* 60, 6851-6855
Konakova, M., et al (1998) *Eur J Biochem* 253, 421-429
Laiho, M. and Keski-Oja, J. (1989) *Cancer Res* 49, 2533-2553
Lakka, S. S., et al (2000) *Clin Exp Metastasis* 18, 245-252
Lakka, S. S., et al (2002) *Oncogene* 21, 5601-5608
Lakka, S. S., et al (2002) *Oncogene* 21, 8011-8019
Laniado, M. E., et al (1997) *Am. J. Pathol.* 150, 1213-1221
Lee, K. H., et al (1992) *Cancer Res* 52, 6553-6560
Lozonschi, L., et al (2001) *Exp. Cell. Res.* 264, 326-336
Ma, Z., et al (2001) *J. Cell Sci.* 114, 3387-3396
Mamoune, A., et al (2004) *Exp. Cell Res.* 299, 91-100
Margheri, F. et al (2005) *Gene Ther.* 12, 702-714
Mazzieri, R., et al (1997) *EMBO J* 16, 2319-2332
Ossowski, L., Russo-Payne, H., and Wilson, E. L. (1991) *Cancer Res* 51, 274-281
McManus, M. T. and Sharp, P. A. (2002) *Nat Rev Genet* 3, 737-747
Miyagishi, M., Hayashi, M., Taira, K. (2003) *Antisense Nucleic Acid Drug Dev.* 13, 1-7

Miyagishi, M. and Taira, K. (2002) *Nat Biotechnol* 20, 497-500

Mohan, R. R. et al (2000) *Invest Ophthalmol. Vis. Sci* 41, 1327-1336

Mohanam, S., et al (1997) *Oncogene* 14, 1351-1359

Mora, L. B., et al (2002) *Cancer Res.* 62, 6659-6666

Mori, T., Abe, T., Wakabayashi, Y., Hikawa, T., Matsuo, K., Yamada, Y., Kuwano, M., and Hori, S. (2000) *J Neurooncol* 46, 115-123

Moses, M. A. (1997) *Stem Cells* 15, 180-189 Mohan, P. M., Chintala, S. K., Mohanam, S., Gladson, C. L. et al (1999) *Cancer Res* 59, 3369-3373

Naldini, L. et al (1992) *Eur. Mol. Biol Org.* 11, 4825-4833

Nishimura, K., Matsumniya, K., Miura, H., Tsujimura, A., Nonomura, N., Matsumoto, K., Nakamura, T., Okuyama, A. (2003) *Int. J. Androl* 26, 175-179

Nguyen, D. H. D., Hussaini, I. M., and Gonias, S. L. (1998) *J. Biol. Chem.* 273, 8502-8507

Nguyen, D. H. D., Webb, D. J., Catling, A. D., Song, Q., Dhakephalkar, A., Weber, M. J., Ravichandran, K. S., and Gonias, S. L. (2000) *J. Biol. Chem.* 275, 19382-19388

Nguyen, D. H., Hussaini, I. M., and Gonias, S. L. (1998) *J Biol Chem* 273, 8502-8507

Paddison, P. J. and Hannon, G. J. (2002) *Cancer Cell* 2, 17-23

Pakneshan, et al (2004) *J. Biol. Chem.* 279, 31735-31744.

Pakneshan, P., Xing, R. H., Rabbani, S. A. (2003) *FASEB J.* 17, 1081-1088

Park, M. J. et al (2002) *Cancer Res* 62, 6318-6322

Patel, P., Ashdown, D., James, N. (2004) *Prostate Cancer Prostatic Dis.* 7, S14-S19

Pinthus, J. H. et al (2004) *J. Clin. Invest.* 114, 1774-1781

Rabbani, S. A., Gladu, J. (2002) *Cancer Res.* 62, 2390-2397

Rakic, J. M., et al (2003) *Invest Ophthalmol Vis Sci* 44, 3186-3193

Ramos-DeSimone, N., Hahn-Dantona, E., Sipley, J., Nagase, H., French, D. L., and Quigley, J. P. (1999) *J Biol Chem* 274, 13066-13076

Rao, J. S. (2003) *Nat. Rev. Cancer.* 3, 489-501

Rao, J. S., et al (1993) *Cancer Res* 53, 2208-2211

Resnati, M., et al (2002) *Proc. Natl. Acad. Sci. USA.* 99, 1359-1364

Rye, P. D., Stigbrand, T. (2004) *Tumour Biol.* 25: 329-336

Salvi, A., Arici, B., De Petro, G., Barlati, S. (2004) *Mol Cancer Ther.* 3, 671-678

Sawaya, R., et al (1998) *Biochem Biophys Res Commun* 251, 632-636

Sato, S., Kopitz, C., Schmalix, W. A., Muehlenweg, B., Kessler, H., Schmitt, M., Kruger, A., Magdolen, V. (2002) *FEBS Lett.* 528, 212-216

Schuh, T., et al (2003) *Biol. Chem.* 384, 311-315

Schweinitz, A. et al (2004) *J. Biol. Chem.* 279, 33613-33622

Shah, R. B. et al (2004) *Cancer Res.* 64, 9209-9216

Sharp, P. A. (2001) *Genes Dev* 15, 485-490

Simon, C., Goepfert, H., and Boyd, D. (1998) *Cancer Res* 58, 1135-1139

Singh, S. et al (2004) *Clin Cancer Res.* 10, 8743-8750

Sontheimer, E. J. (2005) *Nat. Rev. Mol Cell Biol.* 6, 127-138

Stewart, D. A., Cooper, C. R., Sikes, R. A. (2004) *Reprod. Biol. Endocrinot.* 2 2

Tang, H., et al (1998) *J Biol Chem* 273, 18268-18272

Tarui, T., et al (2003) *J. Biol. Chem.* 278, 29863-29872

Trisciuoglio, et al (2004) *J Biol Chem* 279, 6737-6745

Usher, P. A., Thomsen, O. F., Iversen, P., Johnsen, M., Brunner, N., Hoyer-Hansen, G., Andreasen, P., Dano, K., Nielsen, B. S. (2005) *Int. J. Cancer* 113, 870-880

Woessmann, W., et al (2003) *Rev. Clin. Exp. Hematol* 7, 270-291

Yamamoto, M., et al (1994) *Cancer Res* 54, 5016-5020

Yao, J., et al (2001) *Oncogene* 20, 8066-8074

Yu, Q., Grammatikakis, N., and Toole, B. P. (1996) *Dev Dyn* 207, 204-214

Yu, Q. and Stamenkovic, I. (2000) *Genes Dev* 14, 163-176

Zhang, X., et al (2004) *Cancer Res.* 64, 7086-7091

Zhang, Y., et al (2004) *Clin. Cancer Res.* 10, 3667-3677

Zhang, Z., et al (2003) *Proc. Natl. Acad. Sci. USA.* 100, 11636-11641

The invention claimed is:

1. A multicistronic short interfering RNA expressing construct comprising at least a first and a second self-complementary inverted complement repeat sequence separated by an intervening sequence of about 22-68 base pairs in length, wherein the construct is used to suppress angiogenesis, inhibit tumor formation and to regress pre-formed tumors, wherein the first inverted complement repeat sequence comprises a nucleotide sequence of urokinase-type plasminogen activator receptor (uPAR) and the second inverted complement repeat sequence comprises a nucleotide sequence of matrix metalloprotease 9 (MMP-9) and wherein the self complementary sequence of uPAR is CTACAGCAGTG-GAGAGCGATT-loop-AATCGCTCTCCACTGCTGTAG (SEQ ID NO: 2) and the self complementary sequence of MMP-9 is CAAGTGGCACCACCACAACAA-loop-TTGT-TGTGGTGGTGCCACTTG (SEQ ID NO: 4).

2. The multicistronic construct of claim 1, wherein the intervening sequence is any sequence of up to 68 bases.

3. The multicistronic construct of claim 1 wherein the intervening sequence is selected from the group consisting of GATCCA CTAGTAACGG CCGCCAGTGT GCTGG AATT (SEQ ID NO: 5) and GATCCACTAG TAACGGCCGC CAGTGTGCTG GAATTCTGCA GATATCCATC ACACTGGCGG CCGCTCGA (SEQ ID NO: 7).

4. The multicistronic construct of claim 1, wherein the construct is a circular or linear nucleic acid.

5. A method of inhibiting formation of tumors or regressing pre-formed tumors, the method comprising:

(a) administering the short interfering RNA multicistronic construct of claim 1 to the tumors; and (b) reducing expression of a plurality of genes expressed in the tumors and targeted by the short interfering RNA construct, thereby inhibiting the tumors.

6. The method of claim 5, wherein the tumors are inhibited by reducing at least one of tumor cell proliferation, tumor cell invasion, tumor cell migration and angiogenesis.

7. The method of claim 5, wherein the tumors are selected from the group consisting of prostate cancer, glioma, meningioma, colon cancer, lung cancer, breast cancer, pancreatic cancer and melanoma.

8. The method of claim 7, wherein the construct is administered through direct delivery.

9. A recombinant cell transformed with the multicistronic construct of claim 1.

10. A recombinant virus transformed with the multicistronic construct of claim 1.

11. The multicistronic construct of claim 1, wherein the uPAR and MMP-9 sequences are driven by a single promoter.

12. The multicistronic construct of claim 1 is synthetic.

13. The construct of claim 1 wherein the inverted complement repeat sequence is terminated by one or more adenine bases at the 3' end.

* * * * *

UNITED STATES PATENT AND TRADEMARK OFFICE
CERTIFICATE OF CORRECTION

| | | |
|---|---|---|
| PATENT NO. | : 7,893,035 B2 | Page 1 of 1 |
| APPLICATION NO. | : 11/748733 | |
| DATED | : February 22, 2011 | |
| INVENTOR(S) | : Jasti S. Rao et al. | |

It is certified that error appears in the above-identified patent and that said Letters Patent is hereby corrected as shown below:

In Column 1, the paragraph beginning at line 11 should read as follows:

--This invention was made with government support under (CA092393; NS047699; CA075557; CA076350; CA116708; CA085216; CA095058; and NS057529) awarded by the National Institutes of Health. The government has certain rights in the invention.--

Signed and Sealed this

Twenty-sixth Day of April, 2011

David J. Kappos
*Director of the United States Patent and Trademark Office*